United States Patent
Zhao

(10) Patent No.: US 10,307,391 B2
(45) Date of Patent: *Jun. 4, 2019

(54) DISULFUR BRIDGE LINKERS FOR CONJUGATION OF A CELL-BINDING MOLECULE

(71) Applicant: Suzhou M-Conj Biotech Co., Ltd., Suzhou (CN)

(72) Inventor: Robert Yongxin Zhao, Lexington, MA (US)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/479,903

(22) Filed: Apr. 5, 2017

(65) Prior Publication Data

US 2017/0202975 A1 Jul. 20, 2017

Related U.S. Application Data

(62) Division of application No. 14/799,712, filed on Jul. 15, 2015.

(51) Int. Cl.
*A61K 31/5365* (2006.01)
*A61K 31/337* (2006.01)
(Continued)

(52) U.S. Cl.
CPC .......... *A61K 31/337* (2013.01); *A61K 31/404* (2013.01); *A61K 31/5365* (2013.01);
(Continued)

(58) Field of Classification Search
None
See application file for complete search history.

(56) References Cited

U.S. PATENT DOCUMENTS 5,316,888 A 5/1994 Naruse et al.
2010/0278845 A1* 11/2010 Heavner .............. C07K 14/685
424/179.1
(Continued)

FOREIGN PATENT DOCUMENTS

JP 5-297544 A 11/1993
WO 2018/086139 A1 5/2018

OTHER PUBLICATIONS

Database Caplus Chemical Abstracts Service, Columbus, Ohio, US; Database Accession No. 2012:1667427, Abstract of U.S. Pat. No. 8,846,849, Bordoloi et al., Ethicon, Inc., USA, Nov. 15, 2012 (Year: 2012).*

(Continued)

*Primary Examiner* — Karl J Puttlitz
(74) *Attorney, Agent, or Firm* — Buchanan Ingersoll & Rooney PC

(57) ABSTRACT

The present invention relates to novel disulfur bridge linkers containing hydrazine used for the specific conjugation of compounds/cytotoxic agents to a cell-binding molecule, through bridge linking a pair of thiols on the cell-binding molecule. The invention also relates to methods of making such linkers, and of using such linkers in making homogeneous conjugates, as well as of application of the conjugates in treatment of cancers, infections and autoimmune disorders.

16 Claims, 12 Drawing Sheets

(51) Int. Cl.

| | |
|---|---|
| A61K 45/06 | (2006.01) |
| C07C 243/28 | (2006.01) |
| C07D 207/452 | (2006.01) |
| C07C 275/50 | (2006.01) |
| C07C 311/55 | (2006.01) |
| C07D 213/71 | (2006.01) |
| C07K 5/065 | (2006.01) |
| C07D 403/14 | (2006.01) |
| C07K 5/078 | (2006.01) |
| C07D 405/14 | (2006.01) |
| C07D 413/14 | (2006.01) |
| C07D 417/14 | (2006.01) |
| C07D 493/08 | (2006.01) |
| C07D 498/14 | (2006.01) |
| C07D 519/00 | (2006.01) |
| A61K 31/404 | (2006.01) |
| A61K 31/5513 | (2006.01) |
| A61K 31/551 | (2006.01) |
| A61K 49/00 | (2006.01) |
| A61K 47/68 | (2017.01) |

(52) U.S. Cl.
CPC ........ *A61K 31/551* (2013.01); *A61K 31/5513* (2013.01); *A61K 45/06* (2013.01); *A61K 47/6803* (2017.08); *A61K 47/6889* (2017.08); *A61K 49/0002* (2013.01); *C07C 243/28* (2013.01); *C07C 275/50* (2013.01); *C07C 311/55* (2013.01); *C07D 207/452* (2013.01); *C07D 213/71* (2013.01); *C07D 403/14* (2013.01); *C07D 405/14* (2013.01); *C07D 413/14* (2013.01); *C07D 417/14* (2013.01); *C07D 493/08* (2013.01); *C07D 498/14* (2013.01); *C07D 519/00* (2013.01); *C07K 5/06078* (2013.01); *C07K 5/06139* (2013.01); *Y02A 50/385* (2018.01); *Y02A 50/402* (2018.01); *Y02A 50/414* (2018.01); *Y02A 50/415* (2018.01); *Y02A 50/463* (2018.01); *Y02A 50/473* (2018.01); *Y02A 50/49* (2018.01)

(56) References Cited

U.S. PATENT DOCUMENTS

| | | | | |
|---|---|---|---|---|
| 2012/0288530 | A1* | 11/2012 | Bordoloi | A61L 24/106 424/400 |
| 2015/0031861 | A1* | 1/2015 | Smith | C07K 16/2887 530/387.3 |

OTHER PUBLICATIONS

Office Action dated Aug. 21, 2017 by the U.S. Patent and Trademark Office in co-pending U.S. Appl. No. 14/799,712. (12 pages).
Database Caplus Chemical Abstracts Service, Colombus, Ohio, US; Database Accession No. 2012:1667427, Abstract of US 20120288530, Ethicon, Inc., Usa, Bordoloi et al., Nov. 15, 2012. (2 pages).
Database Caplus Chemical Abstracts Service, Columbus, Phio, US; Registry No. 1411994-79-0, Dec. 5, 2012, 3.6.13.16-Tetraoxa-9,10-diazaoctadecanedioic acid, 9,10-bis[2-[[2-[2-[{2,5-dioxo-1-pyrrolidinyl)oxy]-2-oxoethoxy]acetyl]oxy]ethyl]-5,14-dioxo-, 1,18-bis(2,5-dioxo-1-pyrrolidinyl) ester. (2 pages).
Office Action dated Jan. 26, 2018, by the U.S. Patent and Trademark Office in parent U.S. Appl. No. 14/799,712. (13 pages).
Office Action issued by the U.S. Patent and Trademark Office in the U.S. Appl. No. 14/799,712, dated Oct. 3, 2016, U.S. Patent and Trademark Office, Alexandria, VA. (7 pages).
Office Action issued by the U.S. Patent and Trademark Office in the U.S. Appl. No. 14/799,712, dated Mar. 21, 2017, U.S. Patent and Trademark Office, Alexandria, VA. (9 pages).
Database Caplus Chemical Abstracts Service, Columbus, Ohio, US; Database Accession No. 1994:284837, Abstract of JJP 05297544 (JP 544), Naruse et. al., Fuji Photo Film Co. Ltd., Japan, Nov. 12, 1993.
Database Caplus Chemical Abstracts Service, Columbus, Ohio, US; Database Accession No. 1912:6440, Abstract of Stolle, Berichte der Deuschen Gesellschaft (1912), 45, 273-89.
Office Action dated Jul. 9, 2018, by the U.S. Patent and Trademark Office in related U.S. Appl. No. 14/799,712. (8 pages).
Office Action dated Dec. 6, 2018, by the U.S. Patent and Trademark Office in related U.S. Appl. No. 14/799,712. (9 pages).
Office Action dated May 23, 2018, by the U.S. Patent and Trademark Office in related U.S. Appl. No. 14/431,154 (30 pages).
Adumeau et al., "Site-Specifically Labeled Immunoconjugates for Molecular Imaging—Part 1: Cysteine Residues and Glycans," Molecular Imaging and Biology, (2016), vol. 18., pp. 1-17.
Lyu et al., "A Switchable Site-Specific Antibody Conjugate," ACS Chemical Biology, (2018), vol. 13, No. 7. (24 pages).
Office Action dated Jan. 7, 2019, by the U.S. Patent and Trademark Office in related U.S. Appl. No. 15/479,859. (8 pages).
Notice of Allowance dated Dec. 26, 2018, by the U.S. Patent and Trademark Office in related U.S. Appl. No. 15/431,154. (9 pages).
Notice of Allowance dated Jan. 24, 2019, by the U.S. Patent and Trademark Office in related U.S. Appl. No. 14/799,712. (9 pages).

* cited by examiner m =0~100, n = 1~20, mAb is antibody

DISULFUR BRIDGE LINKERS FOR CONJUGATION OF A CELL-BINDING MOLECULE

CROSS REFERENCE TO RELATED APPLICATIONS

This application is a division of U.S. application Ser. No. 14/799,712, filed on Jul. 15, 2015, entitled "DISULFUR BRIDGE LINKERS FOR CONJUGATION OF A CELL-BINDING MOLECULE." The content of the prior application is hereby incorporated by reference in its entirety.

FIELD OF THE INVENTION

The present invention relates to the preparation of novel disulfur bridge linkers used for the specific conjugation of compounds, in particular, cytotoxic agents to a cell-binding molecule, through bridge linking pairs of thiols on a cell-binding molecule. The present invention also relates to methods of making cell-binding agent-drug (cytotoxic agent) conjugates in a specific manner comprising either modification of drugs with these linkers first, followed by reaction with prepared cell-binding agents; or modification of cell-binding agents with these linkers first, followed by reaction with drugs.

BACKGROUND OF THE INVENTION

Traditional chemotherapy is often accompanied by systemic toxicity to the patient. Monoclonal antibody which can offer an alternative tumor-selective treatment approach via discriminating antigens on cancer cells, is normally not sufficiently potent to be therapeutically active by itself. Antibody-drug conjugates (ADCs), which by their name have the exquisite targeting ability of antibodies in combination with the cytotoxic action of anticancer agents, enable to target and deliver drugs to cancer cells leaving normal cells largely unaffected, thus improving the therapeutic index of chemotherapeutic agents. since US FDA approvals of Adcetris (brentuximab vedotin) in 2011 and Kadcyla (ado-trastuzumab emtansine) in 2013, the applications of antibody-drug conjugate (ADC) as a promise targeted treatment of cancers have been exploded and almost every major pharmaceutical and biotech company has adopted this approach (Chari, R. et al, Angew. Chem., Int. Ed. 2014, 53, 3796-3827; Sievers, E. L. et al. Annu Rev Med. 2013, 64, 15-29; Mehr-ling, T. Future Oncol, 2015, 11, 549). Antibody-drug conjugates are now a drug class with a robust pipeline and a flurry of deal-making among pharmaceutical companies. With more than 50 ADCs currently in various stages of clinical trials according to www.clinictrails.gov, and even more in preclinical and/or are ready to enter first-in-human trials, the market is rife with eager anticipation of more ADC drugs to be approved by regulators.

The first-generation ADCs, including Kadcyla and Adcetris, are produced through nonselective conjugation of native lysine amines or interchain cysteine thiols on an antibody respectively to a cytotoxic drug. Since there are over 50 surface-exposed lysines and 8 hinge cysteine residues in IgG1 antibodies, this nonselective conjugation results in randomly cross-linkage of cytotoxic drugs to practically all areas of the antibody molecule, particularly having a diverse population of ADCs with a wide distribution of drugs per antibody (DAR) (Wang, L., et al. 2005 Protein Sci. 14, 2436; Hamblett, K. J., et al. 2004 Clin. Cancer Res. 10, 7063). Thus some of the undesired ADC subpopulation could lead to shorter circulation half-life, lower efficacy, potentially increased off-target toxicity and a wide range of in vivo pharmacokinetic (PK) properties (Hamblett, K. J. et al, Clin. Cancer Res. 2004, 10, 7063-7070; Adem, Y. T. et al, Bioconjugate Chem. 2014, 25, 656-664; Boylan, N. J. Bioconjugate Chem., 2013, 24, 1008-1016; Strop, P., et al 2013 Chem. Biol. 20, 161-167). In addition, with this classical conjugation, the batch-to-batch consistency in ADC production can be challenging and may require diligent manufacturing capabilities (Wakankar, A. mAbs, 2011, 3, 161-172).

Therefore, biotechnology companies and academic institutions are intensely focusing on establishing novel reliable methods for site-specific ADC conjugation. So far, there are several approaches developed in recent years for site selective ADC preparation (Panowski, S, 2014, mAbs 6, 34). They include incorporation of unpaired cysteines, e.g. engineered reactive cysteine residues, called THIOMAB from Genentech (Junutula, J. R., et al 2010 Clin. Cancer Res. 16, 4769; Junutula, J. R., et al 2008 Nat Biotechnol. 26, 925-32; U.S. Pat. Nos. 8,309,300; 7,855,275; 7,521,541; 7,723,485, WO2008/141044), genetically introduced glutamine tag with Streptoverticillium mobaraense transglutaminase (mTG) (Strop, P., Bioconjugate Chem., 2014, 25, 855-862; Strop, P., et al., 2013, Chem. Biol. 20, 161-167; U.S. Pat. No. 8,871,908 for Rinat-Pfizer) or with Microbial transglutaminase (MTGase) (Dennler, P., et al, 2014, Bioconjug. Chem. 25, 569-578. US pat appl 20130189287 for Innate Phainia; U.S. Pat. No. 7,893,019 for Bio-Ker S.r.l. (IT)), incorporation of thiolfucose (Dennler, P., et al, 2014 Bioconjugate Chemistry 25, 569; Okeley, N. M., et al 2013 Bioconjugate Chem. 24, 1650), incorporation of unnatural amino acids through mutagenesis (Axup, J. Y., et al., 2012, Proc. Natl. Acad. Sci. 109, 16101-16106; Zimmerman, E. S., et al., 2014, Bioconjug. Chem. 25, 351-361; Wu, P., et al, 2009 Proc. Natl. Acad. Sci. 106, 3000-3005; Rabuka, D., et al, 2012 Nat. Protoc. 7, 1052-67; U.S. Pat. No. 8,778,631 and US Pat Appl. 20100184135, WO2010/081110 for Sutro Biopharma; WO2006/069246, 2007/059312, U.S. Pat. Nos. 7,332,571, 7,696,312, and 7,638,299 for Ambrx; WO2007/130453, U.S. Pat. Nos. 7,632,492 and 7,829,659 for Allozyne), Incorporation of selenocysteine into antibodies (Hofer, T., et a12009, Biochemistry 48, 12047-12057; U.S. Pat. No. 8,916,159 for US National Cancer Institute), Convention of cysteines located in the CXPXR consensus sequence to formylglycine (FGly) with formylglycine generating enzyme (FGE) (Drake, P. M., et al., 2014, Bioconjug. Chem. 25, 1331-1341. Carrico; Isaac S. et al U.S. Pat. Nos. 7,985,783; 8,097,701; 8,349,910, and US Pat Appl 20140141025, 20100210543 for Redwood Bioscience), and through glycoengineeringly introduction of sialic acid with the use of galactosyl- and sialytransferases (Zhou, Q., et al 2014, Bioconjug. Chem., 25, 510-520, US Pat Appl 20140294867 for Sanofi-Genzyme). These above methods have produced nearly homogeneous product profiles, but they are required antibody-engineering processes and reoptimization of cell culture conditions. Moreover, expression yields for genetic encoding of an unnatural amino acid were typically not promisingly high enough (Tian, F., et al, 2014, Proc. Natl. Acad. Sci. U.S.A. 111, 1766-71) which has a significant impact on the cost of goods of the ADC. In addition, it has been known that ADCs obtained by conjugation to cysteine side chains often display limited stability in circulation, leading to premature disconnection of the cytotoxic payload before the tumor site is reached (Junutula, J. R., et al 2008, Nat. Biotechnol. 26, 925-32).

The disulfide bond structures of the four subclasses of IgG antibodies were known in the 1960s (Milstein C. Biochem J 1966, 101:338-351; Pink J R, Milstein C. Nature 1967, 214:92-94; Frangione B, Milstein C. Nature 1967, 216:939-941; Pink J R, Milstein C. Nature 1967, 216:941-942; Frangione B, et al. Biochem J 1968, 106, 15-21; Frangione B, Milstein C. J Mol Biol 1968; 33:893-906; Edelman G M, et al. Proc Natl Acad Sci USA 1969; 63:78-85; Frangione B, et al. Nature 196, 221:145-148, Spiegelberg, H. L. et al Biochemistry, 1975, 10, 2157-63). Disulfide bond structure is critical for the structure, stability, and biological functions of IgG molecules. Among the four subclasses of IgG antibodies, $IgG_1$, $IgG_2$, $IgG_3$ and $IgG_4$, each IgG contains a total of 12 intra-chain disulfide bonds; each disulfide bond is associated with an individual IgG domain. The two heavy chains are connected in the hinge region by a variable number of disulfide bonds: 2 for $IgG_1$ and $IgG_4$, 4 for $IgG_2$ and 11 for $IgG_3$. The light chain of the $IgG_1$ is connected to the heavy chain by a disulfide bond between the last cysteine residue of the light chain and the fifth cysteine residue of the heavy chain. But, for $IgG_2$, $IgG_3$ and $IgG_4$, the light chain is linked to the heavy chain by a disulfide bond between the last cysteine residue of the light chain and the third cysteine residue of the heavy chain (Liu, H. and May, K., 2012, mAbs 4, 17-23). On the ranks of the susceptibility of disulfide bonds in human IgG1 antibodies by experimental reduction, differential alkylation, and LC-MS analysis (Liu, H, et al Anal. Chem., 2010, 82, 5219-5226), inter chain disulfide bonds are more susceptible to reduction than intra chain disulfide bonds, and the disulfide bonds between the light chain and heavy chain were more susceptible than disulfide bonds between the two heavy chains. The upper disulfide bond of the two inter heavy chain disulfide bonds was more susceptible than the lower one. Furthermore, disulfide bonds in the CH2 domain were the most susceptible to reduction. Disulfide bonds in VL, CL, VH, and CH1 domains had similar and moderate susceptibility, while disulfide bonds in the CH3 domain were the least susceptible to reduction (Liu, H, et al Anal. Chem., 2010, 82, 5219-5226).

Based on the more susceptibility of inter chain disulfide bonds in human IgG1 antibodies, several institutions and companies adopted the chemically specific conjugation strategy through rebridging reduced interchain disulfide bonds of a native antibody, such as, using bromo or dibromo-maleimides, called next generation maleimides (NGMs) (Schumacher, F. F., et al 2014, Org. Biomol. Chem. 12, 7261-7269; UCL Cancer Inst.), applying bis-alkylating reagents via a three-carbon bridge (Badescu, G., et al., 2014, Bioconjug. Chem. 25, 1124-1136., WO2013/190272, WO2014/064424 for PolyTherics Ltd), with di-substituted heteroaryl bridge (US Pat Appl. 2015/0105539 for Concortis Biosystem), or through di-maleimide as a bridge (WO2014/114207). We have also used bromo maleimide and dibromomaleimide linkers to conjugate both drugs and antibodies for a quite while (WO2014/009774, PCT/IBM2012/053554). However, these above bridge linkers were designed in the way to conjugate only one cytotoxic agent to a pair of disulfide bonds, and therefore at most of time they only produced ADCs at DAR less than 2 (drugs per antibody), due to limited numbers (about only two pairs) of reduced disulfide bonds are more accessible for conjugation.

As one of the major issues for ADCs is the limited numbers or amount of cytotoxic compounds that ultimately reaches the tumor, and the favorable DAR over 3 is much important factor for improvement of ADC therapeutical index (Epenetos, A. A. et al, Cancer Res., 1986, 46, 3183-3191; Chari, R. V. Acc. Chem. Res., 2008, 41, 98-107, Zhao, R. Y. et al, 2011, J. Med. Chem. 54, 3606-3623), we therefore disclose novel disulfide bridge linkers of this invention that are able to conjugate two or more drugs per linker for achieving higher DARs (≥4) via re-bridging the susceptible a pair of thiols on the inter chain of IgG antibody that are reduced by TCEP and DTT. And the other reduced disulfide bonds that are inaccessibly reached by the bridge linkers, due to the big size of bridge linker containing two cytotoxic agents, can be recoupled (regenerated) by an oxide, e.g. dehydroascorbic acid (DHAA) or Cu (II), at the end of conjugation. In a word, these bridge linkers of the invention can make homogeneous production of specific ADCs in a simple way.

SUMMARY OF THE INVENTION

The present invention provides linkers containing a hydrazine to link two drugs to a cell-binding agent (e.g., an antibody). The preferred formula of the cell-binding molecule-linker-drug conjugates can be represented as:

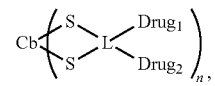

wherein Cb is a cell-binding agent, L is a linker containing a hydrazine group, Drug1 and Drug2 are a drug molecule, n is an integer from 1 to 20, and two S (sulfur) elements from Cb bridgely link to L, which covalently connects two or more drugs (per bridge linker L). The advantages in applying the linker in the cell molecule-drug conjugate are: a). Retaining the stability of the conjugates by covalently cross-linking (re-bridging) the pairs of reduced disulfur bonds of the cell-binding agents, particularly of antibodies; b). Enabling conjugation of the cytotoxic agents/drugs to specific sites of a cell-binding molecule, e.g. the inter chain sites of IgG antibodies, resulting in homogeneous production of ADC.

In one aspect of the present invention, the linker is represented by Formula (I)

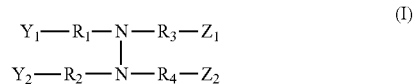

Wherein:

$Y_1$ and $Y_2$ are the same or different a functional group that enables reaction with a pair of sulfur atoms of a cell-binding agent; $Y_1$ and $Y_2$ can react to a pair of sulfur atoms to form disulfide, thioether, or thioester bonds. The preferred function groups for $Y_1$ and $Y_2$ are, but not limited to, an N-hydroxysuccinimide ester, maleimide, disulfide, haloacetyl, ethenesulfonyl, acyl halide (acid halide), acryl (acryloyl), and/or acid anhydride groups.

$Z_1$ and $Z_2$ are the same or different a function group that enables to react with a cytotoxic drug. The functional group $Z_1$ or $Z_2$ can react to a cytotoxic drug to form a disulfide, ether, ester, thioether, thioester, peptide, hydrazone, carbamate, carbonate, amine (secondary, tertiary, or quaternary), imine, cycloheteroalkyl, heteroaromatic, alkoxime or amide bond;

$R_1$, $R_2$, $R_3$ and $R_4$ are the same or different, and are absent, linear alkyl having from 1-8 carbon atoms, branched or cyclic alkyl having from 3 to 8 carbon atoms, linear, branched or cyclic alkenyl or alkynyl, or 1~8 carbon atoms of esters, ether, amide, or polyethyleneoxy unit of formula $(OCH_2CH_2)_p$, wherein p is an integer from 0 to about 1000, or combination thereof.

Additionally $R_1$, $R_2$, $R_3$ and $R_4$ are respectively a chain of atoms selected from C, N, O, S, Si, and P, preferably having 0~500 atoms, which covalently connects to $Y_1$ or $Y_2$ and $Z_1$ or $Z_2$. The atoms used in forming the $R_1$, $R_2$, $R_3$ and $R_4$ may be combined in all chemically relevant ways, such as forming alkylate, alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

In another aspect, this invention provides a cell-binding agent-drug conjugate of Formula (II), in which the cell-binding agent, Cb, and the drug, Drug1 and Drug2, have reacted at the ends of the bridge linker:

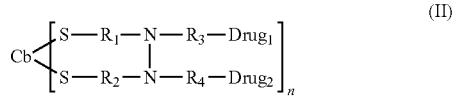

(II)

wherein:

Cb represents a cell-binding agent, preferred an antibody;

Inside the bracket (parentheses) are the linker-drug components that are conjugated to a cell-binding molecule via a pair of thiol atoms. The conjugatable thiol atoms can generally be generated from reduction of pairs of disulfide bonds on the cell-binding molecule with TCEP or DTT reagents.

$Drug_1$ and $Drug_2$ represent the same or different cytotoxic agents, which linked to the cell-binding agent via the bridge linker by a disulfide, thioether, thioester, peptide, hydrazone, ether, ester, carbamate, carbonate, cycloheteroalkyane, heteroaromatic, alkoxime, amide, alkylene, alkenylene, alkynylene or aromatic bond;

n is 1~20; $R_1$, $R_2$, $R_3$ and $R_4$ are described the same previously in Formula (I).

In a further aspect, the present invention provides a modified cell-binding agent of Formula (III), in which the cell-binding agent, Cb, has reacted with the bridge linker, which has $Z_1$ and $Z_2$, the function groups capable of reacting with a drug:

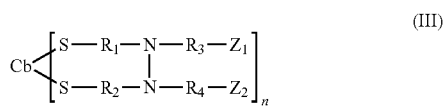

(III)

Wherein Cb, $Z_1$, $Z_2$, $R_1$, $R_2$, $R_3$ and $R_4$ are defined the same as in Formula (I) and (II).

In an even further aspect, the present invention provides a modified drug of Formula (IV), in which the drug, $Drug_1$ and $Drug_2$, have reacted with the linker of Formula (I), which still has $Y_1$ and $Y_2$ group capable of reacting with a pair of sulfur atoms of the cell-binding agent:

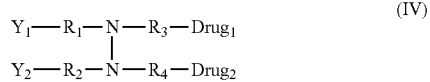

(IV)

Wherein $Y_1$, $Y_2$, $Drug_1$, $Drug_2$, $R_1$, $R_2$, $R_3$ and $R_4$ are defined the same as in Formula (I) and (II).

The present invention further relates to a method of making a cell-binding molecule-drug conjugate of Formula (II), wherein the drugs, $Drug_1$ and $Drug_2$ are linked to a cell-binding agent via the bridge linker.

The present invention also relates to a method of making a modified cell-binding molecule of Formula (III), wherein the cell-binding molecule is reacted with the bridge linker of Formula (I).

The present invention also relates to a method of making a modified drug of formula (IV), wherein the drug is reacted with the bridge linker of Formula (I).

DETAILED DESCRIPTION OF THE INVENTION

Definitions

Figure 1:
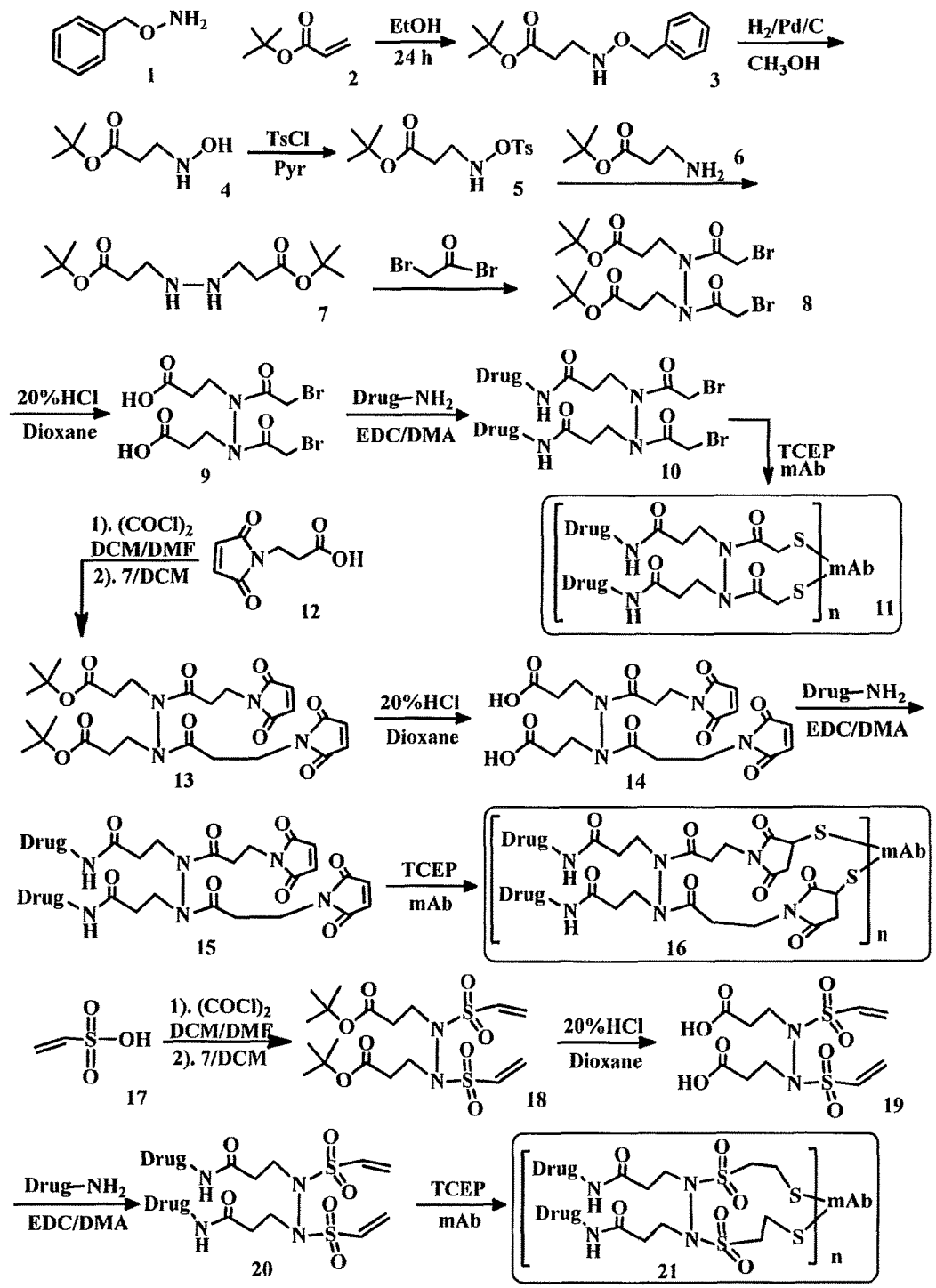
FIG. 1 shows the synthesis of a bridge linker and the application of this linker in the conjugation of an antibody with drugs.
Figure 2:
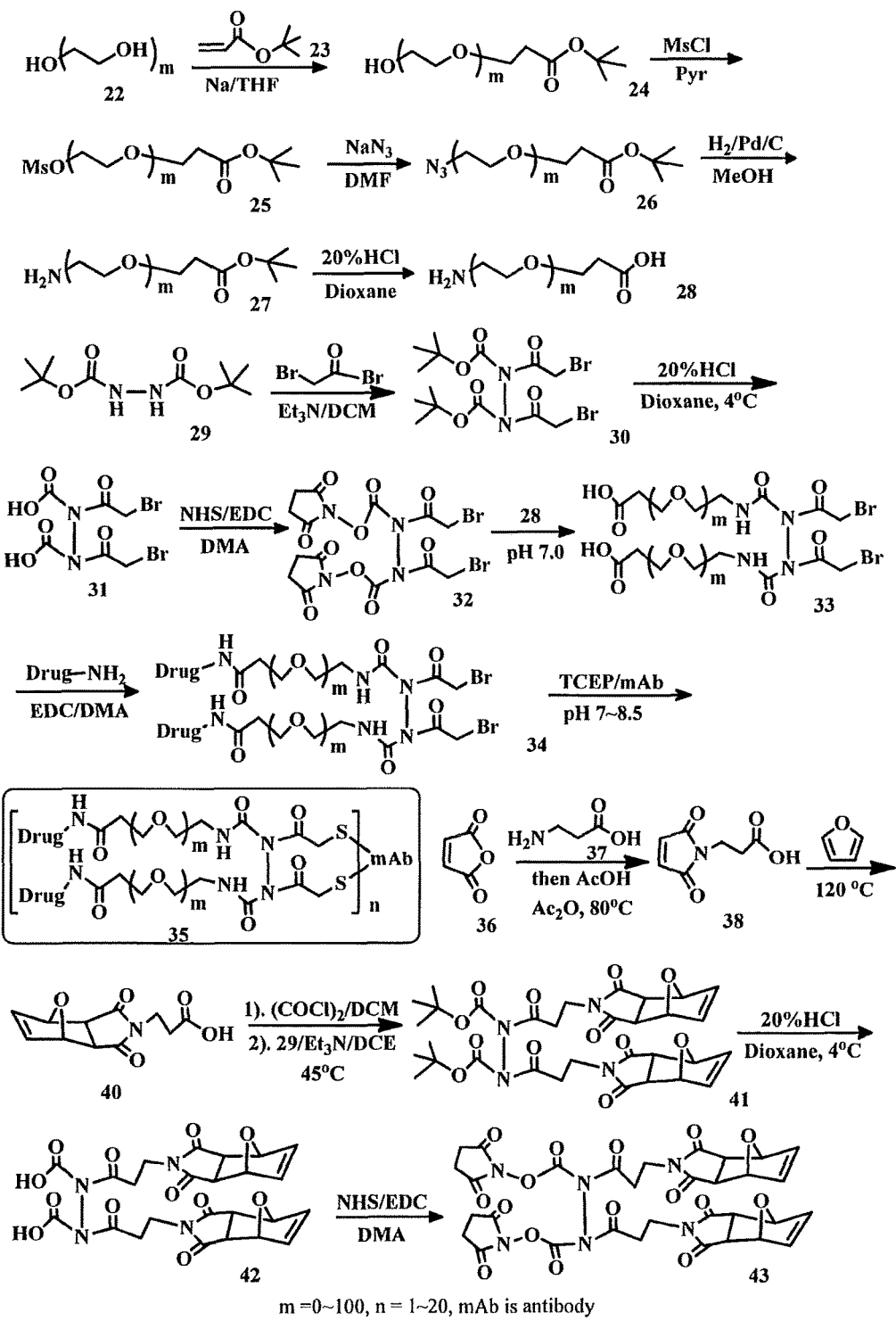
FIG. 2 shows the synthesis of a bridge linker containing polyethylene glycols and the application of this linker in the conjugation of drugs to an antibody via amide and thioether linkage.
Figure 3:
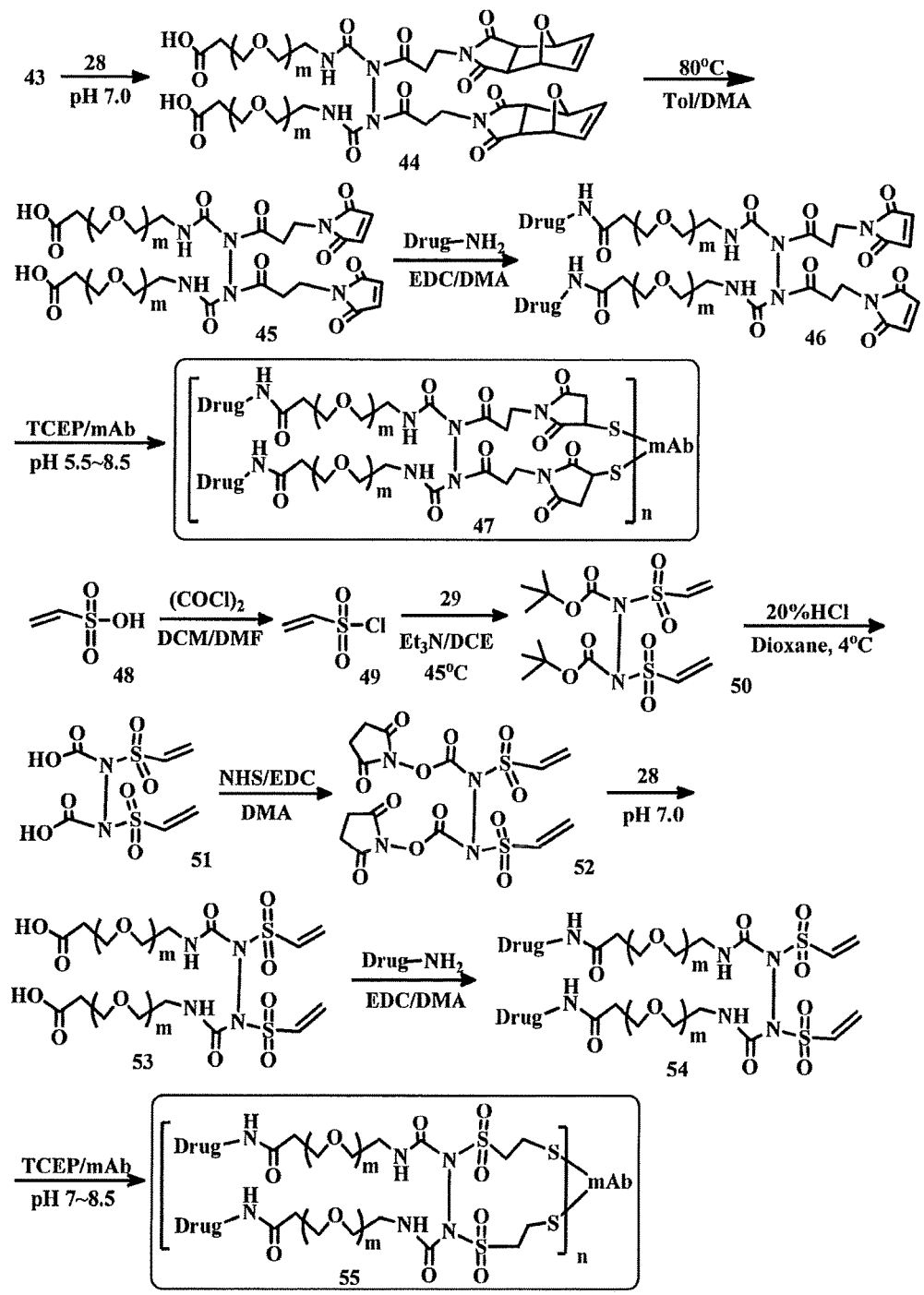
FIG. 3 shows the synthesis of a bridge linker containing polyethylene glycols and the application of this linker in the conjugation of drugs to an antibody via amide and thioether linkage.
Figure 4:
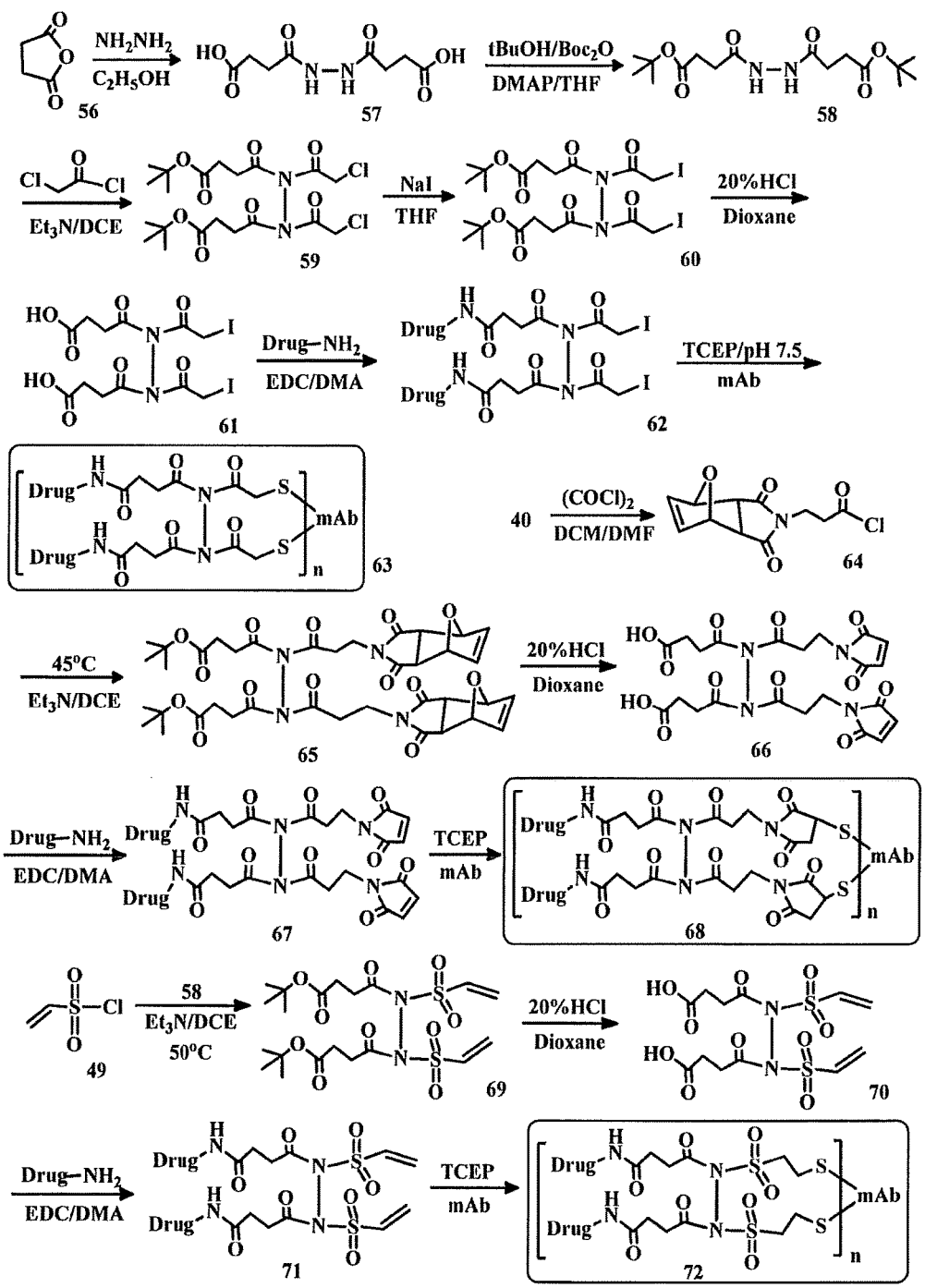
FIG. 4 shows the synthesis of a bridge linker and the application of this linker in the conjugation of drugs to an antibody via amide and thioether linkage.
Figure 5:
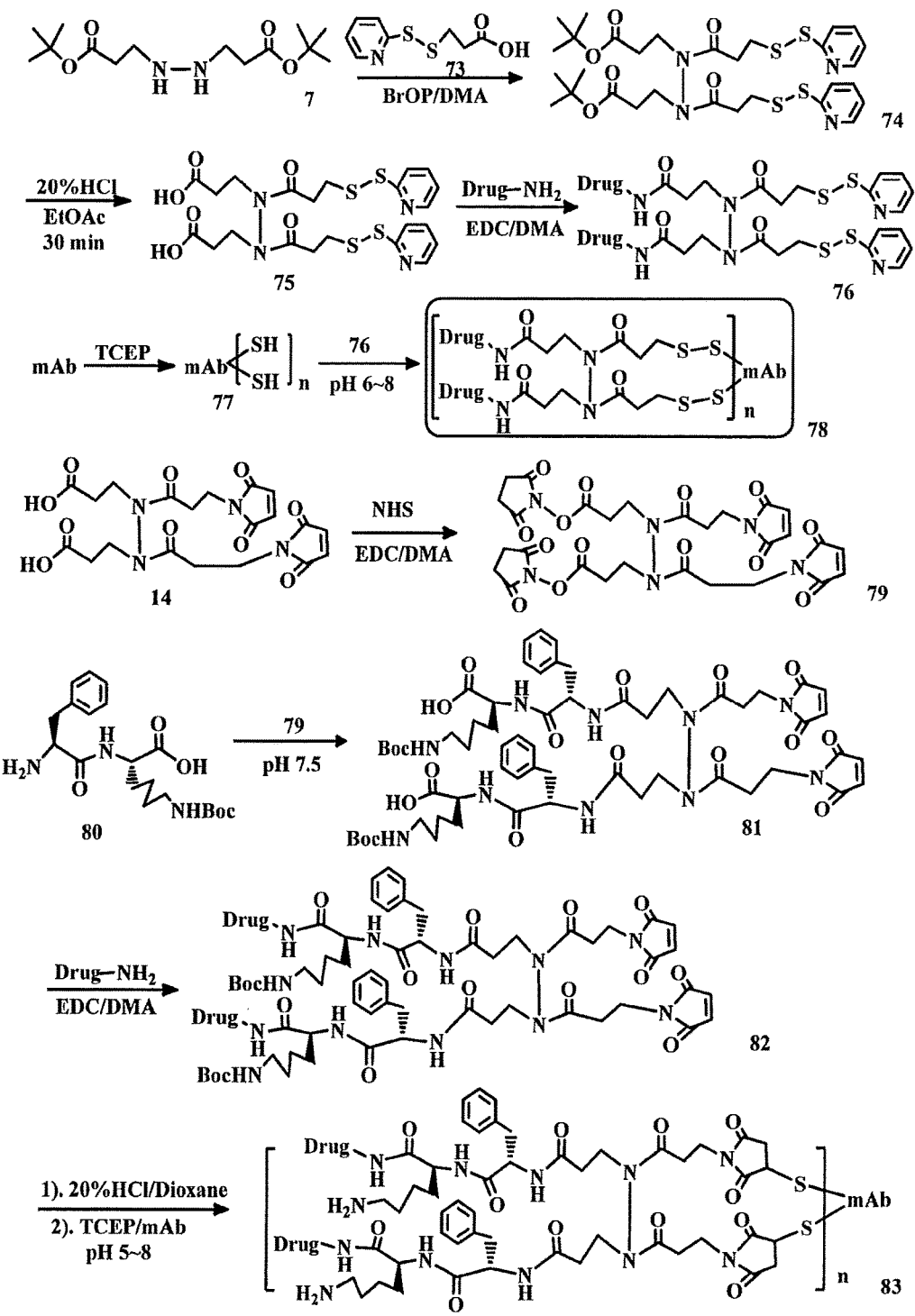
FIG. 5 shows the synthesis of a bridge linker containing peptides and the application of this linker in the conjugation of drugs to an antibody via amide and thioether linkage.
Figure 6:
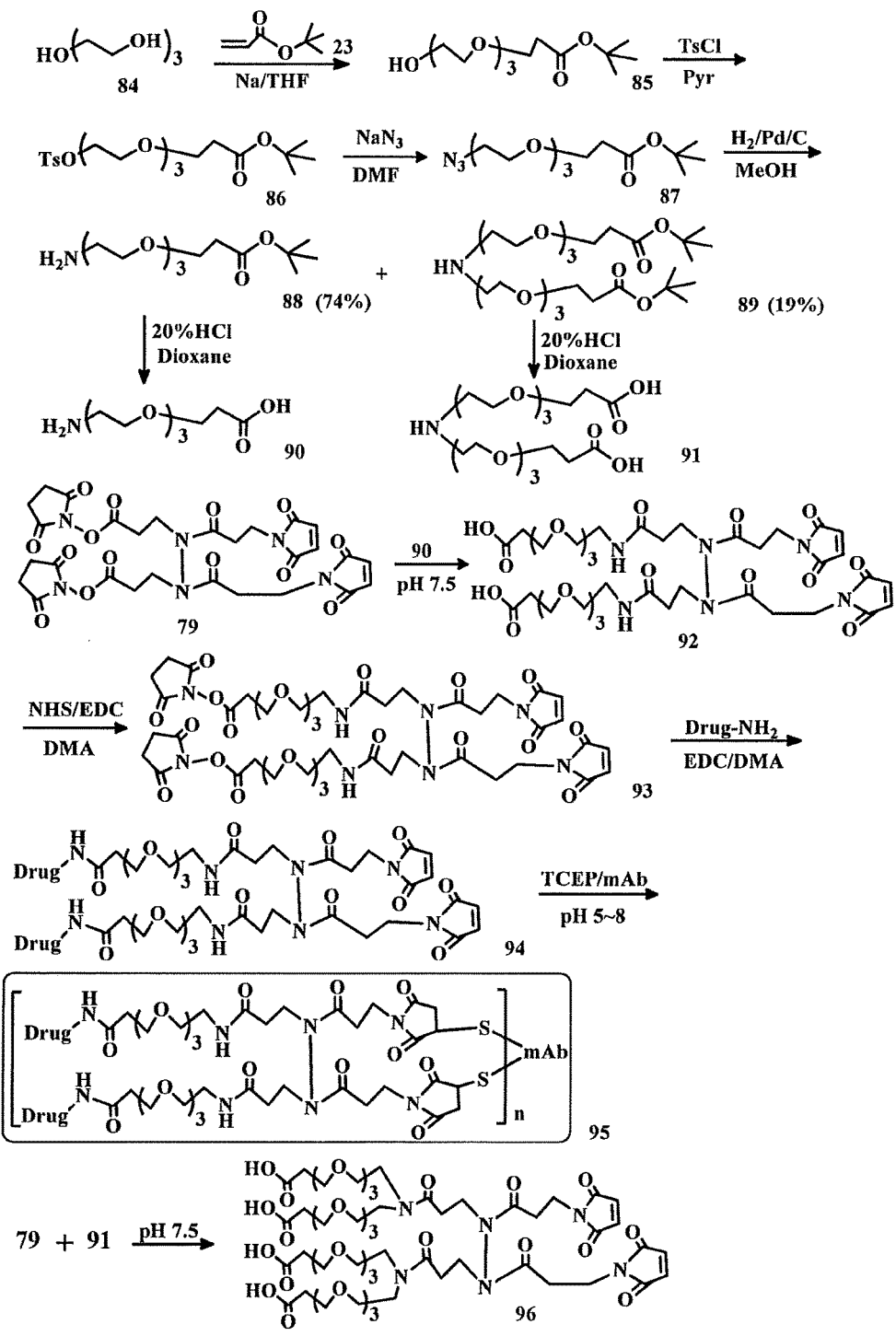
FIG. 6 shows the synthesis of a bridge linker containing polyethylene glycols and the application of this linker in the conjugation of drugs to an antibody via amide and thioether linkage.
Figure 7:
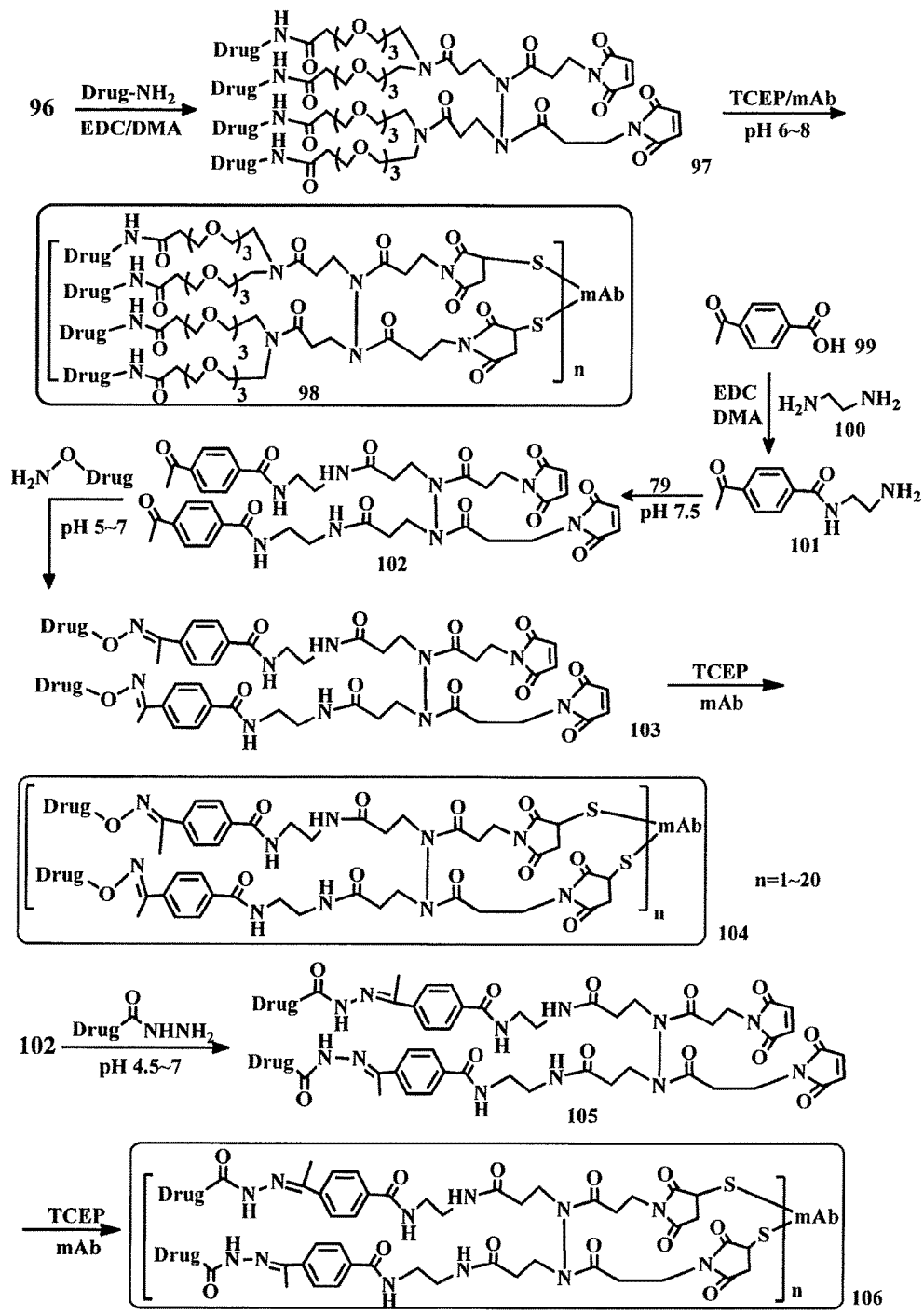
FIG. 7 shows the synthesis of bridge linkers (one containing polyethylene glycols), and the application in the conjugation of two or four drugs per linker to an antibody via amide, oxime or hydrazone linkage to drugs, and thioether linkage to antibodies.
Figure 8:
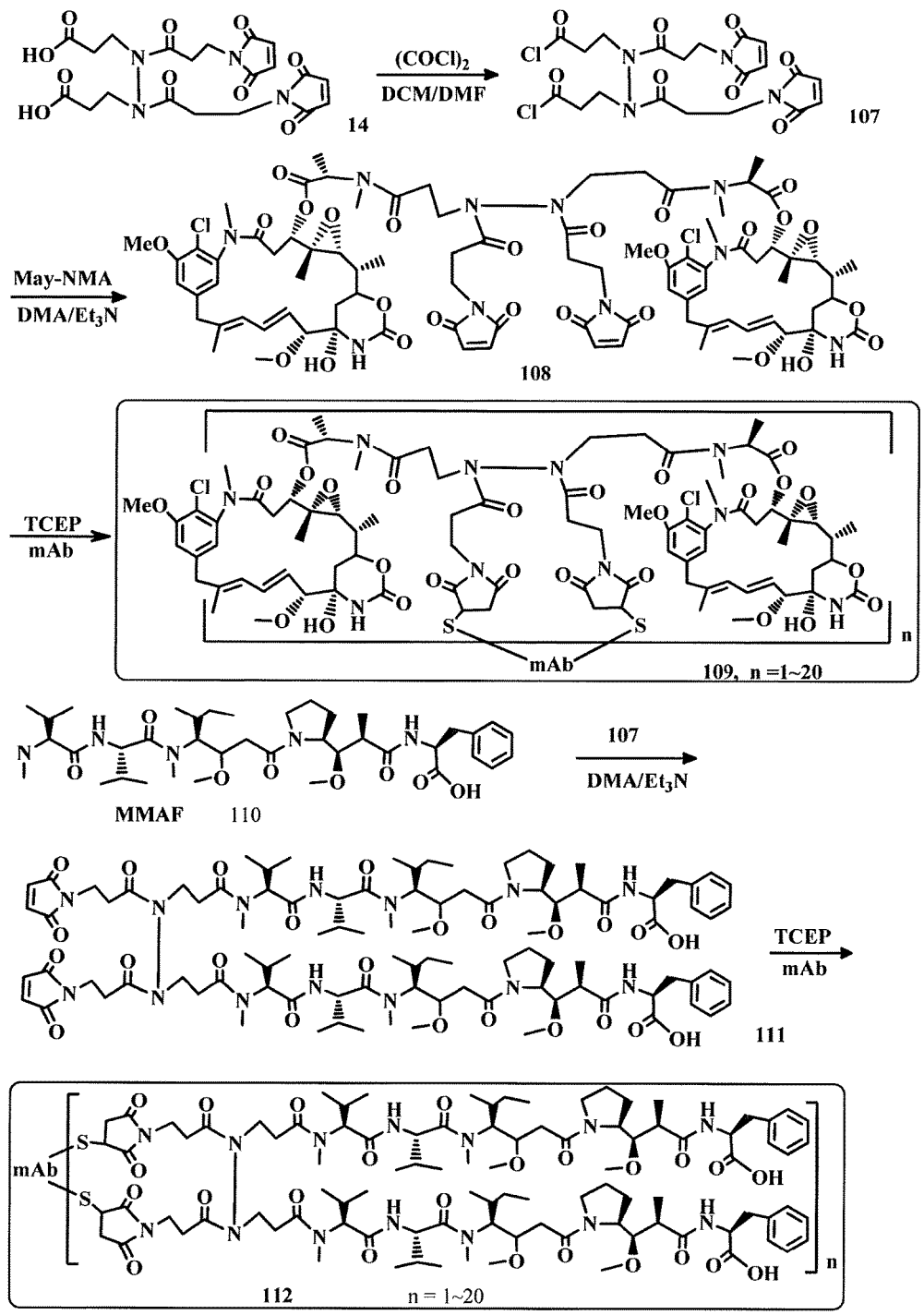
FIG. 8 shows the synthesis of an antibody-maytansinoid conjugate and an antibody-MMAF conjugate via the bridge-linker.
Figure 9:
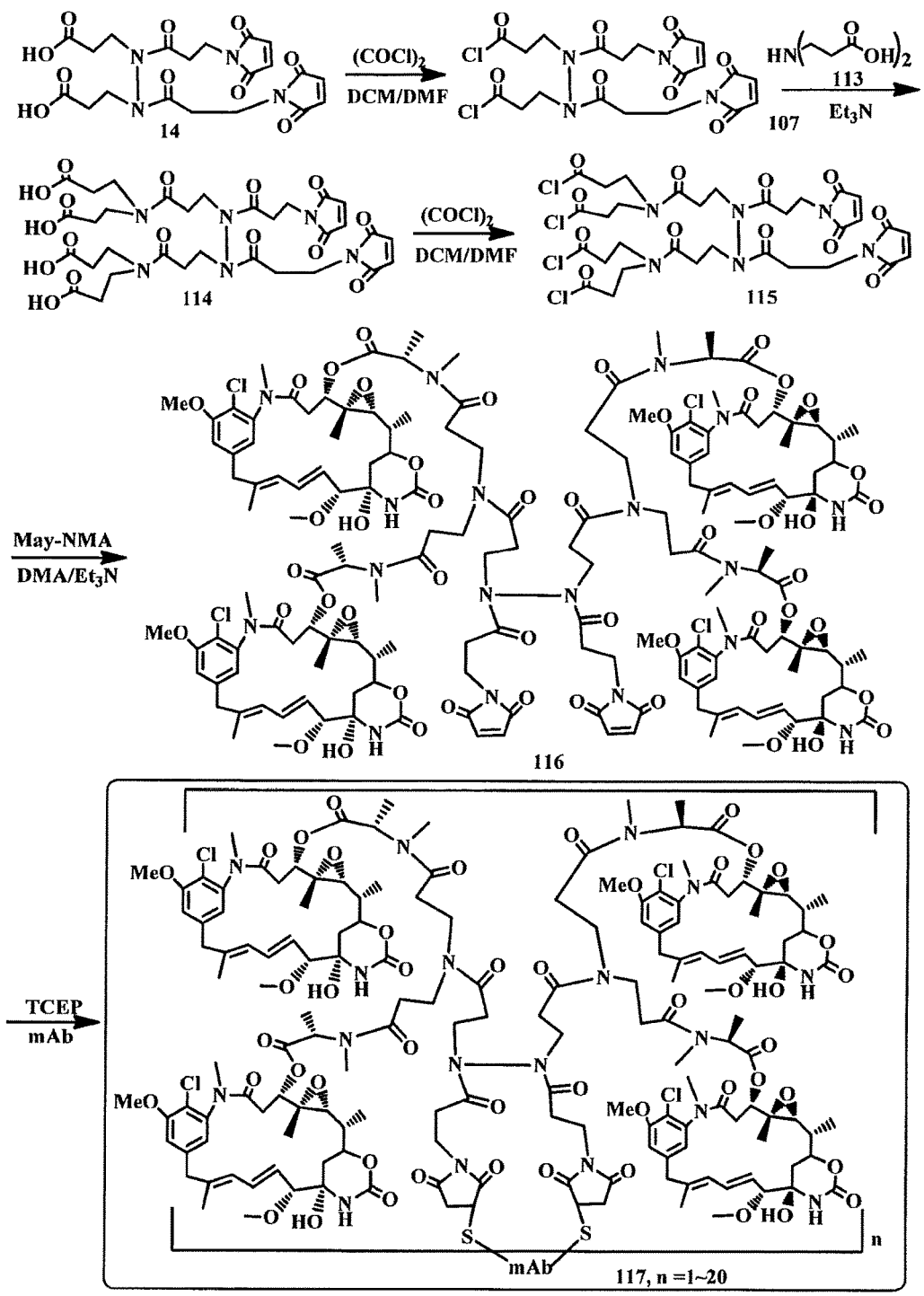
FIG. 9 shows the synthesis an antibody-maytansinoid conjugate via the bridge-linker, wherein four maytansinoids are linked to one bridge linker.
Figure 10:
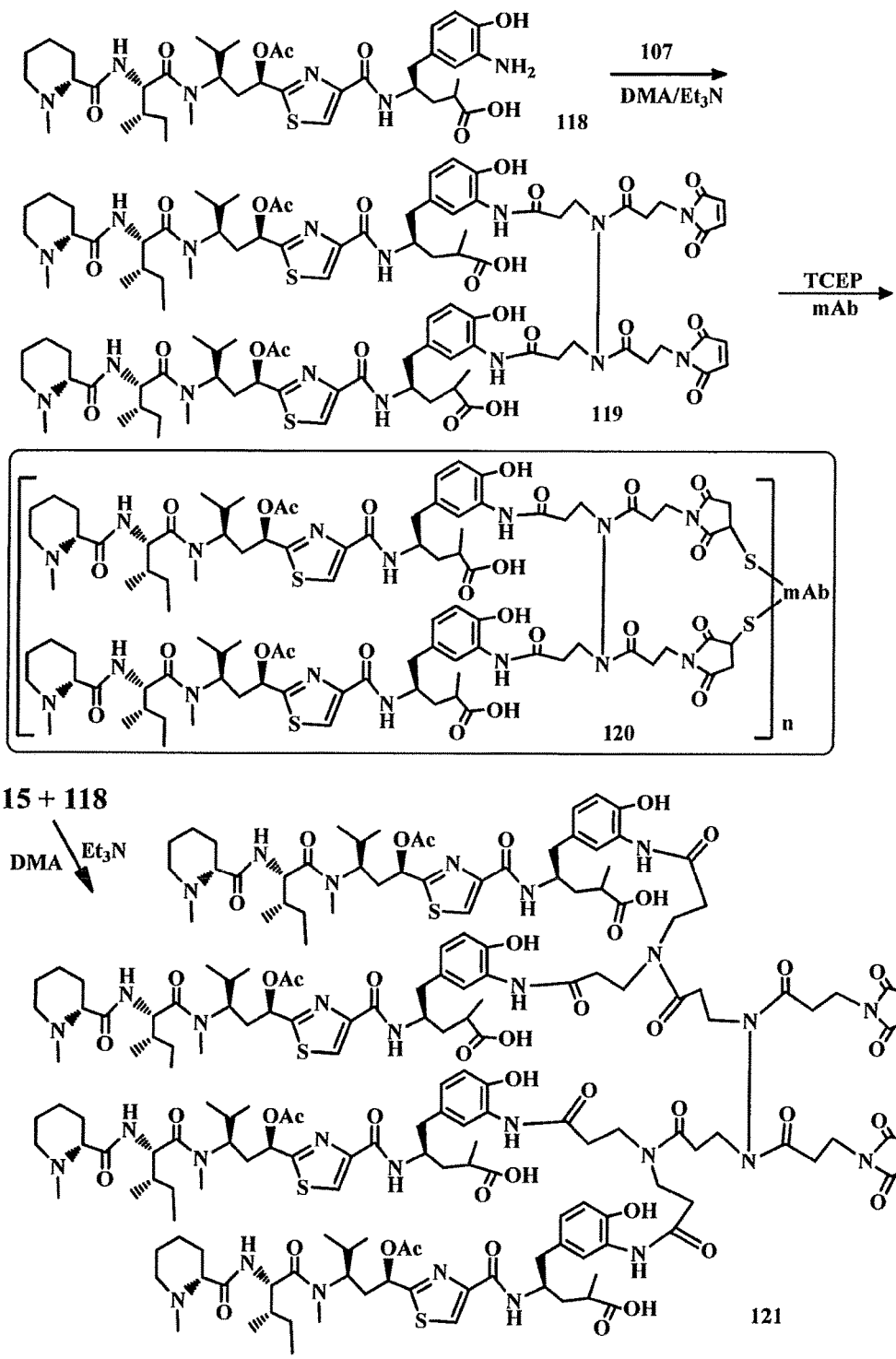
FIG. 10 shows the synthesis of the conjugates of cell-binding molecule-tubulysin analogs via the bridge-linker.
Figure 11:
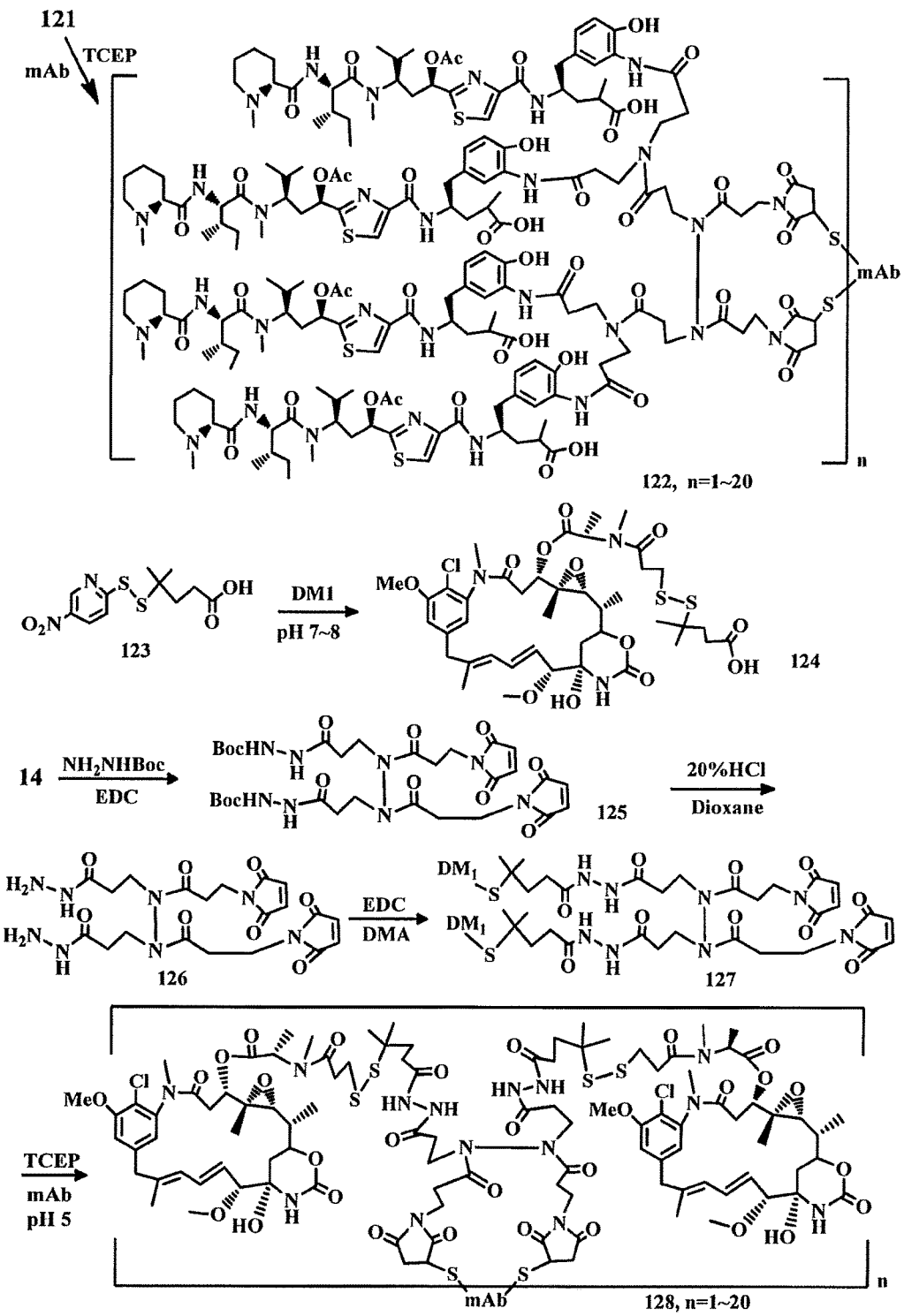
FIG. 11 shows the synthesis of a conjugate containing four tubulysin analogs per bridge linker, and the synthesis of a conjugate of antibody-maytansinoids containing hinder disulfide linkage.

"Alkyl" refers to an aliphatic hydrocarbon group which may be straight or branched having 1 to 8 carbon atoms in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methyl-hexyl, 2,2-dimethylhexyl, 2,4-dimethylhexyl, 2,5-dimethylhexl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)$_2$R', —S(O)R', —OH, -halogen, —N$_3$, —NH$_2$, —NH(R'), —N(R')$_2$ and —CN; where each R' is independently selected from —$C_1$-$C_8$ alkyl and aryl. "Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)X, —OC(O)R', —C(O)OR', —C(O)NH$_2$, —C(O)NHR', —C(O)N(R')$_2$, —NHC(O)R, —SR', —S(O)R', —S)O)$_2$R', —OH, -halogen, —N$_3$, —NH$_2$, —NH(R'), —N(R')$_2$ and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$'), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by O, N, Si, Se, P or S, preferentially by O, S, and N. The term aryl or Ar also refers to an aromatic group, wherein one or several H atoms are replaced independently by —R', -halogen, —OR', or —SR', —NR'R", —N═NR', —N═R', —NR'R", —NO$_2$, —S(O)R', —S(O)$_2$R', —S(O)$_2$OR', —OS(O)$_2$OR', —PR'R", —P(O)R'R", —P(OR')(OR"), —P(O)(OR')(OR") or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference. Preferred nonaromatic heterocyclic include, but are not limited to epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrimidinyl, dihydrothiopyranyl, azepanyl, as well as the fused systems resulting from the condensation with a phenyl group.

The term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazolyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCE, 1,2-dichloroethane; DCM, dichloromethane; DIAD, diisopropylazodicarboxylate; DIBAL-H, diisobutylaluminium hydride; DIPEA, diisopropylethylamine; DEPC, diethyl phosphorocyanidate; DMA, N,N-dimethyl acetamide; DMAP, 4-(N, N-dimethylamino)pyridine; DMF, N,N-dimethyl-formamide; DMSO, dimethylsulfoxide; DTT, dithiothreitol; EDC, 1-(3-dimethylamino-propyl)-3-ethylcarbodiimide hydrochloride; ESI-MS, electrospray mass spectrometry; HATU, O-(7-azabenzotriazol-1-yl)-N, N, N',N'-tetramethyluronium hexafluorophosphate; HOBt, 1-hydroxybenzotriazole; HPLC, high pressure liquid chromatography; NHS, N-Hydroxysuccinimide; MMP, 4-methylmorpholine; PAB, p-aminobenzyl; PBS, phosphate-buffered saline (pH 7.0~7.5); PEG, polyethylene glycol; SEC, size-exclusion chromatography; TCEP, tris(2-carboxyethyl) phosphine; TFA, trifluoroacetic acid; THF, tetrahydrofuran; Val, valine.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, the disclosure of which is hereby incorporated by reference.

The novel conjugates disclosed herein use the bridge linkers. Examples of some suitable linkers and their synthesis are shown in FIGS. 1 to 11.

The Bridge Linkers

The synthetic routes to produce bridge linkers as well as the preparation of the conjugates of drugs to a cell binding molecules of the present invention are shown in FIGS. 1~11. The bridge linkers possess three elements: a) Two groups, are the same or independently, such as but not limited to, N-hydroxysuccinimide ester, maleimide, disulfide, haloacetyl, ethenesulfonyl, acyl halide (acid halide), acryl (acryloyl), and/or acid anhydride groups, capable of reaction with a pair of thiol atoms on a cell-binding agent; b) The middle bridge is hydrazine, linked to the function groups; and c) Two groups, are the same or independently, such as but not limited to, a disulfide, maleimide, haloacetyl, aldehyde, ketone, azide, amine, alkoxyamine and hydrazide, capable of reaction with a drug. The bridge linkers containing hydrazine can be introduced by direct condensation of hydrazine with an acid, an acid halide or acid anhydride, following by introduction of the function groups capable of reaction with a cell-binding agent and drugs. The synthesis of these bridge linkers is exampled in the FIGS. 1~11 and in the experimental section.

Preferably, the bridge linkers are compounds of the Formula (I) below:

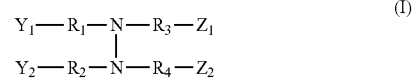

Wherein:

Y$_1$ and Y$_2$ are the same or different a functional group that enables reaction with a pair of sulfur atoms of a cell-binding agent, to form disulfide, thioether, or thioester bonds. The preferred function groups for Y$_1$ and Y$_2$ are, but not limited to, a N-hydroxysuccinimide ester, maleimide, disulfide, haloacetyl, acyl halide (acid halide), ethenesulfonyl, acryl (acryloyl), 2-(tosyloxy)acetyl, 2-(mesyloxy)acetyl, 2-(nitrophenoxy)acetyl, 2-(dinitrophenoxy)acetyl, 2-(fluorophenoxy)-acetyl, 2-(difluorophenoxy)-acetyl, 2-(pentafluorophenoxy)acetyl, 2-(((trifluoromethyl)-sulfonyl)oxy)acetyl, and/or acid anhydride groups, as the structures displayed below:

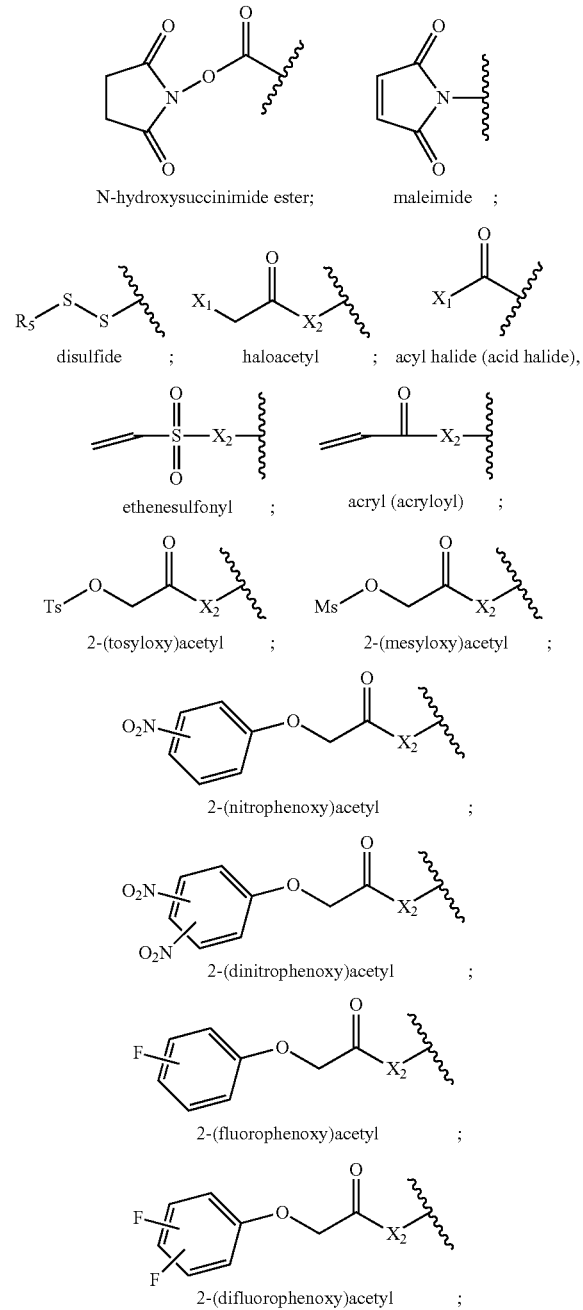

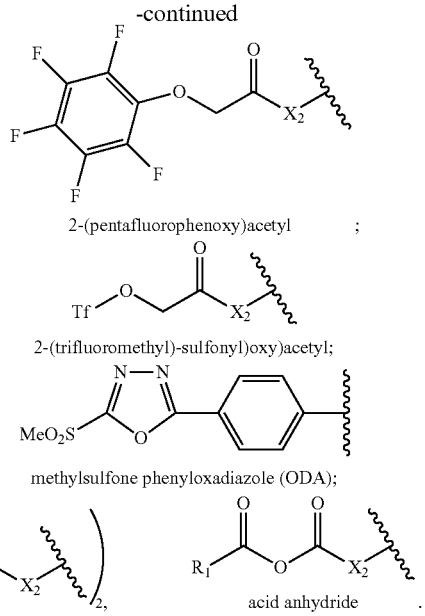

Wherein X$_1$ is F, Cl, Br, I or Lv; X$_2$ is O, NH, N(R$_1$), or CH$_2$; R$_5$ is R$_1$; aromatic, heteroaromatic, or aromatic group wherein one or several H atoms are replaced independently by —R$_1$, -halogen, —OR', —SR$_1$, —NR$_1$R$_2$, —NO$_2$, —S(O)R$_1$, —S(O)$_2$R$_1$, or —COOR$_1$; Lv is a leaving group selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or a intermediate molecule generated with a condensation reagent for peptide coupling reactions, or for Mitsunobu reactions.

Z$_1$ and Z$_2$ are the same or different a function group that enables to react with a cytotoxic drug. The functional group Z$_1$ or Z$_2$ can react to a cytotoxic drug to form a disulfide, ether, ester, thioether, thioester, peptide, hydrazone, carbamate, carbonate, amine (secondary, tertiary, or quaternary), imine, cycloheteroalkyane, heteroaromatic, alkoxime or amide bond;

R$_1$, R$_2$, R$_3$ and R$_4$ are the same or different, and are absent, linear alkyl having from 1~8 carbon atoms, branched or cyclic alkyl having from 3 to 8 carbon atoms, linear, branched or cyclic alkenyl or alkynyl, or 1~8 carbon atoms of esters, ether, amide, or polyethyleneoxy unit of formula (OCH$_2$CH$_2$)$_p$, wherein p is an integer from 0 to about 1000, or combination thereof.

Additionally R$_1$, R$_2$, R$_3$ and R$_4$ are respectively a chain of atoms selected from C, N, O, S, Si, and P, preferably having 0~500 atoms, which covalently connects to Y$_1$ or Y$_2$ and Z$_1$ or Z$_2$. The atoms used in forming the R$_1$, R$_2$, R$_3$ and R$_4$ may be combined in all chemically relevant ways, such as forming alkylate, alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

Examples of the functional group, Z$_1$ and Z$_2$, which enable linkage of a cytotoxic drug, include groups that enable linkage via a disulfide, thioether, thioester, peptide, hydrazone, ester, carbamate, carbonate, alkoxime or an amide bond. Such functional groups include, but are not limited to, thiol, disulfide, amino, carboxy, aldehydes, ketone, maleimido, haloacetyl, hydrazines, alkoxyamino, and/or hydroxy.

Examples of the functional group, $Z_1$ and $Z_2$, that enable reaction with the terminal of amine of a drug/cytotoxic agent can be, but not limited to, N-hydroxysuccinimide esters; p-nitrophenyl esters; dinitrophenyl esters; pentafluorophenyl esters; or esters formed with tetrafluorophenol, difluorophenol, monofluorophenol, pentachlorophenol, triflate, imidazole, dichlorophenol, tetrachlorophenol, 1-hydroxybenzotriazole, tosylate, mesylate, 2-ethyl-5-phenylisoxazolium-3'-sulfonate; or an anhydride formed with, e.g. acetyl anhydride, formyl anhydride; or a intermediate molecule generated with a condensation reagent for peptide coupling reactions, or for Mitsunobu reactions. With the terminal of thiol can be, as but not limited to, pyridyldisulfides; nitropyridyldisulfides; maleimides; haloacetates and carboxylic acid chlorides. With the terminal of ketone or aldehyde can be, as but not limited to, amines; alkoxyamines; hydrazines; or acyloxylamine; With the terminal of azide can be, as but not limited to, alkyne.

In preferred embodiments, the functional groups, $Z_1$ and $Z_2$, react to Drug1 and Drug2 through condensation of an acid and an amine to form an amide bond. The condensation reagents are, but not limited: EDC (N-(3-Dimethylaminopropyl)-N'-ethylcarbodiimide), DCC (Dicyclohexyl-carbodiimide), N,N'-Diisopropylcarbodiimide (DIC), N-Cyclohexyl-N'-(2-morpholinoethyl)carbodiimide metho-p-toluenesulfonate (CMC,or CME-CDI), 1,1'-Carbonyldiimidazole (CDI), TBTU (O-(Benzotriazol-1-yl)-N,N,N',N'-tetramethyluronium tetrafluoroborate), N,N,N',N'-Tetramethyl-O-(1H-benzotriazol-1-yl)uronium hexafluorophosphate (HBTU), (Benzotriazol-1-yloxy)tris (dimethylamino)phosphonium hexafluorophosphate (BOP), (Benzotriazol-1-yloxy)tripyrrolidinophosphonium hexafluorophosphate (PyBOP), Diethyl cyanophosphonate (DEPC), Chloro-N,N,N',N'-tetramethylformamidinium hexafluorophosphate, 1-[Bis(dimethylamino)methylene]-1H-1,2,3-triazolo[4,5-b]pyridinium 3-oxid hexafluorophosphate (HATU), 1-[(Dimethylamino)(morpholino) methylene]-1H-[1,2,3]triazolo[4,5-b]pyridine-1-ium 3-oxide hexafluorophosphate (HDMA), 2-Chloro-1,3-dimethylimidazolidinium hexafluorophosphate (CIP), Chlorotripyrrolidinophosphonium hexafluorophosphate (PyCloP), Fluoro-N,N,N',N'-bis(tetra-methylene)formamidinium hexafluorophosphate (BTFFH), N,N,N',N'-Tetramethyl-S-(1-oxido-2-pyridyethiuronium hexafluorophosphate, O-(2-Oxo-1(2H)pyridyl)-N,N,N',N'-tetramethyluronium tetrafluoroborate (TPTU), S-(1-Oxido-2-pyridyl)-N,N,N'N-tetramethylthiuronium tetrafluoroborate, O-[(Ethoxycarbonyl) cyano-methylenamino]-N,N,N',N'-tetramethyluronium hexafluorophosphate (HOTU), (1-Cyano-2-ethoxy-2-oxoethylidenaminooxy) dimethylaminomorpholinocarbenium hexafluorophosphate (CO-MU), O-(Benzotriazol-1-yl)-N,N,N',N'-bis(tetramethylene)uronium hexafluoro-phosphate (HBPyU), N-Benzyl-N'-cyclohexylcarbodiimide (with, or without polymer-bound), Dipyrrolidino(N-succinimidyloxy)carbenium hexafluorophosphate (HSPyU), Chlorodipyrrolidinocarbenium hexafluorophosphate (PyClU), 2-Chloro-1,3-dimethylimidazolidinium tetrafluoroborate(CIB), (Benzotriazol-1-yloxy) dipiperidinocarbenium hexafluorophosphate (HB-PipU), O-(6-Chlorobenzotriazol-1-yl)-N,N,N',N'-tetramethyl-uronium tetrafluoroborate (TCTU), Bromotris (dimethylamino)-phosphonium hexafluoro-phosphate (BroP), Propylphosphonic anhydride (PPACA, T3P), 2-Morpholinoethyl isocyanide (MEI), N,N,N',N'-Tetramethyl-O—(N-succinimidyl)uronium hexafluoro-phosphate (HSTU), 2-Bromo-1-ethyl-pyridinium tetrafluoroborate (BEP), O-[(Ethoxycarbonyecyanomethylenamino]-N,N,N',N'-tetramethyluronium tetrafluoroborate (TOTU), 4-(4,6-Dimethoxy-1,3,5-triazin-2-yl)-4-methylmorpholinium chloride (MMTM, DMTMM), N,N,N',N'-Tetramethyl-O—(N-succinimidyl)uronium tetrafluoroborate (TSTU), O-(3,4-Dihydro-4-oxo-1,2,3-benzotriazin-3-yl)-N,N,N',N'-tetramethyluronium tetrafluoroborate (TDBTU), 1,1'-(Azodicarbonyl)dipiperidine (ADD), Di-(4-chlorobenzyl) azodicarboxylate (DCAD), Di-tert-butyl azodicarboxylate (DBAD), Diisopropyl azodicarboxylate (DIAD), Diethyl azodicarboxylate (DEAD).

In preferred embodiments, $R_1$, $R_2$, $R_3$, and $R_4$, are linear alkyl having from 1-8 carbon atoms, or containing dipeptides, or tripeptides, or polyethyleneoxy unit of formula $(OCH_2CH_2)_p$, p=1~100. In addition, $R_1$, $R_2$, $R_3$, and $R_4$ can be cleavable by a protease.

The detail examples of the synthesis of the bridge linkers are shown in the FIGS. 1~11. Normally the bridge substituent of hydrazine can be condensated with linker components $R_1$, $R_2$, $R_3$, and $R_4$ containing function groups capable to react to drug compounds and thiol molecules.

Cell-Binding Agent-Drug Conjugates

The conjugates of the present invention can be represented by the following formula,

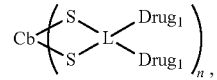

wherein Cb is a cell-binding agent, L is a linker, Drug1 and Drug2 are a drug molecule, n is an integer from 1 to 20, and two S (sulfur) elements from Cb bridgely link to L, which covalently connects two or more drugs (per bridge linker L).

The bridge linker L may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), 4-thiopentanoate ("SPP"), 4-(N-maleimidomethyl)-cyclohexane-1 carboxylate ("MCC"), (4-acetyl)aminobenzoate ("SIAB"), 4-thio-butyrate (SPDB), 4-thio-2-hydroxysulfonyl-butyrate (2-Sulfo-SPDB), ethyleneoxy —$CH_2CH_2O$— as one or more repeating units ("EO" or "PEO"). Additional linker components are known in the art and some are described herein.

Example structures of these components containing linkers are:

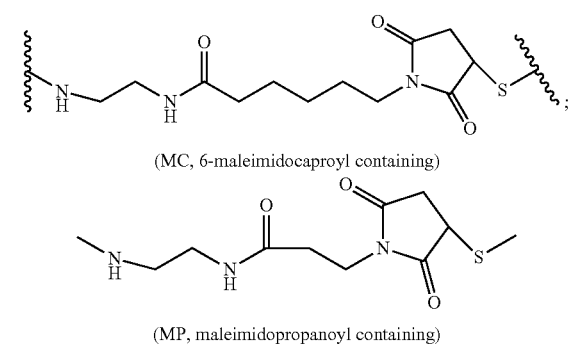

(MC, 6-maleimidocaproyl containing)

(MP, maleimidopropanoyl containing)

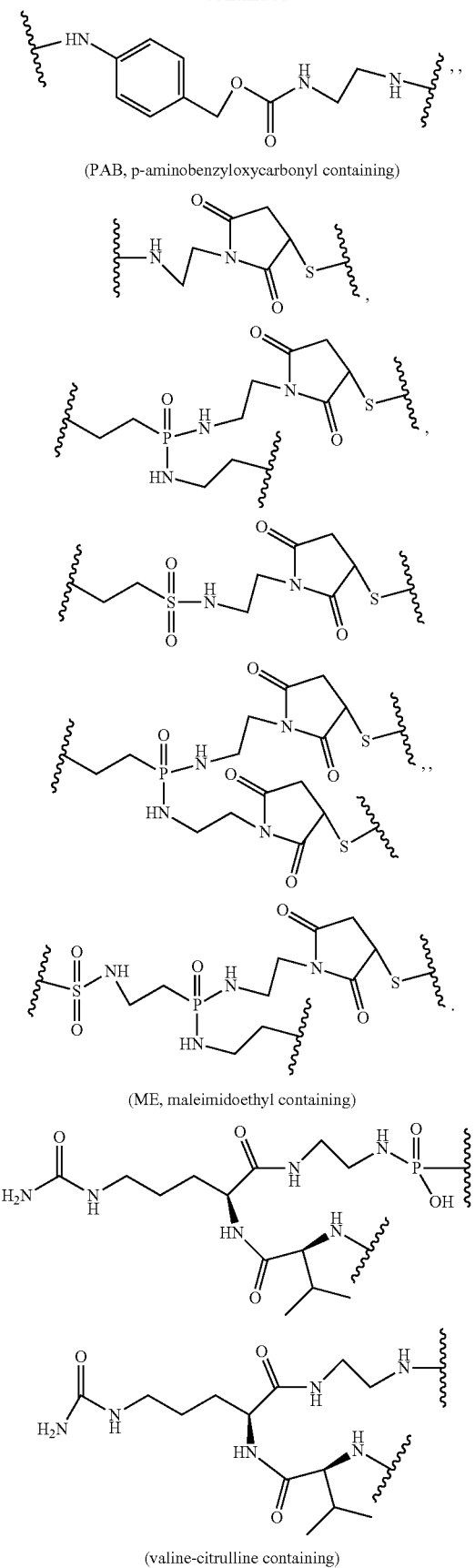

(PAB, p-aminobenzyloxycarbonyl containing)

(ME, maleimidoethyl containing)

(valine-citrulline containing)

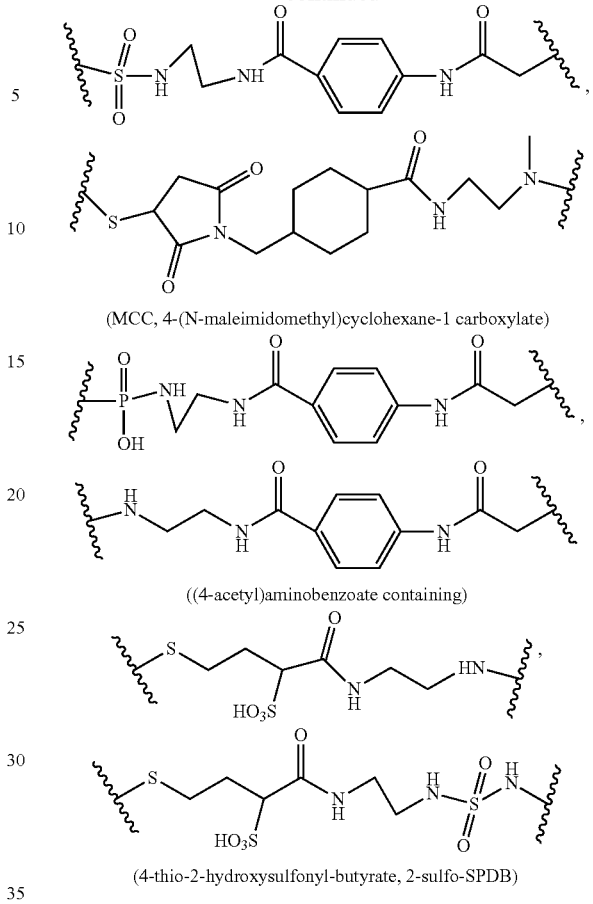

(MCC, 4-(N-maleimidomethyl)cyclohexane-1 carboxylate)

((4-acetyl)aminobenzoate containing)

(4-thio-2-hydroxysulfonyl-butyrate, 2-sulfo-SPDB)

Preferably, the conjugates have the following Formula (II):

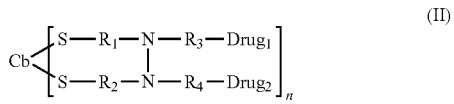

(II)

wherein:

Cb represents a cell-binding agent, preferably an antibody;

Drug$_1$ and Drug$_2$ represent the same or different drugs/cytotoxic agents, linked to the cell-binding agent via the bridge linker through an alkyl, alkylene, alkenylene, alkynylene, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime bond, or combination thereof.

Inside the bracket (parentheses) are the linker-drug components that are conjugated to a cell-binding molecule via a pair of thiol atoms. The conjugatable thiol atoms can generally be generated from reduction of pairs of disulfide bonds on the cell-binding molecule with TCEP or DTT reagents.

n is 1~20; R$_1$, R$_2$, R$_3$ and R$_4$ are described the same previously in Formula (I).

As described in more detail below, Drug$_1$ and Drug$_2$ can be any of many small molecule drugs, including, but not limited to, tubulysins, calicheamicins, auristatins, maytansinoids, CC-1065 analogs, morpholinos doxorubicins, taxanes, cryptophycins, epothilones, and benzodiazepine dimers (e.g., dimmers of pyrrolobenzodiazepine (PBD) or tomaymycin), indolinobenzodiazepines, imidazobenzothiadiazepines, or oxazolidinobenzodiazepines).

To synthesize the conjugate, the cell-binding agent can be first modified with the bridge linkers of the present invention through reduction of disulfide bonds of the cell-binding molecule. The yielded a pair of free thiols can react to the bridge linker of Formula (I) at pH 5~9 aqueous media with or without addition of 0~30% of water mixable (miscible) organic solvents, such as DMA, DMF, ethanol, methanol, acetone, acetonitrile, THF, isopropanol, dioxane, propylene glycol, or ethylene diol, to introduce the reactive groups of $Z_1$ and $Z_2$, whose reactive groups can be a disulfide, maleimido, haloacetyl, azide, 1-yne, ketone, aldehyde, alkoxyamino, or hydrazide. Then the reactive group of a cytotoxic agent reacts to the modified cell-binding molecule accordingly. For example, synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl or ethylsulfonyl modified cell-binding agent and a drug containing a free thiol group. Synthesis of conjugates bearing an acid labile hydrazone can be achieved by reaction of a carbonyl group with the hydrazide moiety in the linker, by methods known in the art (see, for example, P. Hamann et al., Hinman, L. M., et al, Cancer Res. 53, 3336-334, 1993; B. Laguzza et al., J. Med. Chem., 32; 548-555, 1959; P. Trail et al., Cancer Res., 57; 100-105, 1997). Synthesis of conjugates bearing triazole linkage can be achieved by reaction of a 1-yne group of the drug with the azido moiety in the linker, through the click chemistry (Huisgen cycloaddition) (Lutz, J-F. et al, 2008, Adv. Drug Del. Rev. 60, 958-970; Sletten, E. M. et al 2011, Acc Chem. Research 44, 666-676).

Alternatively, the drug can react with the bridge linkers of the present invention that have conjugated to a cell-binding molecule to give a modified cell-binding molecule linker of Formula (III) bearing functionalities. For example, a thiol-containing drug can react with the modified cell-binding molecule bridge linker of Formula (III) bearing a maleimdo, or a haloacetyl, or an ethylsulfonyl substituent at pH 5.0~9.0 in aqueous buffer to give a cell-binding molecule-drug conjugate via a thioether linkage. A thiol-containing drug can undergo disulfide exchange with a modified bridge linker of Formula (III) bearing a pyridyldithio moiety to give a conjugate a disulfide bond linkage. A drug bearing a hydroxyl group or a thiol group can be reacted with a modified bridge linker of Formula (III) bearing a halogen, particularly the alpha halide of carboxylates, in the presence of a mild base, e.g. pH 7.5~9.5, to give a modified drug bearing an ether or thiol ether link. A hydroxyl group containing drug can be condensed with a bridge cross linker of Formula (I) bearing a carboxyl group, in the presence of a dehydrating agent, such as EDC or DCC, to give ester linkage, then the subject drug modified bridge linker undergoes the conjugation with a cell-binding molecule. A drug containing an amino group can condensate with a carboxyl ester of NHS, imidazole, nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate on the cell-bind-ing molecule-bridge linker of Formula (III) to give a conjugate via amide bond linkage.

The conjugate may be purified by standard biochemical means, such as gel filtration on a Sephadex G25 or Sephacryl S300 column, adsorption chromatography, and ion exchange or by dialysis. In some cases, a small molecule as a cell-binding agent (e.g. folic acid, melanocyte stimulating hormone, EGF etc) conjugated with a small molecular drugs can be purified by chromatography such as by HPLC, medium pressure column chromatography or ion exchange chromatography.

Modified Cell-Binding Agents/Molecules

The Cell-Binding Agent Modified by Reaction with Linkers of the Present Invention are Preferably Represented By by the Formula (III)

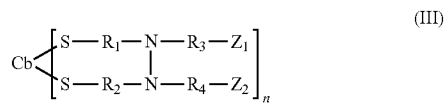

Wherein Cb, $Z_1$, $Z_2$, n, $R_1$, $R_2$, $R_3$ and $R_4$ are defined the same as in Formula (I) and (II).

In preferred embodiments, $Z_1$ and $Z_2$ are a disulfide substituent, maleimido, haloacetyl, alkoxyamine, azido, ketone, aldehyde, hydrazine group, an N-hydroxysuccinimide ester, or a carboxyl ester formed with phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate. $Z_1$ and $Z_2$ can then react with a cytotoxic agent through thioether, hydrazone, amide, alkoxime, carbamate, ester, ether or disulfide bond. The modified cell-binding agent can be prepared via a reaction of the cell-binding agent with the bridge linkers of Formula (I) as described in Formula (II) above.

In order to achieve a higher conjugation yield for the reaction of the function groups $Y_1$ and $Y_2$ on the bridge linkers of Formula (I) with a pair of free thiols on the cell-binding molecule, a small percentage of organic co-solvent may be required to add to the reaction mixture, as well added in the solution after the reaction to maintain solubility of the Formula (III) in aqueous solution. To modify the cell-binding agents, the cross-linking reagent (bridge linker) of Formula (I) can be first dissolved in a polar organic solvent, which is miscible with water, for example different alcohols, such as methanol, ethanol, and propanol, acetone, acetonitrile, tetrahydrofuran (THF), 1,4-dioxane, dimethyl formamide (DMF), dimethyl acetamide (DMA), or dimethylsulfoxide (DMSO), at a high concentration, for example 1-500 mM. Meanwhile, the cell-binding molecule, such as antibody dissolved in an aqueous buffer pH 5~9.5, preferably pH 6~8.5, at 1~35 mg/ml concentration is treated with 1~20 equivalent of TCEP or DTT for 20 min to 12 hour. After the reduction, DTT can be removed by SEC chromatographic purification. TCEP can be optionally removed by SEC chromatography too, or can be staying in the reaction mixture for the next step reaction without purification. Furthermore, the reduction of antibodies or the other cell-binding agents with TCEP can be performed in the presence of a bridge linker of Formula (I), for which the conjugation reaction can be achieved simultaneously along with the TCEP reduction. After conjugation reaction, the over reduced free thiols on the cell-binding molecules can be oxidized with DHAA or Cu (II) to regenerate the disulfide bonds, or the free thiols can be capped with a thiol-reactive molecule, such as N-ethyl maleimide, sodium iodoacetate, sodium bromoacetate, bromoacetic acid methyl ester.

The aqueous solutions for the modification of cell-binding agents are buffered between pH 6 and 9, preferably between 6.5 and 7.5 and can contain any non-nucleophilic buffer salts useful for these pH ranges. Typical buffers include phosphate, triethanolamine HCl, HEPES, and MOPS buffers, which can contain additional components, such as cyclodextrins, sucrose and salts, for examples, NaCl and KCl. After the addition of the bridge linker of Formula (I) into the solution containing the reduced cell-binding molecules, the reaction mixture is incubated at a temperature of from 4° C. to 45° C., preferably at ambient temperature. The progress of the reaction can be monitored by measuring the decrease in the absorption at 254 nm, or increase in the absorption at 280 nm, or the other changes at an appropriate wavelength. After the reaction is complete, isolation of the modified cell-binding agent can be performed in a routine way, using for example gel filtration chromatography, or adsorptive chromatography.

The extent of modification can be assessed by measuring the absorbance of the nitropyridine thione, dinitropyridine dithione, pyridine thione, carboxamidopyridine dithione and dicarboxamidopyridine dithione group released via UV spectra. For the conjugation without a chromophore group, the modification or conjugation reaction can be monitored by LC-MS, preferably by UPLC-QTOF mass spectrometry, or Capilary electrophoresis-mass spectrometry (CE-MS). The bridge cross-linkers described herein have diverse functional groups that can react with any drugs, preferably cytotoxic agents that possess a suitable substituent. For examples, the modified cell-binding molecules bearing an amino or hydroxyl substituent can react with drugs bearing an N-hydroxysuccinimide (NHS) ester, the modified cell-binding molecules bearing a thiol substituent can react with drugs bearing a maleimido or haloacetyl group. Additionally, the modified cell-binding molecules bearing a carbonyl (ketone or aldehyde) substituent can react with drugs bearing a hydrazide or an alkoxyamine. One skilled in the art can readily determine which linker to use based on the known reactivity of the available functional group on the linkers.

Modified Cytotoxic Drugs

The cytotoxic drugs modified by reaction with cross-linkers of the present invention are preferably represented by the Formula (IV):

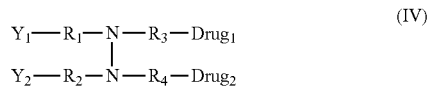
(IV)

Wherein $Y_1$, $Y_2$, $Drug_1$, $Drug_2$, $R_1$, $R_2$, $R_3$ and $R_4$ are defined the same as in Formula (I) and (II).

In preferred embodiments, $Y_1$ and $Y_2$ are a disulfide substituent; a maleimido; a haloacetyl; a carboxylic acid; a carboxylic acid halid; an ethenesulfonyl; an acryl (acryloyl); a carboxylic acid anhydride; an N-hydroxysuccinimide ester; or an ester formed with phenol, dinitrophenol, pentafluoro-phenol, tetrafluorophenol, difluorophenol, monofluoro-phenol, pentachlorophenol, triflate, imidazole, dichlorophenol, tetrachlorophenol, 1-hydroxybenzotriazole, tosylate, mesylate, 2-ethyl-5-phenylisoxa-zolium-3'-sulfonate.

The modified drugs can be prepared via reaction of the drug with the linkers of the Formula (I) to give a modified drug of Formula (IV) bearing functionality of $Y_1$ and $Y_2$ groups capable of reacting with a pair of thiol groups of a cell-binding agent. But for drugs containing a thiol, or the drugs undergoing to link a cell-binding molecule via the bridge linkers through thioether, thioester or disulfide bond, it is therefore preferred that the $Drug_1$ or $Drug_2$ may be synthesized to connect to $R_3$, or $R_4$ in a piece of components via the linkage of thioether, thioester or disulfide bond first. Then the synthesized $R_3$-$Drug_1$ or $R_4$-$Drug_2$ component is assembled to a hydrazine group to form the bridge linker modified drugs of Formula (IV).

For examples of the synthesis, a thiol-containing drug can be reacted with the linker of components $R_3$ or $R_4$ bearing a maleimdo substituent at neutral pH in aqueous buffer to give a $R_3$-$Drug_1$ or $R_4$-$Drug_2$ compartment bearing thioether linkage, and following by condensation with a compartment of hydrazine group containing function $Y_1$ and $Y_2$ groups to give a modified drug of Formula (IV) bearing thioether linkage. A drug bearing a hydroxyl group can be reacted with a linker component $R_3$ or $R_4$ bearing a halogen, or a tosylate, or a mesylate, in the presence of a mild base, to give a $R_3$-$Drug_1$ or $R_4$-$Drug_2$ compartment bearing ether linkage, and following by condensation with a compartment of hydrazine group containing function groups $Y_1$ and $Y_2$ to give a modified drug of Formula (IV) bearing thioether linkage. A hydroxyl group containing drug can be condensed with a linker of Formula (I) bearing a carboxyl group, in the presence of a dehydrating agent, such as EDC or dicyclohexylcarbodiimide (DCC), to give a modified drug of Formula (IV) via ester linkage. A drug bearing a thiol group can also react the linker of components $R_3$ or $R_4$ bearing a maleimido or a vinylsulfonyl, or a haloacetyl group, give a $R_3$-$Drug_1$ or $R_4$-$Drug_2$ compartment bearing thioether linkage, and following by condensation with a compartment of hydrazine group containing function groups $Y_1$ and $Y_2$ to give a modified drug of Formula (IV) bearing thioether linkage. An amino group containing drug can similarly undergo condensation with a carboxyl group on the bridge linker of Formula (I) to give a modified drug of Formula (IV) bearing amide bonds. The modified drug can be purified by standard methods such as column chromatography over silica gel or alumina, crystallization, preparatory thin layer chromatography, ion exchange chromatography, or HPLC.

Cell-Binding Agents

The cell-binding molecule that comprises the conjugates and the modified cell-binding agents of the present invention may be of any kind presently known, or that become known, molecule that binds to, complexes with, or reacts with a moiety of a cell population sought to be therapeutically or otherwise biologically modified.

The cell binding agents include, but are not limited to, large molecular weight proteins such as, for example, full-length antibodies (polyclonal antibodies, monoclonal antibodies, dimers, multimers, multispecific antibodies (e.g., bispecific antibodies); single chain antibodies; fragments of antibodies such as Fab, Fab', F(ab')$_2$, F$_v$, [Parham, J. Immunol. 131, 2895-2902 (1983)], fragments produced by a Fab expression library, anti-idiotypic (anti-Id) antibodies, CDR's, diabody, triabody, and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) J. of Immunology 170:4854-4861); interferons (such as type I, II, III); peptides; lymphokines such as IL-2, IL-3, IL-4, IL-5, IL-6, IL-10, GM-CSF, interferon-gamma (IFN-γ); hormones such as insulin, TRH (thyrotropin releasing hormones), MSH (melano-cyte-stimulating hormone), steroid hormones, such as androgens and estrogens, melano-cyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, polypeptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin [O'Keefe et al, 260 J. Biol. Chem. 932-937 (1985)]; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); bioactive dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93).

In general, a monoclonal antibody is preferred as a cell-surface binding agent if an appropriate one is available. And the antibody may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). *Nature* 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine) Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8, 396 (1959)) supplemented with 4.5 gm/l glucose, 0~20 mM glutamine, 0~20% fetal calf serum, several ppm amount of heavy metals, such as Cu, Mn, Fe, or Zn, etc, or/and the heavy metals added in their salt forms, and with an anti-foaming agent, such as polyoxyethylene-polyoxypropylene block copolymer.

In addition, antibody-producing cell lines can also be created by techniques other than fusion, such as direct transfoitnation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451, 570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859, 205 and 6,797,492; Liu et al, Immunol Rev. 222:9-27 (2008); Almagro et al, Front Biosci. 13: 1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix/Amgen), the HuMAb-Mouse (Medarex/BMS), the VelociMouse (Regeneron), see also U.S. Pat. Nos. 6,596,541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26:39-60 (2004); Houdebine, Curr Opin Biotechnol. 13:625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3:964-70, (2002)); Adams et al, J Immunol Methods. 231:249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 2003; 23(4):307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, a dendrimer, as long as such attachment permits the peptide or protein to retain its antigen binding specificity.

Examples of antibodies used for conjugation of drugs via the bridge linkers of this prevention for treating cancer, autoimmune disease, and/or infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, Lympho Stat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (α chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-05), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta_3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (α chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$),Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolyl-neuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (antibeta amyloid), Sonepcizumab (anti-sphingosine-1-phosphate), Sontuzumab (anti-episialin), Stamulumab (antimyostatin), Sulesomab (Leuko Scan, (anti-NCA-90 (granulocyte antigen), Tacatuzumab (anti-alpha-fetoprotein), Tadocizumab (anti-integrin $α_{IIb}β_3$), Talizumab (antiIgE), Tanezumab (anti-NGF), Taplitumomab (anti-CD19), Tefibazumab (Aurexis, (anti-clumping factor A), Telimomab, Tenatumomab (anti-tenascin C), Teneliximab (antiCD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (antiCD20), Trastuzumab (Herceptin, (anti-HER2/neu), Tremelimumab (anti-CTLA-4), Tucotuzumab celmoleukin (antiEpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $α_4β_7$), Veltuzumab (anti-CD20), Vepalimomab (anti-AOC3 (VAP-1), Visilizumab (Nuvion, antiCD3), Vitaxin (anti-vascular integrin avb3), Volociximab (anti-integrin $α_5β_1$), Votumumab (HumaSPECT, anti-tumor antigen CTAA16.88), Zalutumumab (HuMax-EGFr, (antiEGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (antiCEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRαβ (T cell receptor alpha/beta), complex, from MedImmune Inc for Graft-versus-host disease], RING SCAN [ anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; Lympho-Cide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone Systems, NJ) and Cetuximab (ImClone, NJ).

Other antibodies as cell binding molecules/ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD22? (breast, ovarian cancers), CD262 (NSCLC and other cancers), CD309 (ovarian cancers), CD326 (solid tumors), CEACAM3 (colorectal, gastric cancers), CEACAMS (carcinoembryonic antigen; CEA, CD66e) (breast, colorectal and lung cancers), DLL4 (delta-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insu-IM-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins (αvβ3, α5β1, α6β4, αIIβ3, α5β5, αvβ5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1,lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76).

The cell-binding agents, more preferred antibodies, can be any agents that are able to against tumor cells, virus infected cells, microorganism infected cells, parasite infected cells, autoimmune cells, activated cells, myeloid cells, activated T-cells, B cells, or melanocytes. More specifically the cell binding agents can be any agent/molecule that is able to against any one of the following antigens or receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5AC, 5T4 (Trophoblast glycoprotein, TPBG, 5T4, Wnt-Activated Inhibitory Factor 1 or WAIF1), Adenocarcinoma antigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, Canis lupus familiaris IL31, Carbonic anhydrase IX, Cardiac myosin, CCL11(C—C motif chemokine 11), CCR4 (C—C chemokine receptor type 4, CD194), CCR5, CD3E (epsilon), CEA (Carcinoembryonic antigen), CEACAM3, CEACAMS (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD115), CSF2 (colony stimulating factor 2, Granulocyte-macrophage colony-stimulating factor (GM-CSF)), CTLA4 (cytotoxic T-lymphocyte-associated protein 4), CTAA16.88 tumor antigen, CXCR4 (CD184), C-X-C chemokine receptor type 4, cyclic ADP ribose hydrolase, Cyclin B1, CYP1B1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* shiga toxin type-1, *E. coli* shiga toxin type-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1.F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor α-chain, Growth differentiation factor 8, GP100, GPNMB (Transmem-brane glycoprotein NMB), GUCY2C (Guanylate cyclase 2C, guanylyl cyclase C(GC-C), intestinal Guanylate cyclase, Guanylate cyclase-C receptor, Heat-stable entero-toxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influeza hemagglutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins (α4, $α_{IIb}β_3$, αvβ3, $α_4β_7$, α5β1, α6β4, α7β7, αIIβ3, α5β5, αvβ5), Interferon gamma-induced protein, ITGA2, ITGB2, KIR2D, LCK, Le, Legumain, Lewis-Y antigen, LFA-1(Lymphocyte function-associated antigen 1, CD11a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (mesothelin), MUC1(Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1,CD279), PDGF-Rα (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β, (Transforming growth factor beta), TGF-, β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-R1 (Tumor necrosis apoprosis Inducing ligand Receptor 1), TRAILR2 (Death receptor 5 (DR5)), tumor-associated calcium signal transducer 2, tumor specific glycosylation of MUC1, TWEAK receptor, TYRP1(glycoprotein 75), TRP-2, Tyrosinase, VCAM-1 (CD106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

In another specific embodiment, the cell-binding ligand-drug conjugates via the bridge linkers of this invention are used for the targeted treatment of cancers. The targeted cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodennal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproli-ferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates via the bridge likers of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agamma-globulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogamma-globulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habeimann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the bridge linkers of this invention for the treatment or prevention of an autoimmune disease can be, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial(M2) antibody; Rheumatoid factor antibody; Anti-MCV antibody; Anti-topoisomerase antibody; Anti-neutrophil cytoplasmic(cANCA) antibody.

In certain preferred embodiments, the binding molecule for the conjugate in the present invention, can bind to both a receptor and a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD79b, CD90, CD125, CD147, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful cell binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimidase, influenza virus hemagglutinin, HTLV tax, herpes simplex virus glycoprotein (e.g. gB, gC, gD, and gE) and hepatitis B surface antigen) that is capable of eliciting an immune response. As used herein, the teen "microbial antigen" includes, but is not limited to, any microbial peptide, polypeptide, protein, saccharide, polysaccharide, or lipid molecule (e.g., a bacteria, fungi, pathogenic protozoa, or yeast polypeptides including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The cell binding molecules—drug conjugates via the bridge linkers of this invention can be used in the treatment of infectious diseases. These infectious diseases include, but are not limited to, Acinetobacter infections, *Actinomycosis*, African sleeping sickness (African trypanosomiasis), AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, Bacteroides infection, Balantidiasis, Baylisascaris infection, BK virus infection, Black piedra, *Blastocystis hominis* infection, Blastomycosis, Bolivian hemorrhagic fever, Borrelia infection, Botulism (and Infant botulism), Brazilian hemorrhagic fever, Brucellosis, Burkholderia infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chlamydia, *Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococ-cosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, Fusobacterium infection, Gas gangrene (Clostridial myonecrosis), Geotrichosis, Gerstmann-Straussler-Scheinker syndrome, Giardiasis, Glanders, Gnathosto-miasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, Helicobacter pylori infection, Hemolyticuremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), *Lymphocytic choriomeningitis*, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), Mycoplasma pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis pneumonia*, Pneumonia, Poliomyelitis, Prevotella infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsial-pox, Rift Valley fever, Rocky mountain spotted fever, Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringwoim of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), sYersinia pseudotuberculosis infection, Yersiniosis, Yellow fever, Zygomycosis.

The cell binding molecule, which is more preferred to be an antibody described in this patent that are against pathogenic strains include, but are not limit, *Acinetobacter baumannii*, *Actinomyces israelii*, *Actinomyces gerencseriae* and *Propionibacterium propionicus*, *Trypanosoma brucei*, HIV (Human immunodeficiency virus), *Entamoeba histolytica*, *Anaplasma* genus, *Bacillus anthracis*, *Arcanobacterium haemolyticum*, Junin virus, *Ascaris lumbricoides*, *Aspergillus* genus, Astroviridae family, *Babesia* genus, *Bacillus cereus*, multiple bacteria, *Bacteroides* genus, *Balantidium coli*, *Baylisascaris* genus, BK virus, *Piedraia hortae*, *Blastocystis hominis*, Blastomyces deunatitides, Machupo virus, *Borrelia* genus, *Clostridium botulinum*, Sabia, *Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus*, *Trypanosoma cruzi*, *Haemophilus ducreyi*, Varicella zoster virus (VZV), *Chlamydia trachomatis*, *Chlamydophila pneumoniae*, *Vibrio cholerae*, *Fonsecaea pedrosoi*, *Clonorchis sinensis*, *Clostridium difficile*, *Coccidioides immitis* and *Coccidioides posadasii*, Colorado tick fever virus, rhinoviruses, coronaviruses, CJD prion, Crimean-Congo hemorrhagic fever virus, *Cryptococcus neoformans*, *Cryptosporidium* genus, *Ancylostoma braziliense*; multiple parasites, *Cyclospora cayetanensis*, *Taenia solium*, Cytomegalovirus, Dengue viruses (DEN-1, DEN-2, DEN-3 and DEN-4)—Fla-viviruses, *Dientamoeba fragilis*, *Corynebacterium diphtheriae*, *Diphyllobothrium*, *Dracunculus medinensis*, Ebolavirus, *Echinococcus* genus, *Ehrlichia* genus, *Enterobius vermicularis*, *Enterococcus* genus, *Enterovirus* genus, *Rickettsia prowazekii*, Parvovirus B19, Human herpesvirus 6 and Human herpesvirus 7, *Fasciolopsis buski*, *Fasciola hepatica* and *Fasciola gigantica*, FFI prion, *Filarioidea* superfamily, *Clostridium perfringens*, *Fusobacterium* genus, *Clostridium perfringens*; other *Clostridium* species, *Geotrichum candidum*, GSS prion, *Giardia intestinalis*, *Burkholderia mallei*, *Gnathostoma spinigerum* and *Gnathostoma hispidum*, *Neisseria gonorrhoeae*, *Klebsiella granulomatis*, *Streptococcus pyogenes*, *Streptococcus agalactiae*, *Haemophilus influenzae*, *Enteroviruses*, mainly Cox-sackie A virus and *Enterovirus* 71, Sin Nombre virus, *Helicobacter pylon*, *Escherichia coli* 0157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum*, *Ancylostoma duodenale* and *Necator americanus*, *Hemophilus influenzae*, *Human bocavirus*, *Ehrlichia ewingii*, *Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomyxoviridae family, *Isospora belli*, *Kingella kingae*, *Klebsiella pneumoniae*, *Klebsiella ozaenas*, *Klebsiella rhinoscleromotis*, Kuru prion, Lassa virus, *Legionella pneumophila*, *Legionella pneumophila*, *Leishmania* genus, *Mycobacterium leprae* and *Mycobacterium lepromatosis*, *Leptospira* genus, *Listeria monocytogenes*, *Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei*, *Neisseria meningitides*, Metagonimus yokagawai, Microsporidia phylum, Molluscum contagiosum virus (MCV), Mumps virus, *Rickettsia typhi*, *Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus*, *Paracoccidioides brasiliensis*, *Paragonimus westemiani* and other *Paragonimus* species, *Pasteurella* genus, *Pediculus humanus capitis*, *Pediculus humanus corporis*, *Phthirus pubis*, *Bordetella pertussis*, *Yersinia pestis*, *Streptococcus pneumoniae*, *Pneumocystis jirovecii*, Poliovirus, *Prevotella* genus, *Naegleria fowleri*, JC virus, *Chlamydophila psittaci*, *Coxiella bumetii*, Rabies virus, *Streptobacillus moniliformis* and *Spirillum minus*, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei*, *Schistosoma* genus, *Shigella* genus, Varicella zoster virus, Variola major or Variola minor, *Sporothrix schenckii*, *Staphylococcus* genus, *Staphylococcus* genus, *Staphylococcus aureus*, *Streptococcus pyogenes*, *Strongyloides stercoralis*, *Treponema pallidum*, *Taenia* genus, *Clostridium tetani*, *Trichophyton* genus, *Trichophyton tonsurans*, *Trichophyton* genus, *Epidermophyton floccosum*, *Trichophyton rubrum*, and *Trichophyton mentagrophytes*, *Trichophyton rubrum*, *Hortaea wemeckii*, *Trichophyton* genus, *Malassezia* genus, *Toxocara canis* or *Toxocara cati*, *Toxoplasma gondii*, *Trichinella spiralis*, *Trichomonas vaginalis*, *Trichuris trichiura*, *Mycobacterium tuberculosis*, *Francisella tularensis*, *Ureaplasma urealyticum*, Venezuelan equine encephalitis virus, *Vibrio colerae*, Guanarito virus, West Nile virus, *Trichosporon beigelii*, *Yersinia pseudotuberculosis*, *Yersinia enterocolitica*, Yellow fever virus, Mucorales order (Mucormycosis) and Entomophthorales order (Entomophthoramycosis), *Pseudomonas aeruginosa, Campylobacter* (Vibrio) *fetus, Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia prowazeki, Rickettsia tsutsugumushi, Clamydia* spp.; pathogenic fungi (*Aspergillus fumigatus, Candida albicans, Histoplasma capsulatum*); protozoa (*Entomoeba histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other antibodies as cell binding ligands used in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (*Lymphocytic choriomeningitis*), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAY (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate via the bridge linkers of the invention together with a pharmaceutically acceptable carrier, diluent, or excipient for treatment of cancers, infections or autoimmune disorders. The method for treatment of cancers, infections and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation, the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate via the linkers of the invention will be supplied as solutions or as a lyophilized solid that can be redissolved in sterile water for injection. Examples of suitable protocols of conjugate administration are as follows. Conjugates are given weekly for 8~20 weeks as an i.v. bolus. Bolus doses are given in 50 to 500 ml of normal saline to which human serum albumin (e.g. 0.5 to 5 mL of a concentrated solution of human serum albumin, 100 mg/mL) can be added. Dosages will be about 50 µg to 100 mg/kg of body weight per week, i.v. (range of 10 µg to 50 mg/kg per injection). 4~20 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general teens, the conjugates via the linkers of this invention may be provided in an aqueous physiological buffer solution containing 0.1 to 10% w/v conjugates for parenteral administration. Typical dose ranges are from 1 µg/kg to 0.1 g/kg of body weight per day; a preferred dose range is from 0.01 mg/kg to 20 mg/kg of body weight per day, or per week, or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the conjugates by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two week or per month. Preferably the unit dose range is from 1 to 500 mg administered one to four times a week, and even more preferably from 1 mg to 100 mg, once a week. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasal, particularly in the form of powders, nasal drops, or aerosols; or dermally, for example, topically in ointments, creams, lotions, gels or sprays, or via trans-dermal patches.

Drugs/Cytotoxic Agents

Drugs that can be conjugated to a cell-binding molecule in the present invention are small molecule drugs including cytotoxic agents, which can be linked to or after they are modified for linkage to the cell-binding agent. A "small molecule drug" is broadly used herein to refer to an organic, inorganic, or organometallic compound that may have a molecular weight of for example 100 to 1800, more suitably from 120 to 1400. Small molecule drugs are well characterized in the art, such as in WO05058367A2, and in U.S. Pat. No. 4,956,303, among others and are incorporated in their entirety by reference. The drugs include known drugs and those that may become known drugs.

Drugs that are known include, but not limited to,

1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocannycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemel-amine, trietylenephosphoramide, triethylenethiophosphaoramide and trimethylolomel-amine]; b). Plant Alkaloids: such as Vinca alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), caunofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). antibiotics, such as the enediyne antibiotics (e.g. calicheamicins, especially calicheamicin γ1, δ1, α1 and β1, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; f). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Antiadrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; l). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethyl-penicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacro, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclo-cycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin; 4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexel-vucitabine, didanosine (ddI), elvucitabine, emtricitabine (FTC), entecavir, famciclovir, fluorouracil (5-FU), 3'-fluoro-substituted 2', 3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), l-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The drugs used for conjugates via a bridge linker of the present invention also include radioisotopes. Examples of radioisotopes (radionuclides) are $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. Radioisotope labeled antibodies are useful in receptor targeted imaging experiments or can be for targeted treatment such as with the antibody-drug conjugates of the invention (Wu et al (2005) Nature Biotechnology 23(9): 1137-1146). The cell binding molecules, e.g. an antibody can be labeled with ligand reagents through the bridge linkers of the present patent that bind, chelate or otherwise complex a radioisotope metal, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.).

6). The pharmaceutically acceptable salts, acids or derivatives of any of the above drugs.

In another embodiment, the drug in the Formula (II) and (IV) can a chromophore molecule, for which the conjugate can be used for detection, monitoring, or study the interaction of the cell binding molecule with a target cell. Chromophore molecules are a compound that have the ability to absorb a kind of light, such as UV light, florescent light, IR light, near IR light, visual light; A chromatophore molecule includes a class or subclass of xanthophores, erythrophores, iridophores, leucophores, melanophores, and cyanophores; a class or subclass of fluorophore molecules which are fluorescent chemical compounds re-emitting light upon light; a class or subclass of visual phototransduction molecules; a class or subclass of photophore molecules; a class or subclass of luminescence molecules; and a class or subclass of luciferin compounds.

The chromophore molecule can be selected from, but not limited, Non-protein organic fluorophores, such as: Xanthene derivatives (fluorescein, rhodamine, Oregon green, eosin, and Texas red); Cyanine derivatives: (cyanine, indocarbocyanine, oxacarbocyanine, thiacarbocyanine, and merocyanine); Squaraine derivatives and ring-substituted squaraines, including Seta, SeTau, and Square dyes; Naphthalene derivatives (dansyl and prodan derivatives); Coumarin derivatives; Oxadiazole derivatives (pyridyloxazole, nitro-benzoxadiazole and benzoxadiazole); Anthracene derivatives (anthraquinones, including DRAQ5, DRAQ7 and CyTRAK Orange); Pyrene derivatives (cascade blue, etc); Oxazine derivatives (Nile red, Nile blue, cresyl violet, oxazine 170 etc). Acridine derivatives (proflavin, acridine orange, acridine yellow etc). Arylmethine derivatives (auramine, crystal violet, malachite green). Tetrapyrrole derivatives (porphin, phthalocyanine, bilirubin).

Or a chromophore molecule can be selected from any analogs and derivatives of the following fluorescent compounds: CF dye (Biotium), DRAQ and CyTRAK probes (Bio-Status), BODIPY (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPEPerCP, Phycobilisomes)(Columbia Biosciences), APC, APCXL, RPE, BPE (Phyco-Biotech);

Examples of the widely used fluorophore compounds which are reactive or conjugatable with the linkers of the invention are: Allophycocyanin (APC), Aminocou-marin, APC-Cy7 conjugates, BODIPY-FL, Cascade Blue, Cy2, Cy3, Cy3.5, Cy3B, Cy5, Cy5.5, Cy7, Fluorescein, FluorX, Hydroxycoumarin, Lissamine Rhodamine B, Lucifer yellow, Methoxycoumarin, NBD, Pacific Blue, Pacific Orange, PE-Cy5 conjugates, PE-Cy7 conjugates, PerCP, R-Phycoerythrin(PE), Red 613, Seta-555-Azide, Seta-555-DBCO, Seta-555-NHS, Seta-580-NHS, Seta-680-NHS, Seta-780-NHS, Seta-APC-780, Seta-PerCP-680, Seta-R-PE-670, SeTau-380-NHS, SeTau-405-Maleimide, SeTau-405-NHS, SeTau-425-NHS, SeTau-647-NHS, Texas Red, TRITC, TruRed, X-Rhodamine.

The fluorophore compounds that can be linked to the linkers of the invention for study of nucleic acids or proteins are selected from the following compounds or their derivatives: 7-AAD (7-aminoactinomycin D, CG-selective), Acridine Orange, Chromomycin A3, CyTRAK Orange (Biostatus, red excitation dark), DAPI, DRAQ5, DRAQ7, Ethidium Bromide, Hoechst33258, Hoechst33342, LDS 751, Mithramycin, Propidiumlodide (PI), SYTOX Blue, SYTOX Green, SYTOX Orange, Thiazole Orange, TO-PRO: Cyanine Monomer, TOTO-1, TO-PRO-1, TOTO-3, TO-PRO-3, YOSeta-1, YOYO-1. The fluorophore compounds that can be linked to the linkers of the invention for study cells are selected from the following compounds or their derivatives: DCFH (2'7'Dichorodihydro-fluorescein, oxidized form), DHR (Dihydrorhodamine 123, oxidized form, light catalyzes oxidation), Fluo-3 (AM ester. pH>6), Fluo-4 (AM ester. pH 7.2), Indo-1 (AM ester, low/high calcium (Ca2+)), SNARF(pH 6/9). The preferred fluorophore compounds that can be linked to the linkers of the invention for study proteins/antibodies are selected from the following compounds or their derivatives: Allophycocyanin(APC), AmCyan1 (tetramer, Clontech), AsRed2 (tetramer, Clontech), Azami Green (monomer, MBL), Azurite, B-phycoerythrin(BPE), Cerulean, CyPet, DsRed monomer (Clontech), DsRed2 ("RFP", Clontech), EBFP, EBFP2, ECFP, EGFP (weak dimer, Clontech), Emerald (weak dimer, Invitrogen), EYFP (weak dimer, Clontech), GFP (S65A mutation), GFP (S65C mutation), GFP (S65L mutation), GFP (S65T mutation), GFP (Y66F mutation), GFP (Y66H mutation), GFP (Y66W mutation), GFPuv, HcRedl, J-Red, Katusha, Kusabira Orange (monomer, MBL), mCFP, mCherry, mCitrine, Midoriishi Cyan (dimer, MBL), mKate (TagFP635, monomer, Evrogen), mKeima-Red (monomer, MBL), mKO, mOrange, mPlum, mRaspberry, mRFP1 (monomer, Tsien lab), mStrawberry, mTFP1, mTurquoise2, P3 (phycobilisome complex), Peridinin Chlorophyll (PerCP), R-phycoerythrin(RPE), T-Sapphire, TagCFP (dimer, Evrogen), TagGFP (dimer, Evrogen), TagRFP (dimer, Evrogen), TagYFP (dimer, Evrogen), tdTomato (tandem dimer), Topaz, TurboFP602 (dimer, Evrogen), TurboFP635 (dimer, Evrogen), TurboGFP (dimer, Evrogen), TurboRFP (dimer, Evrogen), TurboYFP (dimer, Evrogen), Venus, Wild Type GFP, YPet, ZsGreenl (tetramer, Clontech), ZsYellow1 (tetramer, Clontech).

In yet another embodiment, the preferred cytotoxic agents that conjugated to a cell-binding molecule via a bridge linker of this patent are tubulysins, maytansinoids, taxanoids (taxanes), CC-1065 analogs, daunorubicin and doxorubicin compounds, benzodiazepine dimers (e.g., dimers of pyrrolobenzodiazepine (PBD), tomaymycin, anthramycin, indolinobenzodiazepines, imidazobenzothiadiazepines, or oxazolidino-benzodiazepines), calicheamicins and the enediyne antibiotics, actinomycin, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristines, hemiasterlins, nazumamides, microginins, radiosumins, alterobactins, microsclerodettnins, theonellamides, esperamicins, PNU-159682, and their analogues and derivatives above thereof.

Tubulysins that are preferred for conjugation in the present invention are well known in the art and can be isolated from natural sources according to known methods or prepared synthetically according to known methods (e. g. Balasubramanian, R.; et al. J. Med. Chem., 2009, 52, 238-240. Wipf, P.; et al. Org. Left., 2004, 6, 4057-4060. Pando, O.; et al. J. Am. Chem. Soc., 2011, 133, 7692-7695. Reddy, J. A.; et al. Mol. Pharmaceutics, 2009, 6, 1518-1525. Raghavan, B.; et al. J. Med. Chem., 2008, 51, 1530-1533. Patterson, A. W.; et al. J. Org. Chem., 2008, 73, 4362-4369. Pando, O.; et al. Org. Lett., 2009, 11 (24), pp 5567-5569. Wipf, P.; et al. Org. Lett., 2007, 9 (8), 1605-1607. Friestad, G. K.; Org. Lett., 2004, 6, pp 3249-3252. Hillary M. Peltier, H. M.; et al. J. Am. Chem. Soc., 2006, 128, 16018-16019. Chandrasekhar, S.; et al. J. Org. Chem., 2009, 74, 9531-9534. Liu, Y.; et al. Mol. Pharmaceutics, 2012, 9, 168-175. Friestad, G. K.; et al. Org. Lett., 2009, 11, 1095-1098. Kubicek, K.; et al., Angew Chem Int Ed Engl, 2010. 49: p. 4809-12. Chai, Y.; et al., Chem Biol, 2010, 17: 296-309. Ullrich, A.; et al., Angew Chem Int Ed Engl, 2009, 48, 4422-5. Sani, M.; et al. Angew Chem Int Ed Engl, 2007, 46, 3526-9. Domling, A.; et al., Angew Chem Int Ed Engl, 2006. 45, 7235-9. Patent applications: Zanda, M.; et al, Can. Pat. Appl. CA 2710693 (2011). Chai, Y.; et al. Eur. Pat. Appl. 2174947 (2010), PCT WO 2010034724. Leamon, C.; et al, PCT WO 2010033733, WO 2009002993. Ellman, J.; et al, PCT WO 2009134279; PCT WO 2009012958, US appl. 20110263650, 20110021568, Matschiner, G.; et al, PCT WO 2009095447.Vlahov, I.; et al, PCT WO 2009055562, WO 2008112873. Low, P.; et al, PCT WO 2009026177. Richter, W., PCT WO 2008138561. Kjems, J.; et al, PCT WO 2008125116. Davis, M.; et al, PCT WO 2008076333. Diener, J.; et al, U.S. Pat. Appl. 20070041901, WO 2006096754. Matschiner, G.; et al, PCT WO 2006056464. Vaghefi, F.; et al, 5 PCT WO 2006033913. Doemling, A., Ger. Offen. DE 102004030227; PCT WO 2004005327; WO 2004005326; WO2004005269. Stanton, M.; et al, U.S. Pat. Appl. Publ. 20040249130. Hoefle, G.; et al, Ger. Offen. DE 10254439; DE 10241152; DE 10008089. Leung, D.; et al, WO 2002077036. Reichenbach, H.; et al, Ger. Offen. DE 19638870; Wolfgang, R.; US 20120129779, Chen, H., US appl. 20110027274.

The preferred structure of tubulysins for conjugation of cell binding molecules are described in the patent application of PCT/IB2012/053554.

Examples of the structures of the conjugates of the antibody-tubulysin analogs via the bridge linker are T01, T02, T03, T04, T05, T06 and T07 as following:

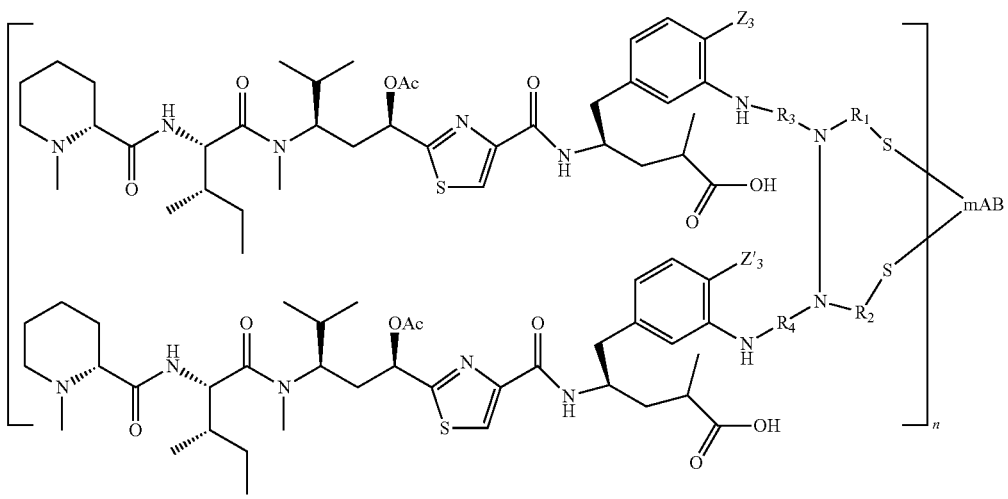

T01

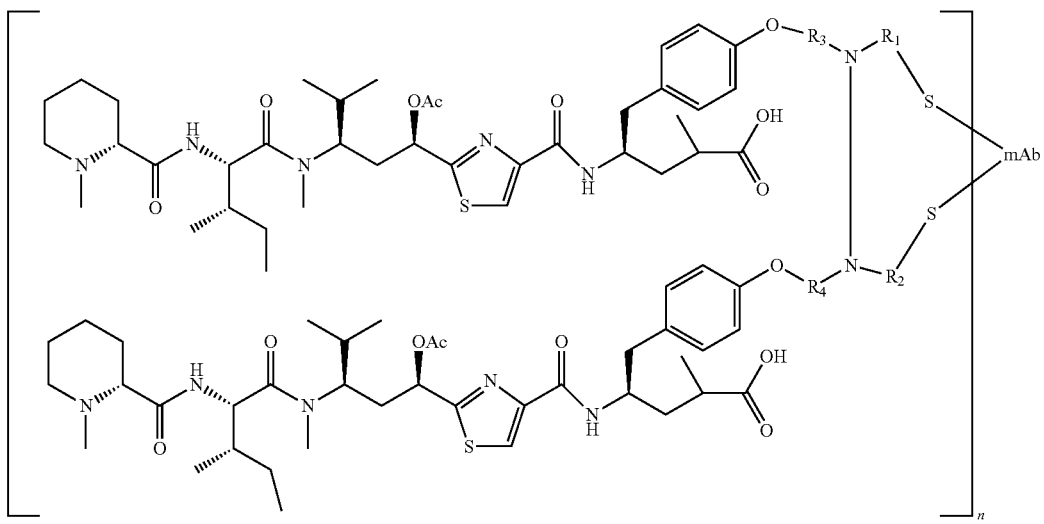

T02

-continued
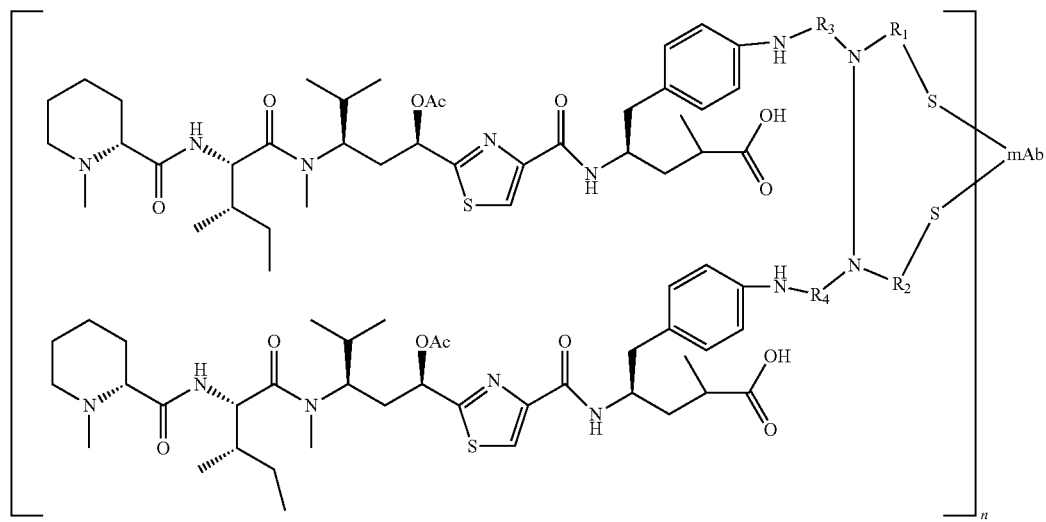
T03
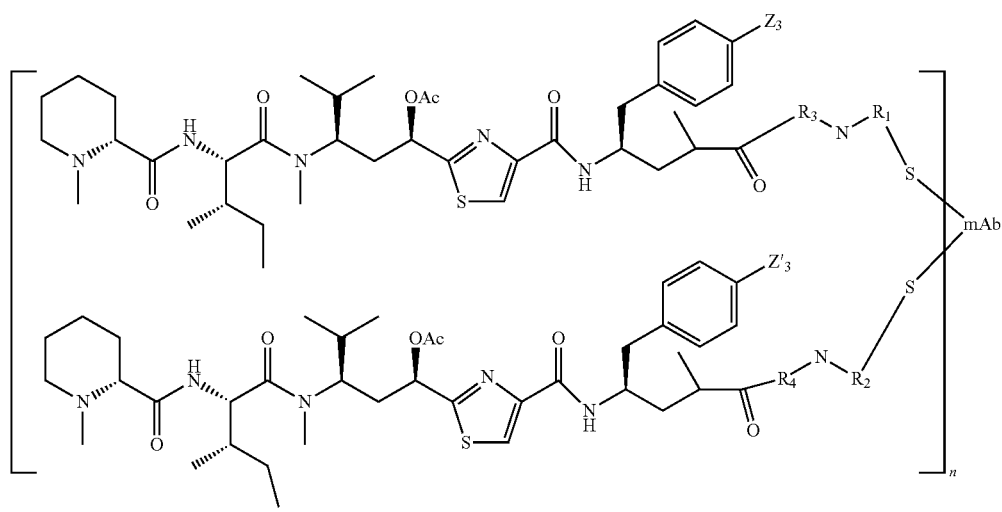
T04
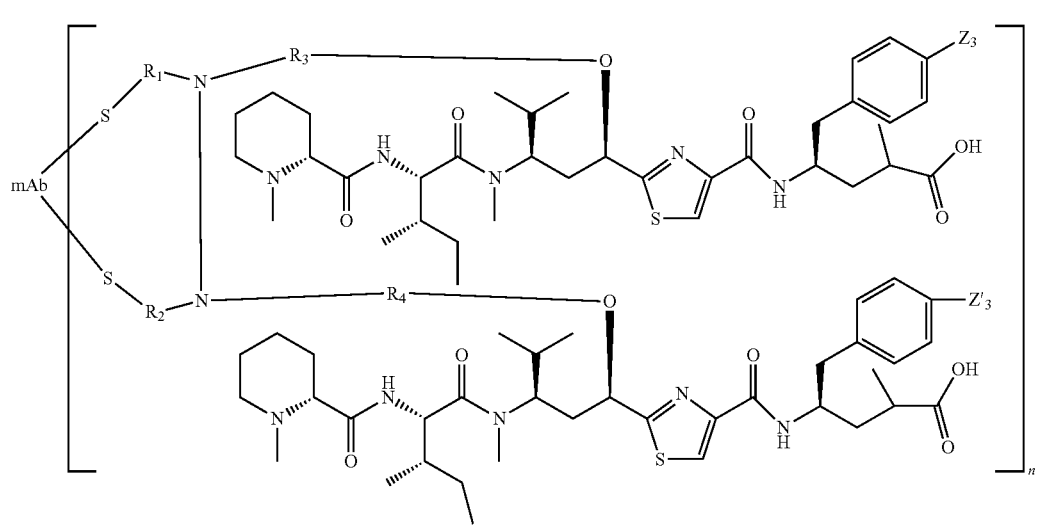
T05

-continued

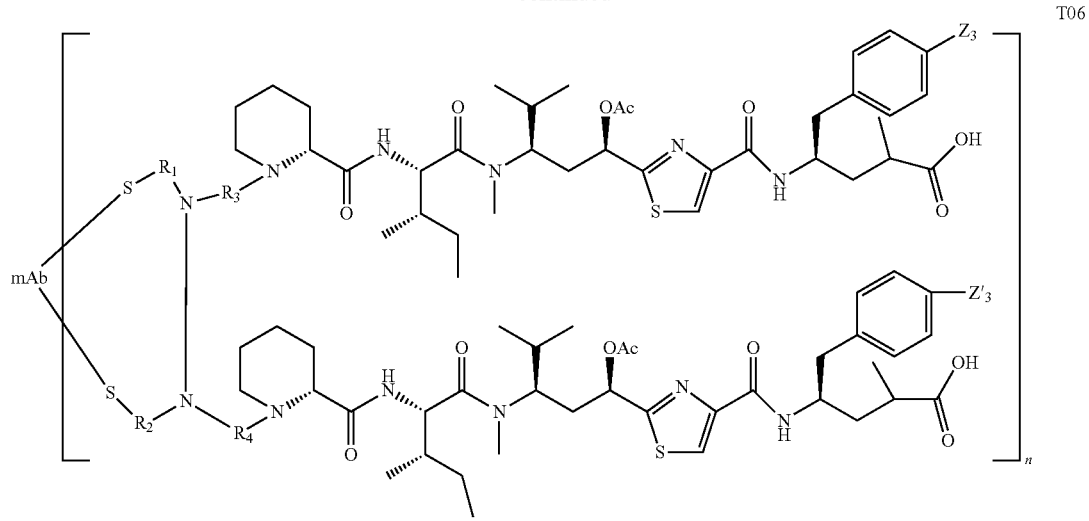

T06

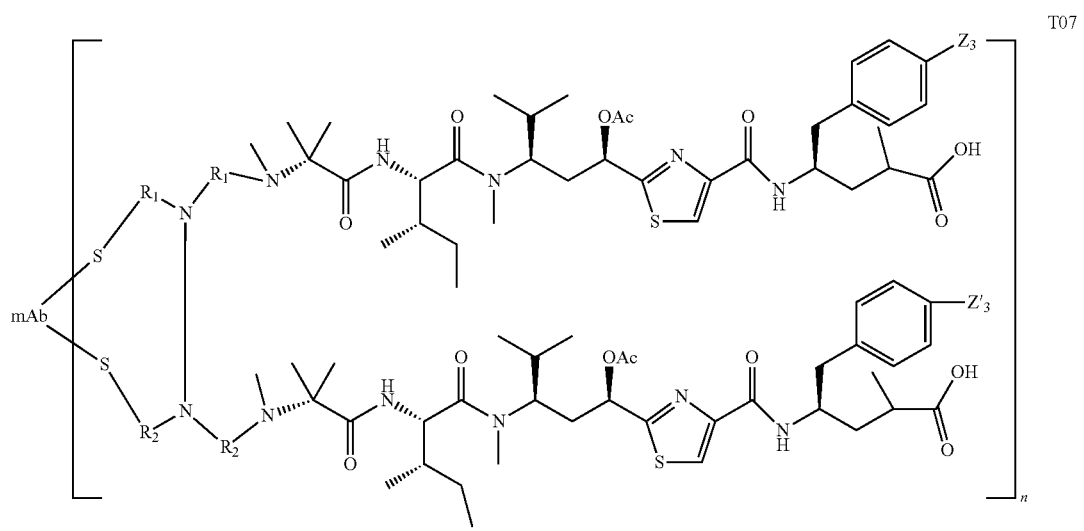

T07

Wherein mAb is an antibody; $Z_3$ and $Z'_3$ are independently H, $R_1$, $OP(O)(OM_1)(OM_2)$, $OCH_2OP(O)(OM_1)(OM_2)$, $OSO_3M_1$, or O-glycoside (glucoside, galactoside, mannoside, glucuronoside, alloside, fructoside, etc), NH-glycoside, S-glycoside, or $CH_2$-glycoside; $M_1$ and $M_2$ are independently H, Na, K, Ca, Mg, $NH_4$, or $NR_1R_2R_3R_4$; n is 1-20; $R_1$, $R_2$, $R_3$ and $R_4$ are the same defined in Formula (I).

Calicheamicins and their related enediyne antibiotics that are preferred for cell-binding molecule-drug conjugates of this patent are described in: Nicolaou, K. C. et al, Science 1992, 256, 1172-1178; Proc. Natl. Acad. Sci USA. 1993, 90, 5881-5888), U.S. Pat. Nos. 4,970,198; 5,053,394; 5,108,912; 5,264,586; 5,384,412; 5,606,040; 5,712,374; 5,714,586; 5,739,116; 5,770,701; 5,770,710; 5,773,001; 5,877,296; 6,015,562; 6,124,310; 8,153,768. An Example of the structure of the conjugate of the antibody-Calicheamicin analog via the bridge linker is C01 as the following:

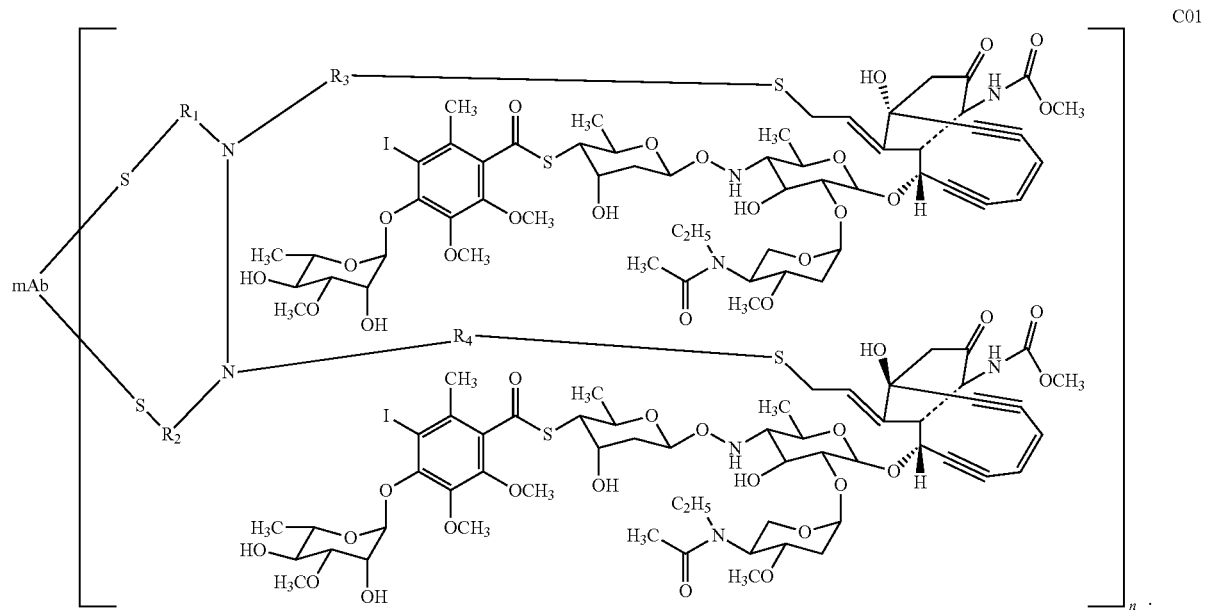

Wherein mAb is an antibody; n is 1~20; $R_1$, $R_2$, $R_3$ and $R_4$ are the same defined in Formula (I).

Maytansinoids that are preferred to be used in the present invention including maytansinol and its analogues are described in U.S. Pat. Nos. 4,256,746, 4,361,650, 4,307,016, 4,294,757, 4,294,757, 4,371,533, 4,424,219, 4,331,598, 4,450,254, 4,364,866, 4,313,946, 4,315,929 4,362,663, 4,322,348, 4,371,533, 4,424,219, 5,208,020, 5,416,064, 5,208,020; 5,416,064; 6,333.410; 6,441,163; 6,716,821; 7,276,497, 7,301,019, 7,303,749, 7,368,565, 7,411,063, 7,851,432, and 8,163,888. An example of the structure of the conjugate of the antibody-Maytansinoids via the bridge linker is as the following M01:

Wherein mAb is an antibody; n is 1-20; $R_1$, $R_2$, $R_3$ and $R_4$ are the same defined in Formula (I).

Taxanes, which includes Paclitaxel (Taxol), a cytotoxic natural product, and docetaxel (Taxotere), a semi-synthetic derivative, and their analogs which are preferred for conjugation via the bridge linkers of the present patent are exampled in: K C. Nicolaou et al., J. Am. Chem. Soc. 117, 2409-2420, (1995); Ojima et al, J. Med. Chem. 39:3889-3896 (1996); 40:267-278 (1997); 45, 5620-5623 (2002); Ojima et al., Proc. Natl. Acad. Sci., 96:4256-4261 (1999; Kim et al., Bull. Korean Chem. Soc., 20, 1389-1390 (1999); Miller, et al. J. Med. Chem., 47, 4802-4805(2004); U.S. Pat. No. 5,475,011 5,728,849, 5,811,452; 6,340,701; 6,372,738;

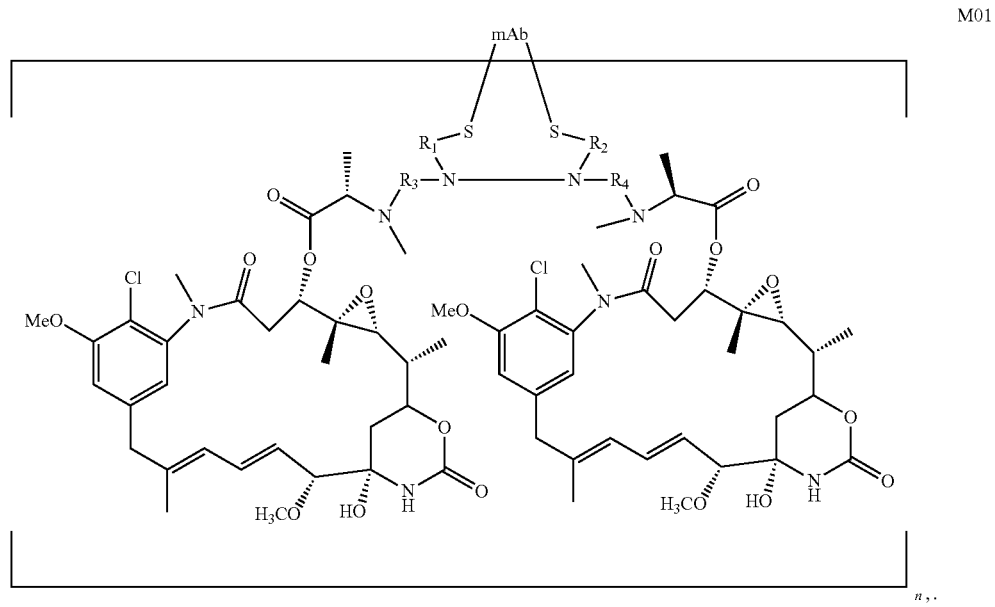

6,391,913, 6,436,931; 6,589,979; 6,596,757; 6,706,708; 7,008,942; 7,186,851; 7,217,819; 7,276,499; 7,598,290; and 7,667,054.
Examples of the structures of the conjugate of the antibody-taxanes via the bridge linker are as the following Tx01, Tx02 and Tx03.
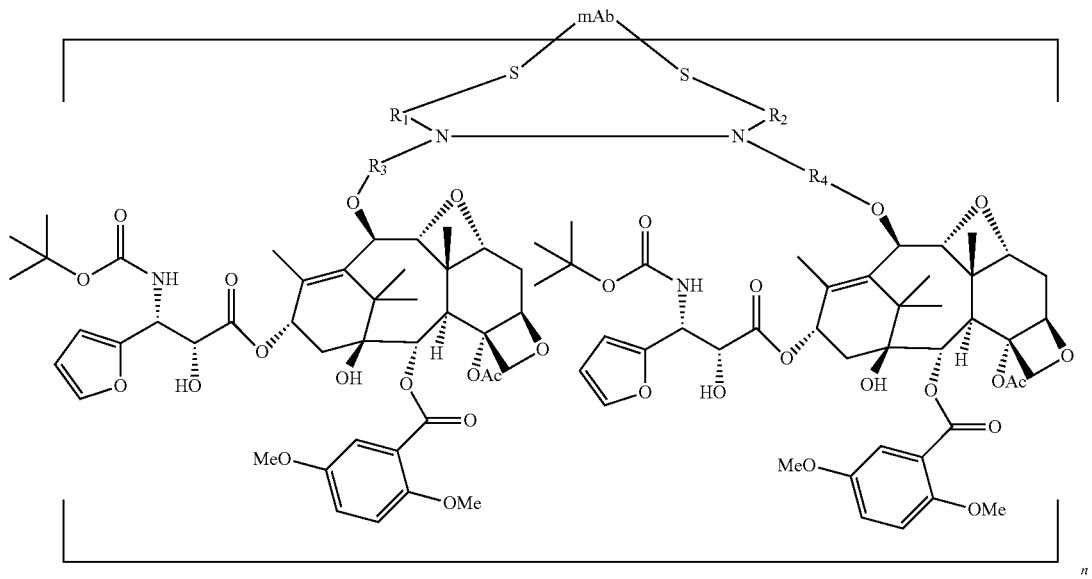
Tx01
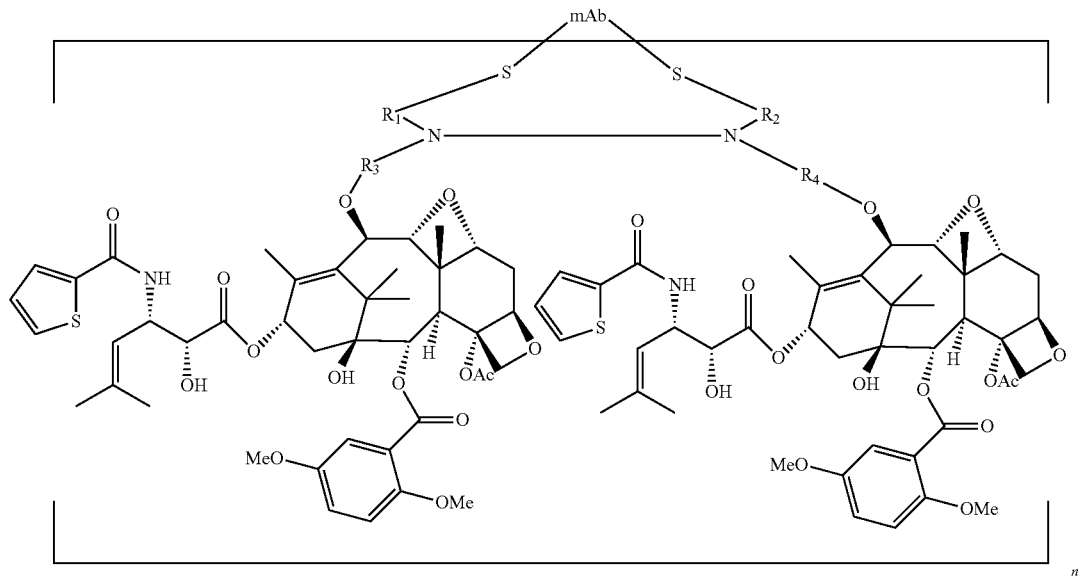
Tx02

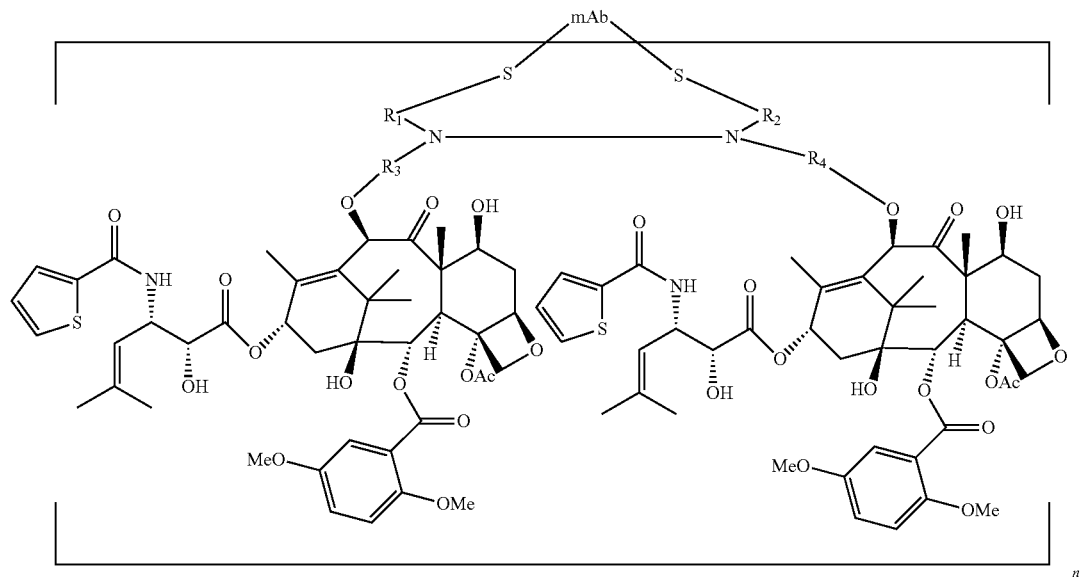

Tx03

Wherein mAb is an antibody; n is 1~20; $R_1$, $R_2$, $R_3$ and $R_4$ are the same defined in Formula (I).

CC-1065 analogues and doucarmycin analogs are also preferred to be used for a conjugate with the bridge linkers of the present patent. The examples of the CC-1065 analogues and doucarmycin analogs as well as their synthesis are described in: e.g. Warpehoski, et al, J. Med., Chem. 31:590-603 (1988), D. Boger et al., J. Org. Chem; 66; 6654-6661, 2001; U.S. Pat. Nos. 4,169,888, 4,391,904, 4,671,958, 4,816,567, 4,912,227, 4,923,990, 4,952,394, 4,975,278, 4,978,757, 4,994,578, 5,037,993, 5,070,092, 5,084,468, 5,101,038, 5,117,006, 5,137,877, 5,138,059, 5,147,786, 5,187,186, 5,223,409, 5,225,539, 5,288,514, 5,324,483, 5,332,740, 5,332,837, 5,334,528, 5,4034,84, 5,427,908, 5,475,092, 5,495,009, 5,530,101, 5,545,806, 5,547,667, 5,569,825, 5,571,698, 5,573,922, 5,580,717, 5,585,089, 5,585,499, 5,587,161, 5,595,499, 5,606,017, 5,622,929, 5,625,126, 5,629,430, 5,633,425, 5,641,780, 5,660,829, 5,661,016, 5,686,237, 5,693,762, 5,703,080, 5,712,374, 5,714,586, 5,739,116, 5,739,350, 5,770,429, 5,773,001, 5,773,435, 5,786,377 5,786,486, 5,789,650, 5,814,318, 5,846,545, 5,874,299, 5,877,296, 5,877,397, 5,885,793, 5,939,598, 5,962,216, 5,969,108, 5,985,908, 6,060,608, 6,066,742, 6,075,181, 6,103,236, 6,114,598, 6,130,237, 6,132,722, 6,143,901, 6,150,584, 6,162,963, 6,172,197, 6,180,370, 6,194,612, 6,214,345, 6,262,271, 6,281,354, 6,310,209, 6,329,497, 6,342,480, 6,486,326, 6,512,101, 6,521,404, 6,534,660, 6,544,731, 6,548,530, 6,555,313, 6,555,693, 6,566,336, 6,586,618, 6,593,081, 6,630,579, 6,756,397, 6,759,509, 6,762,179, 6,884,869, 6,897,034, 6,946,455, 7,049,316, 7,087,600, 7,091,186, 7,115,573, 7,129,261, 7,214,663, 7,223,837, 7,304,032, 7,329,507, 7,329,760, 7,388,026, 7,655,660, 7,655,661, 7,906,545, and 8,012,978. Examples of the structures of the conjugate of the antibody-CC-1065 analogs via the bridge linker are as the following CC01, CCO2, and CC03.

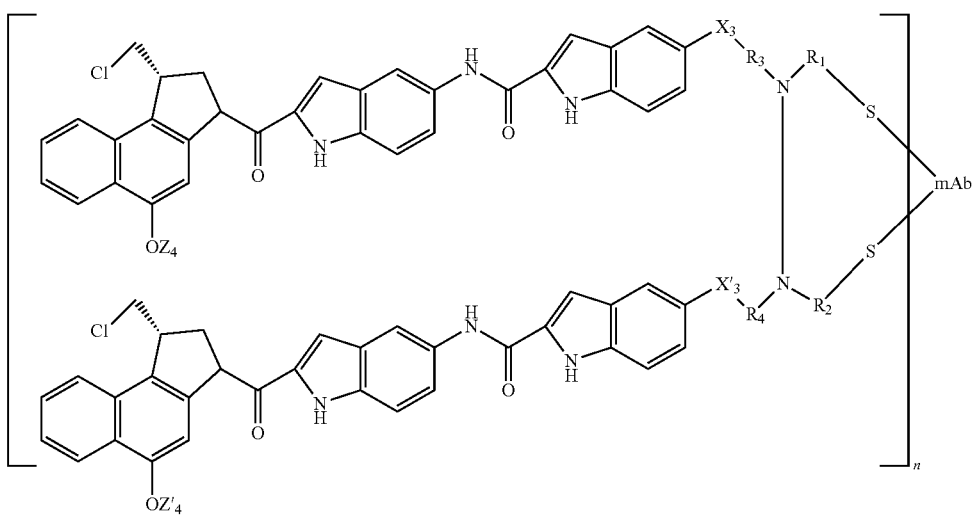

CC01

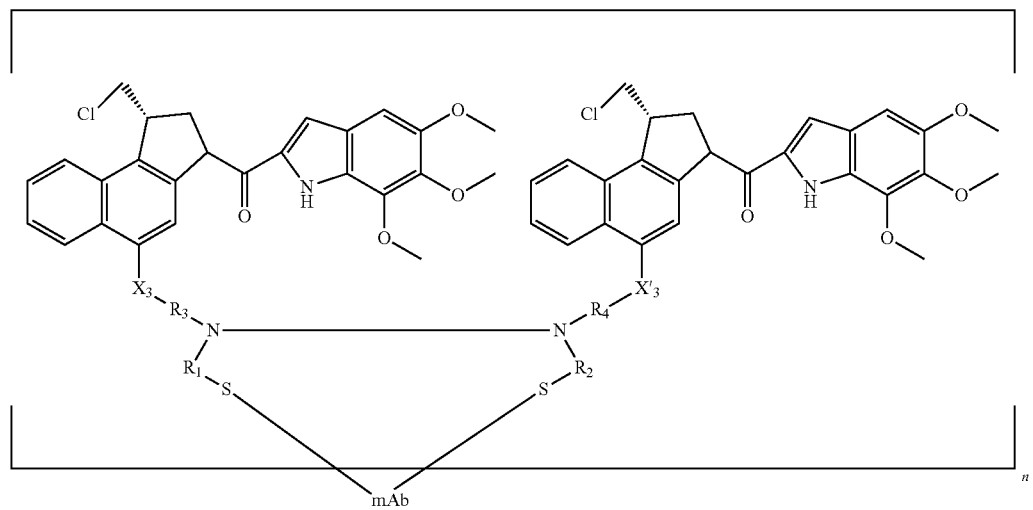

CC02

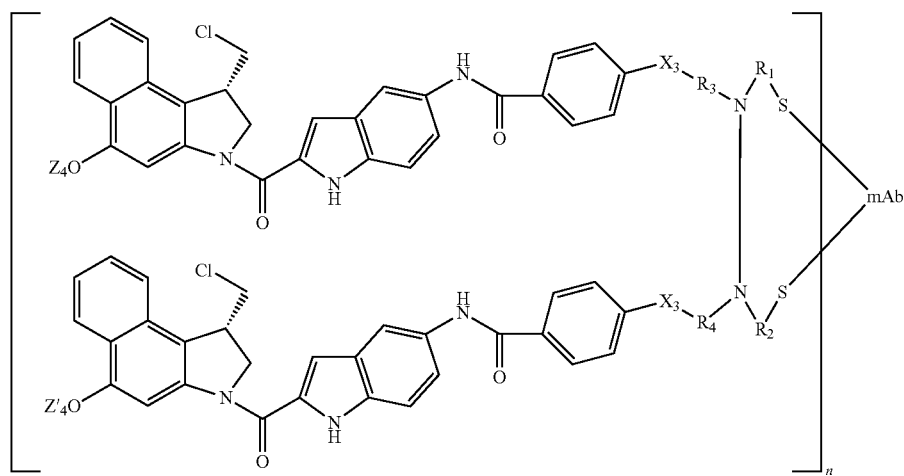

CC03

Wherein mAb is an antibody; n is 1~20; $Z_4$ and $Z'_4$ are independently H, $PO(OM_1)(OM_2)$, $SO_3M_1$, $CH_2PO(OM_1)(OM_2)$, $CH_3N(CH_2CH_2)_2NC(O)-$, $O(CH_2CH_2)_2NC(O)-$, or glycoside; $X_3$ and $X'_3$ are independently O, NH, $NR_1$, NHC(O), OC(O), CO, $R_1$, or absent; $M_1$ and $M_2$ is independently Na, K, H, $NH_4$, $NR_1R_2R_3R_4$; $R_1$, $R_2$, $R_3$, and $R_4$ are the same defined in Formula (I).

Daunorubicin/Doxorubicin Analogues are also preferred for conjugation via the bridge linkers of the present patent. The preferred structures and their synthesis are exampled in: Hurwitz, E., et al., Cancer Res. 35, 1175-1181 (1975). Yang, H. M., and Reisfeld, R. A., Proc. Natl. Acad. Sci. 85, 1189-1193 (1988); Pietersz, C. A., E., et al., E., et al.," Cancer Res. 48, 926-9311 (1988); Trouet, et al., 79, 626-629 (1982); Z. Brich et al., J. Controlled Release, 19, 245-258 (1992); Chen et al., Syn. Comm., 33, 2377-2390, 2003; King et al., Bioconj. Chem., 10, 279-288, 1999; King et al., J. Med. Chem., 45, 4336-4343, 2002; Kratz et al., J Med Chem. 45, 5523-33. 2002; Kratz et al., Biol Pharm Bull. Jan. 21, 56-61, 1998; Lau et al., Bioorg. Med. Chem. 3, 1305-1312, 1995; Scott et al., Bioorg. Med. 1 Chem. Lett. 6, 1491-1496; 1996; Watanabe et al., Tokai J. Experimental Clin. Med. 15, 327-334, 1990; Zhou et al., J. Am. Chem. Soc. 126, 15656-7, 2004; WO 01/38318; U.S. Patent No.). U.S. Pat. Nos. 5,106,951; 5,122,368; 5,146,064; 5,177,016; 5,208,323; 5,824,805; 6,146,658; 6,214,345; 7569358; 7,803,903; 8,084,586; 8,053,205. Examples of the structures of the conjugate of the antibody-CC-1065 analogs via the bridge linker are as the following Da01, Da02, Da03 and Da04.

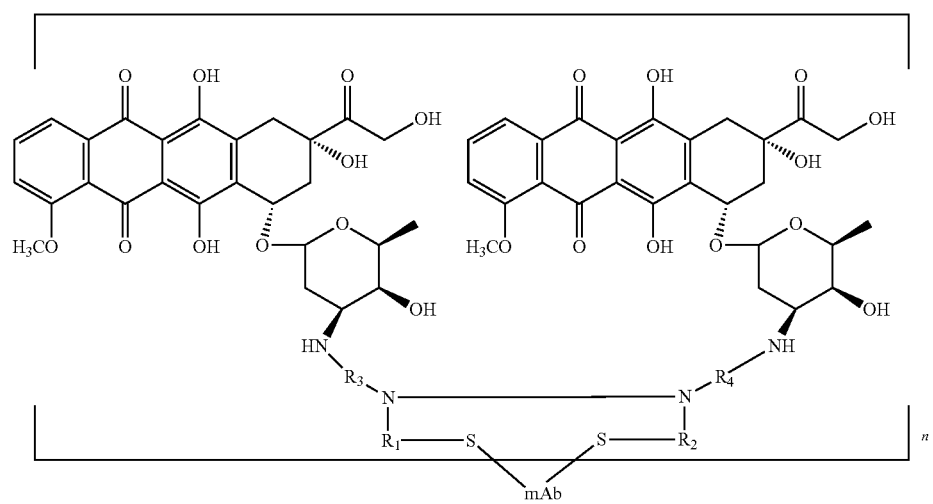
Da01
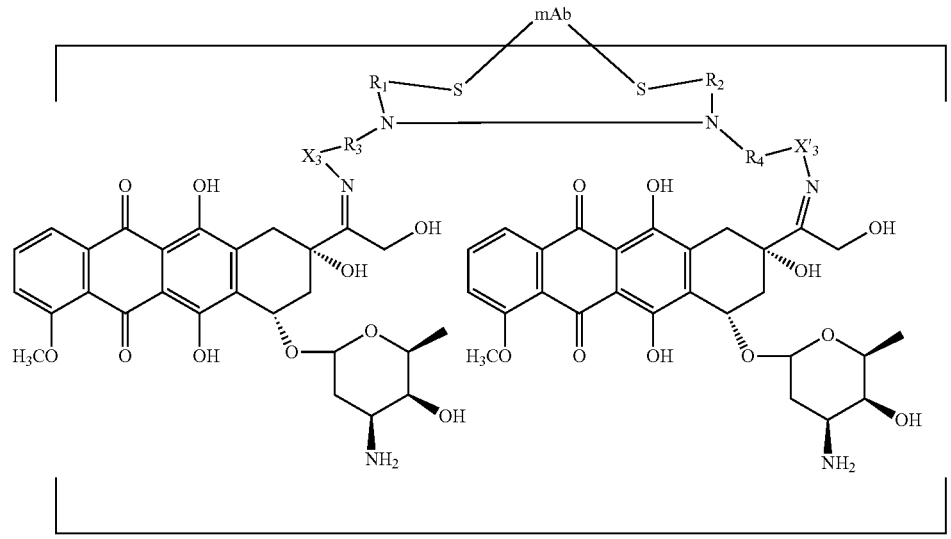
Da02
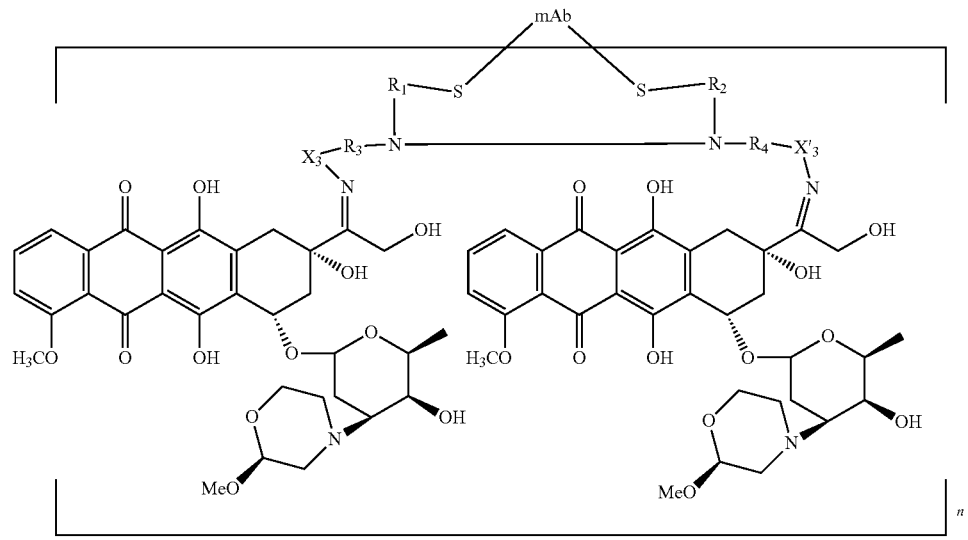
Da03

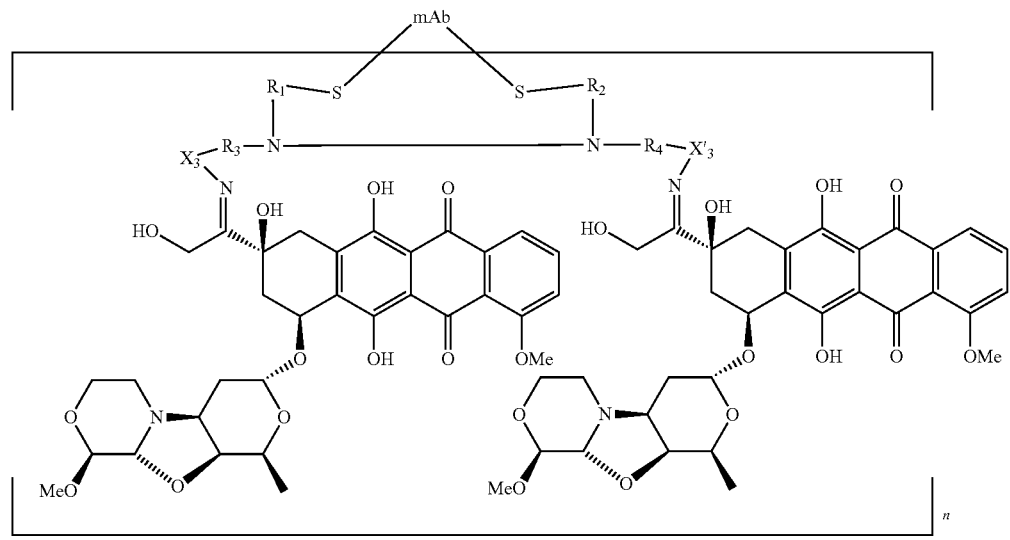

Da04

Wherein mAb is an antibody; n is 1~20; $X_3$ and $X_3'$ are independently O, NH, $NR_1$, NHC(O), OC(O), CO, C(O)$NR_1$, C(O)NH, $R_1$, or absent; $R_1$, $R_2$, $R_3$, and $R_4$ are the same defined in Formula (I).

Auristatins and dolastatins are preferred in conjugation via the bridge linkers of this patent. The auristatins (e. g. auristain E (AE) auristatin EB (AEB), auristatin EFP (AEFP), monomethyl auristatin E (MMAE), Monomethyl-auristatin (MMAF), Auristatin F phe-nylene diamine (AFP) and a phenylalanine variant of MMAE) which are synthetic analogs of dolastatins, are described in Int. J. Oncol. 15:367-72 (1999); Molecular Cancer Therapeutics, vol. 3, No. 8, pp. 921-932 (2004); U.S. application Ser. Nos. 11/134,826, 20060074008, 2006022925. U.S. Pat. Nos. 4,414,205, 4,753,894, 4,764,368, 4,816,444, 4,879,278, 4,943,628, 4,978,744, 5,122,368, 5,165,923, 5,169,774, 5,286,637, 5,410,024, 5,521,284, 5,530,097, 5,554,725, 5,585,089, 5,599,902, 5,629,197, 5,635,483, 5,654,399, 5,663,149, 5,665,860, 5,708,146, 5,714,586, 5,741,892, 5,767,236, 5,767,237, 5,780,588, 5,821,337, 5,840,699, 5,965,537, 6,004,934, 6,033,876, 6,034,065, 6,048,720, 6,054,297, 6,054,561, 6,124,431, 6,143,721, 6,162,930, 6,214,345, 6,239,104, 6,323,315, 6,342,219, 6,342,221, 6,407,213, 6,569,834, 6,620,911, 6,639,055, 6,884,869, 6,913,748, 7,090,843, 7,091,186, 7,097,840, 7,098,305, 7,098,308, 7,498,298, 7,375,078, 7,462,352, 7,553,816, 7,659,241, 7,662,387, 7,745,394, 7,754,681, 7,829,531, 7,837,980, 7,837,995, 7,902,338, 7,964,566, 7,964,567, 7,851,437, 7,994,135. Examples of the structures of the conjugate of the antibody-auristatins via the bridge linker are as the following Au01, Au02, Au03, Au04, and Au05.

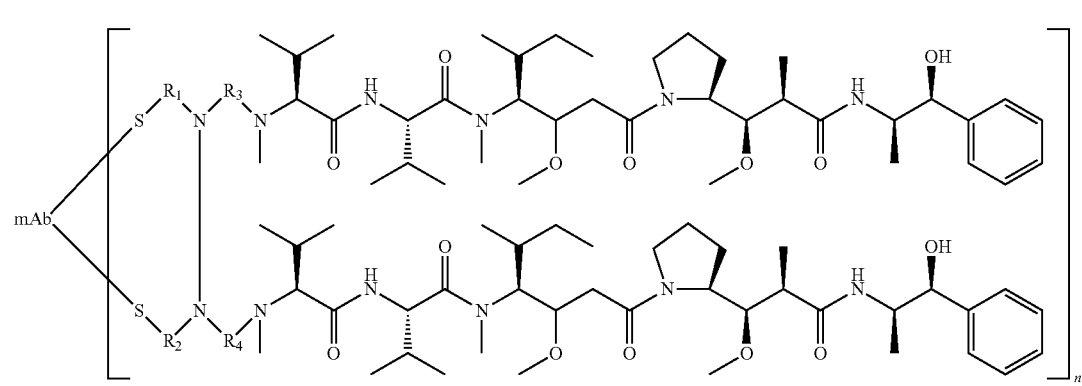

Au01

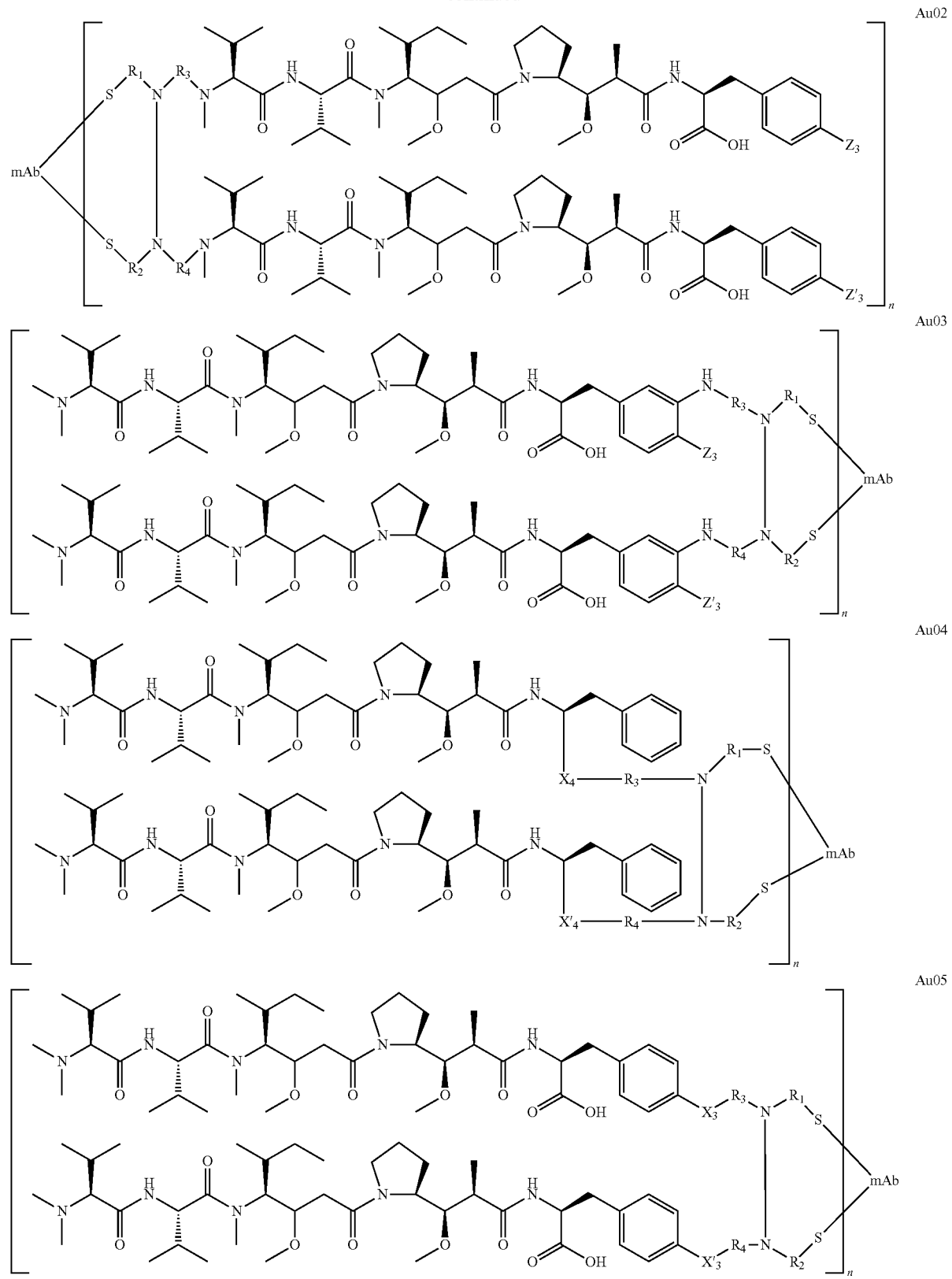
Wherein mAb is an antibody; n is 1~20; $X_3$ and $X'_3$ are independently $CH_2$, O, NH, $NR_1$, NHC(O), NHC(O)NH, C(O), OC(O), $R_1$, or absent; $X_4$ and $X'_4$ are independently $CH_2$, C(O), C(O)NH, $C(O)N(R_1)$, $R_1$, or C(O)O; $Z_3$ and $Z'_3$ are independently H, $R_1$, $OP(O)(OM_1)(OM_2)$, $OCH_2OP(O)(OM_1)(OM_2)$, $OSO_3M_1$, or O-glycoside (glucoside, galactoside, mannoside, glucuronoside, alloside, fructoside, etc), NH-glycoside, S-glycoside, or $CH_2$-glycoside; $M_1$ and $M_2$ are independently H, Na, K, Ca, Mg, $NH_4$, or $NR_1R_2R_3R_4$; $R_1$, $R_2$, $R_3$, and $R_4$ are the same defined in in Formula (I).

The benzodiazepine dimers (e. g. dimmers of pyrrolobenzodiazepine (PBD) or (tomaymycin), indolinobenzodiazepines, imidazobenzothiadiazepines, or oxazolidinobenzodiazepines) which are preferred cytotoxic agents according to the present invention are exampled in the art: U.S. Pat. Nos. 8,163,736; 8,153,627; 8,034,808; 7,834,005; 7,741,319; 7,704,924; 7,691,848; 7,678,787; 7,612,062; 7,608,615; 7,557,099; 7,528,128; 7,528,126; 7,511,032; 7,429,658; 7,407,951; 7,326,700; 7,312,210; 7,265,105; 7,202,239; 7,189,710; 7,173,026; 7,109,193; 7,067,511; 7,064,120; 7,056,913; 7,049,311; 7,022,699; 7,015,215; 6,979,684; 6,951,853; 6,884,799; 6,800,622; 6,747,144; 6,660,856; 6,608,192; 6,562,806; 6,977,254; 6,951,853; 6,909,006; 6,344,451; 5,880,122; 4,935,362; 4,764,616; 4,761,412; 4,723,007; 4,723,003; 4,683,230; 4,663,453; 4,508,647; 4,464,467; 4,427,587; 4,000,304; US patent appl. 20100203007, 20100316656, 20030195196. Examples of the structures of the conjugate of the antibody-benzodiazepine dimers via the bridge linker are as the following PB01, PB02, PB03, PB04, PB05, PB06, PB07, PB08, PB09, PB10 and PB11 as following:

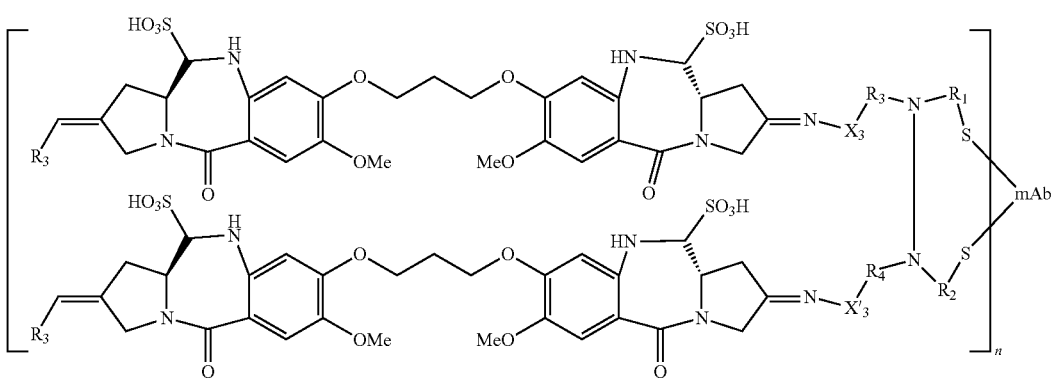

PB01

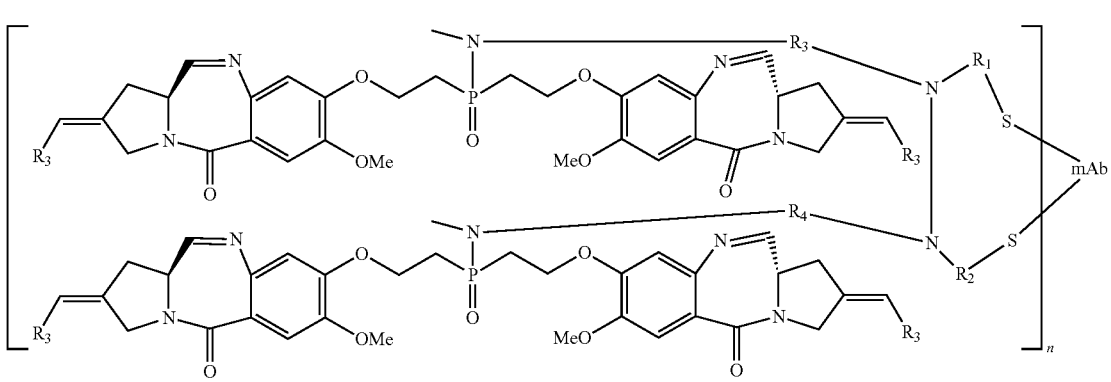

PB02

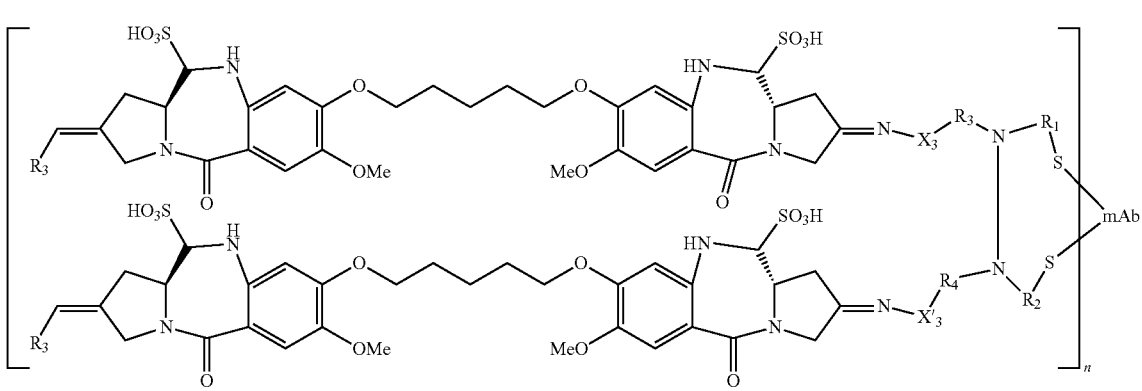

PB03

-continued
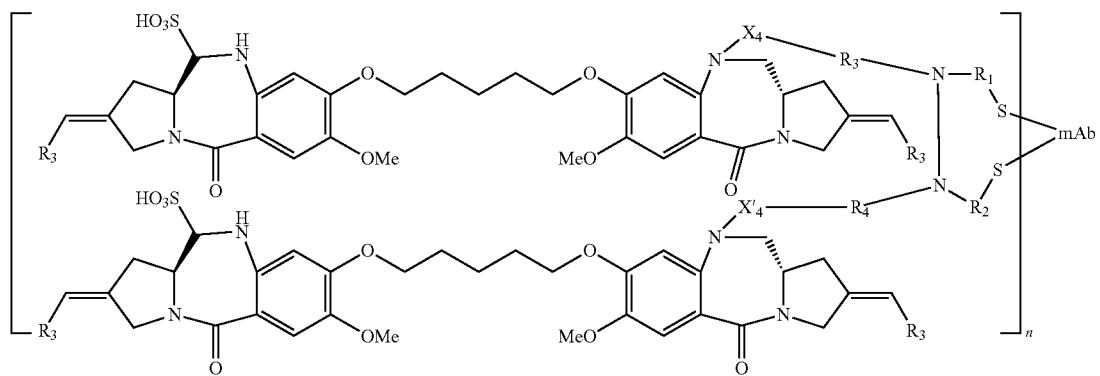
PB04
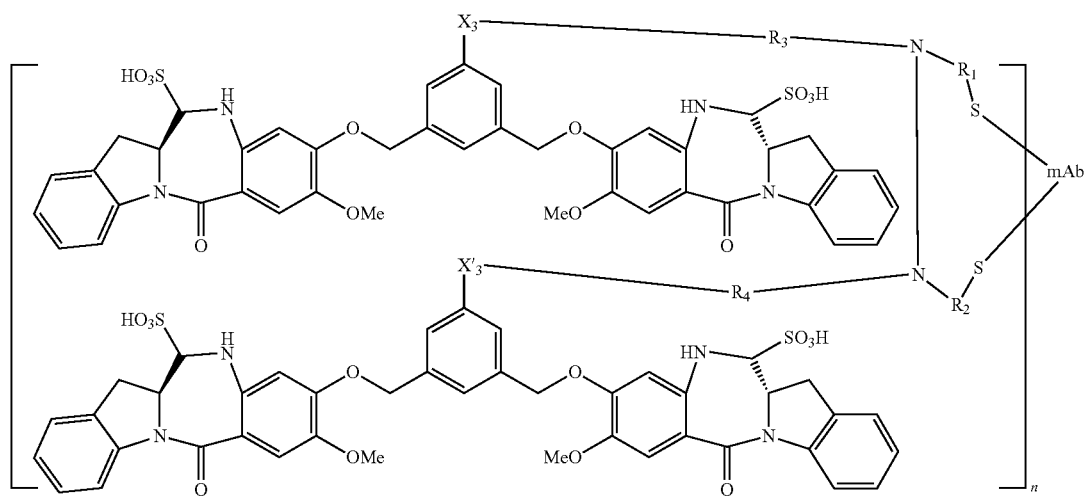
PB05
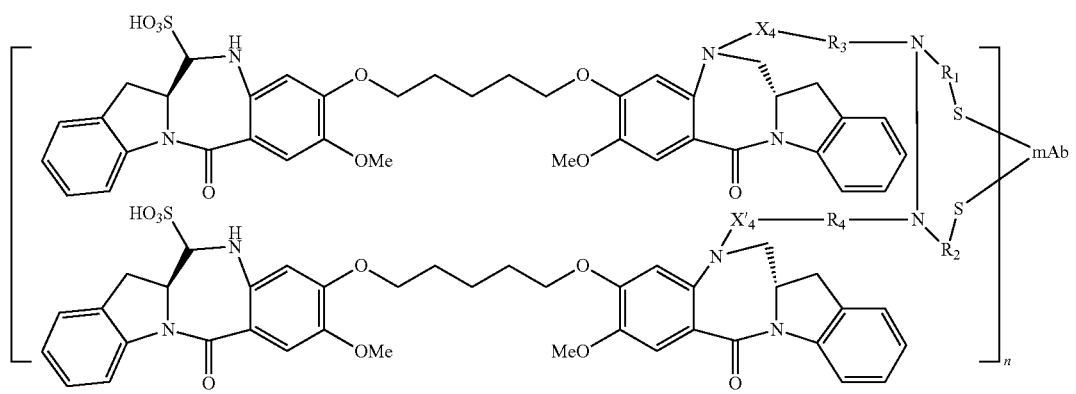
PB06

-continued
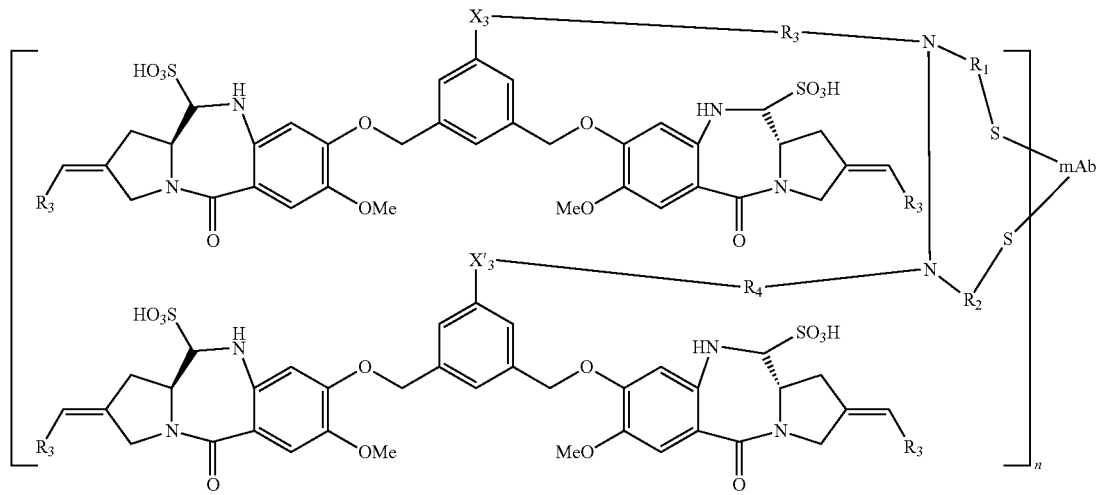
PB07
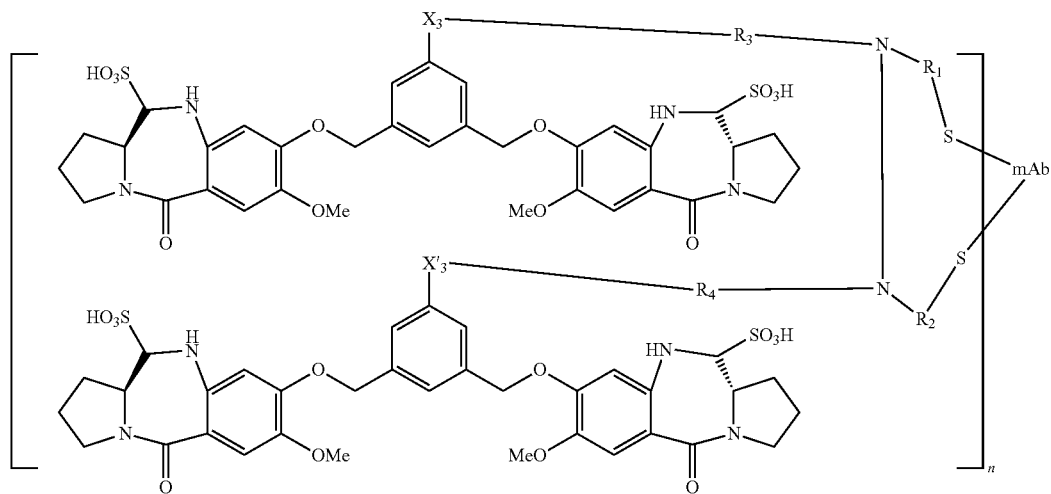
PB08
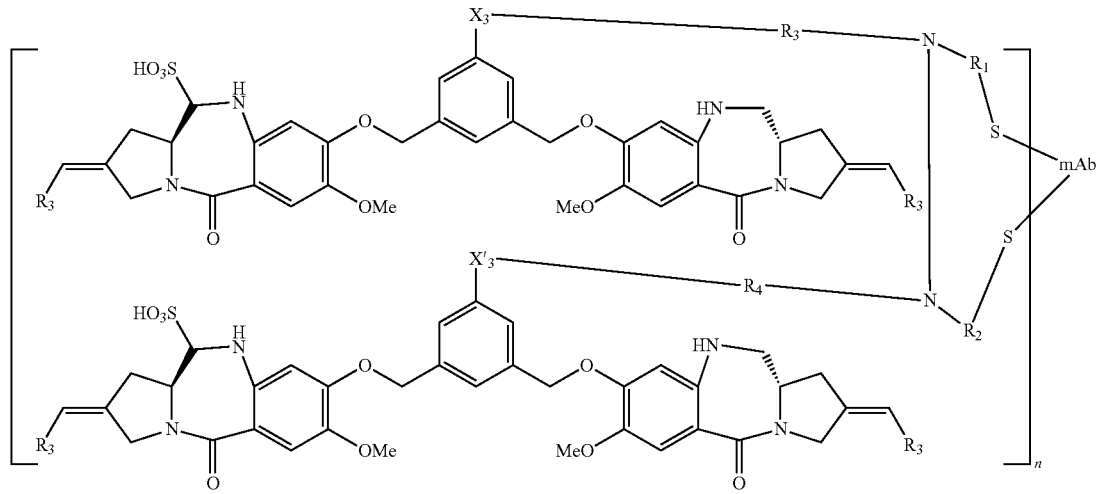
PB09

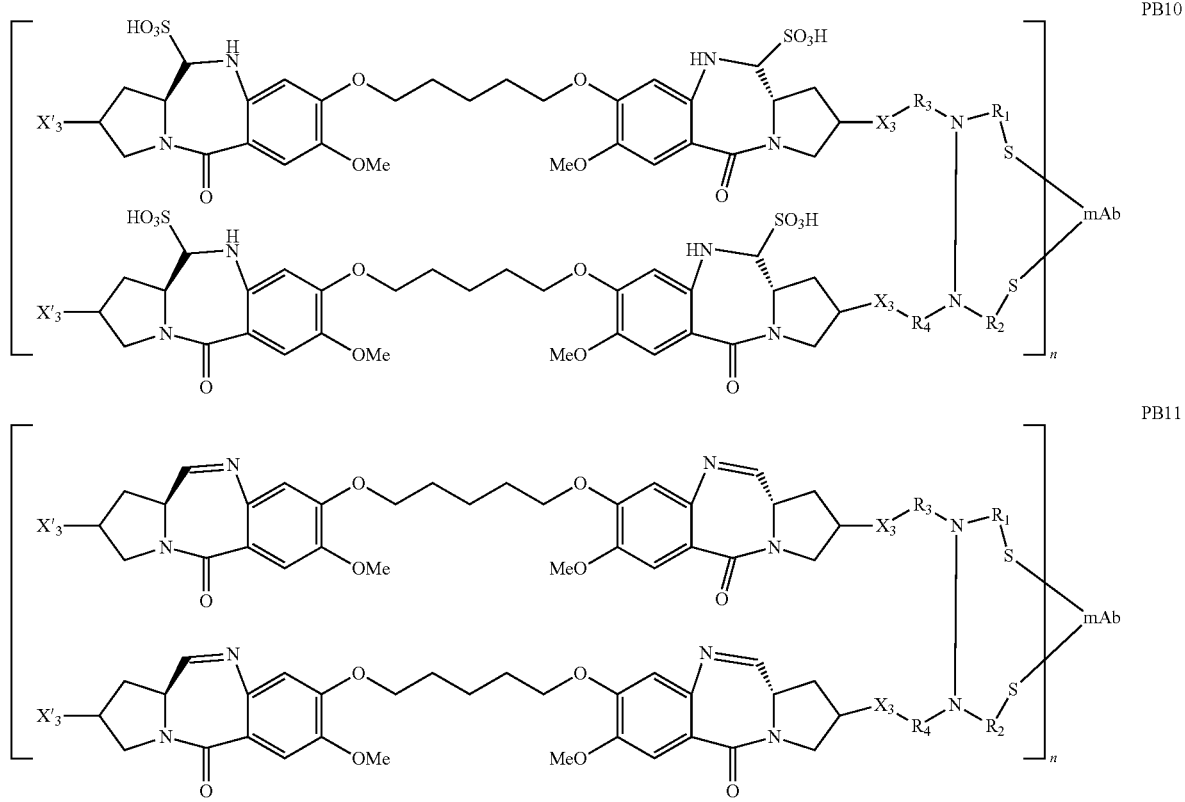

Wherein mAb is an antibody; n is 1~20; $X_3$ and $X'_3$ are independently $CH_2$, O, NH, $NR_1$, NHC(O), NHC(O)NH, C(O), $C(O)R_1$, OC(O), $C(O)N(R_1)$, $R_1$, or absent; $X_4$ and $X'_4$ are independently $CH_2$, C(O), C(O)NH, $C(O)N(R_1)$, C(O)O, $R_1$, or absent; $R_1$, $R_2$, $R_3$, and $R_4$ are the same defined in Formula (I). In addition, $R_3$ and/or $R_4$ can be absent.

The drugs/cytotoxic agents used for conjugation via a bridge linker of the present patent can be any analogues and/or derivatives of drugs/molecules described in the present patent. One skilled in the art of drugs/cytotoxic agents will readily understand that each of the drugs/cytotoxic agents described herein can be modified in such a manner that the resulting compound still retains the specificity and/or activity of the starting compound. The skilled artisan will also understand that many of these compounds can be used in place of the drugs/cytotoxic agents described herein. Thus, the drugs/cytotoxic agents of the present invention include analogues and derivatives of the compounds described herein.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), or The Shanghai Cell Culture Institute of Chinese Acadmy of Science, unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. The preparative HPLC separations were performed with Varain PreStar HPLC. NMR spectra were recorded on Varian Mercury 400 MHz Instrument. Chemical shifts (delta) are reported in parts per million (ppm) referenced to tetramethylsilane at 0.00 and coupling constants (J) are reported in Hz. The mass spectral data were acquired on a Waters Xevo Qtof mass spect equipped with Waters Acquity UPLC separations module and Acquity TUV detector.

Example 1. tert-Butyl 3-((benzyloxy)amino)propanoate (3)

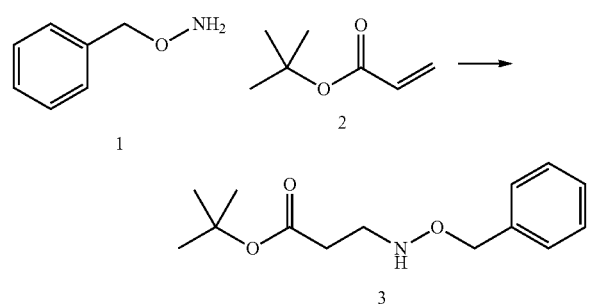

O-benzylhydroxylamine hydrochloride salt (10.0 g, 62.7 mmol) in THF (100 ml) was added Et₃N (15 ml) and tert-butyl acrylate (12.1 g, 94.5 mmol). The mixture was refluxed for overnight, concentrated and purified on SiO₂ column eluted with EtOAc/Hexane (1:4) to afford the title compound 3 (13.08 g, 83% yield). 1H NMR (CDCl₃) 7.49~7.25 (m, 5H), 4.75 (s, 2H), 3.20 (t, J=6.4 Hz, 2H), 2.54 (t, J=6.4 Hz, 2H), 1.49 (s, 9H); ESI MS m/z+ C₁₄H₂₁NNaO₃ (M+Na), cacld. 274.15, found 274.20.

Example 2. tert-Butyl 3-(hydroxyamino)propanoate (4)

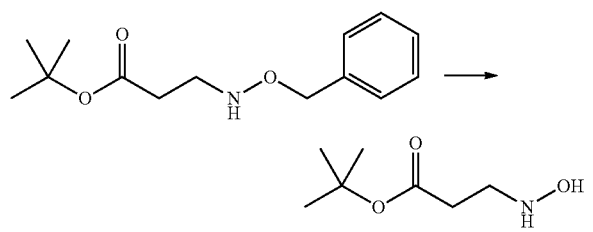

Compound 3 (13.0 g, 51.76 mmol) in methanol (100 ml) was added Pd/C (0.85 g, 10% Pd, 50% wet) in a hydrogenation vessel. After the system was evacuated under vacuum and placed under 2 atm of hydrogen gas, the reaction mixture was stirred overnight at room temperature. The crude reaction was passed through a short pad of celite rinsing with ethanol, concentrated and purified on SiO₂ column eluted with MeOH/DCM (1:101:5) to afford the title compound (7.25 g, 87% yield). 1H NMR (CDCl₃) 3.22 (t, J=6.4 Hz, 2H), 2.55 (t, J=6.4 Hz, 2H), 1.49 (s, 9H); ESI MS m/z+ C₇H₁₅NNaO₃ (M+Na), cacld. 184.10, found 184.30.

Example 3. tert-Butyl 3-((tosyloxy)amino)propanoate (5)

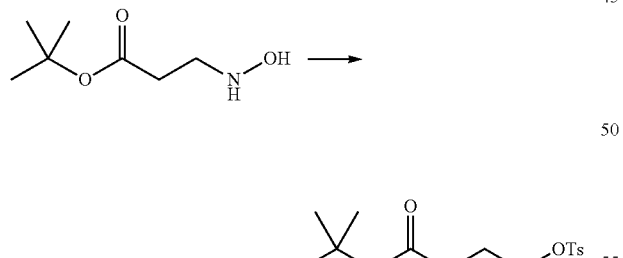

Compound 4 (5.10 g, 31.65 mmol) in the mixture of DCM (50 ml) and pyridine (20 ml) was added tosylate chloride (12.05 g, 63.42) at 4° C. After addition, the mixture was stirred at room temperature overnight, concentrated and purified on SiO₂ column eluted with EtOAc/DCM (1:10~1:6) to afford the title compound (8.58 g, 86% yield). 1H NMR (CDCl₃) 7.81 (s, 2H), 7.46 (s, 2H), 3.22 (t, J=6.4 Hz, 2H), 2.55 (t, J=6.4 Hz, 2H), 2.41 (s, 3H), 1.49 (s, 9H); ESI MS m/z+ C₁₄H₂₁NNaO₅S (M+Na), cacld. 338.11, found 338.30.

Example 4. di-tert-Butyl 3,3'-(hydrazine-1,2-diyl)dipropanoate (7)

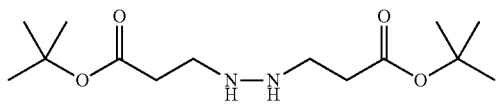 [SMILES: CC(C)(C)OC(=O)CCNNCCC(=O)OC(C)(C)C]

Tert-butyl 3-aminopropanoate 6 (3.05 g, 21.01 mmol) in THF (80 ml) was added tert-Butyl 3-((tosyloxy)amino) propanoate 5 (5.10 g, 16.18 mmol). The mixture was stirred at room temperature for 1 h and then 45° C. for 6 h. The mixture was concentrated and purified on SiO₂ column eluted with CH₃OH/DCM/Et₃N (1:12:0.01~1:8:0.01) to afford the title compound (2.89 g, 62% yield). ESI MS m/z+C₁₄H₂₈N₂NaO₄ (M+Na), cacld. 311.20, found 311.40.

Example 5. di-tert-Butyl 3,3'-(1,2-bis(3-(2,5-dioxo-2,5-dihydro-1H-pyrrol-1-yl)propanoyl)hydrazine-1,2-diyl)dipropanoate (13)

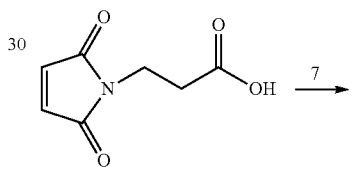

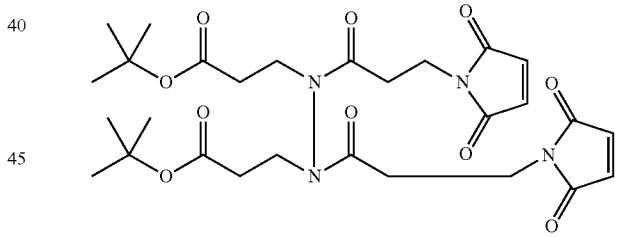

3-Maleido-propanoic acid (1.00 g, 5.91 mmol) in DCM (50 ml) was added oxalyl dichloride (2.70 g, 21.25 mmol) and DMF (50 µL). The mixture was stirred at room temperature for 2 h, evaporated, and co-evaporated with DCM/toluene to obtain crude 3-maleido-propanoic acid chloride. To the compound 7 (0.51 g, 1.76 mmol) in the mixture of DCM (35 ml) was added the crude 3-maleido-propanoic acid chloride. The mixture was stirred for overnight, evaporated, concentrated and purified on SiO₂ column eluted with EtOAc/DCM (1:15~1:8) to afford the title compound 13 (738 mg, 71% yield). ESI MS m/z+ C₂₈H₃₈N₄NaO₁₀ (M+Na), cacld. 613.26, found 613.40.

Example 6. 3,3'-(1,2-bis(3-(2,5-dioxo-2,5-dihydro-1H-pyrrol-1-yl)propanoyl)-hydrazine-1,2-diyedipropanoic acid (14)

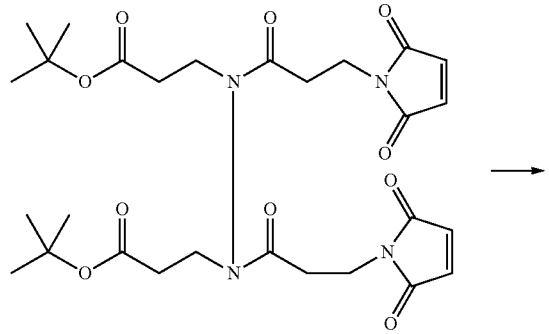

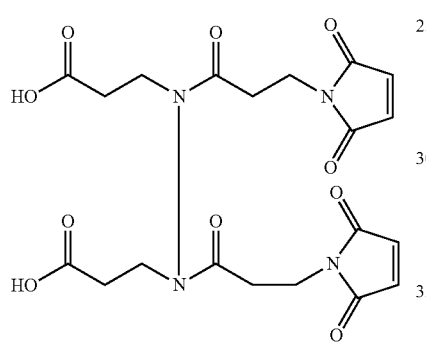

Compound 14 (700 mg, 1.18 mmol) in dioxane (4 ml) was added HCl (conc. 1 ml). The mixture was stirred for 30 min, diluted with EtOH (10 mL) and toluene (10 ml), evaporated and coevaporated with EtOH (10 ml) and toluene (10 ml) to afford the crude title product (560 mg) for next step without further purification. ESI MS m/z– $C_{20}H_{21}N_4O_{10}$ (M–H), cacld. 477.13, found 477.20.

Example 7. Bis(2,5-dioxopyrrolidin-1-yl)-3,3'-(1,2-bis(3-(2,5-dioxo-2,5-dihydro-1H-pyrrol-1-yl)propanoyl)hydrazine-1,2-diyl)dipropanoate (79)

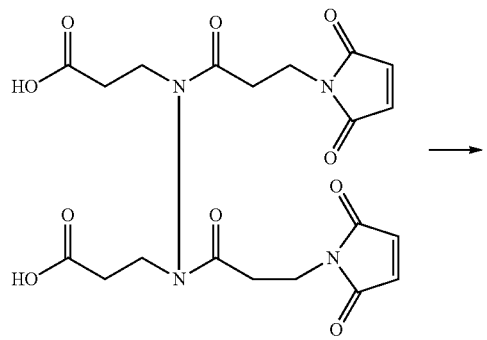

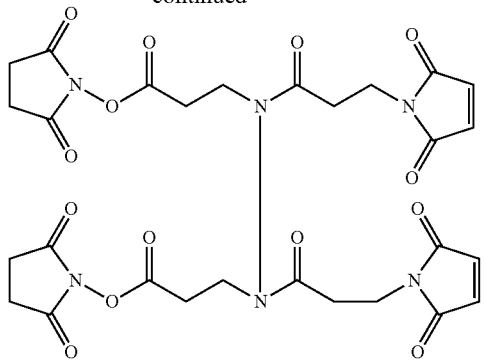

To the crude product 14 (~560 mg, ~1.17 mmol) in DMA (8 ml) was added NHS (400 mg, 3.47 mmol) and EDC (1.01 g, 5.26 mmol). The mixture was stirred for overnight, evaporated, concentrated and purified on $SiO_2$ column eluted with EtOAc/DCM (1:12~1:7) to afford the title compound 79 (520 mg, 65% yield in 2 steps). ESI MS m/z+ $C_{28}H_{28}N_6NaO_{14}$ (M+Na), cacld. 695.17, found 695.40.

Example 8. tert-Butyl 3-(2-(2-(2-hydroxyethoxy)ethoxy)ethoxy)propanoate (84)

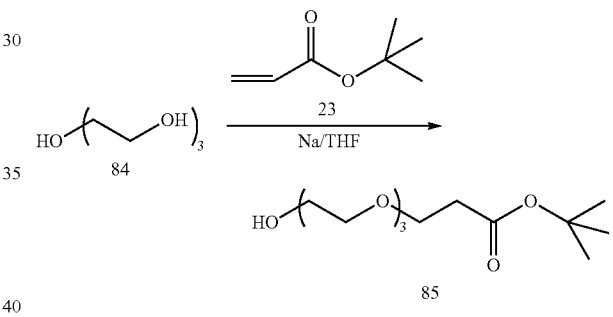

To 350 mL of anhydrous THF was added 80 mg (0.0025 mol) of sodium metal and triethylene glycol 84 (150.1 g, 1.00 mol) with stirring. After the sodium had completely dissolved, tert-butyl acrylate (24 mL, 0.33 mol) was added. The solution was stirred for 20 h at room temperature and neutralized with 8 mL of 1.0 M HCl. The solvent was removed in vacuo and the residue was suspended in brine (250 mL) and extracted with ethyl acetate (3×125 mL). The combined organic layers were washed with brine (100 mL) then water (100 mL), dried over sodium sulfate, and the solvent was removed. The resulting colorless oil was dried under vacuum to give 69.78 g (76% yields) of product 85. $^1$H NMR: 1.41 (s, 9H), 2.49 (t, 2H, J=6.4 Hz), 3.59-3.72 (m, 14H). ESI MS m/z– $C_{13}H_{25}O_6$ (M–H), cacld. 277.17, found 277.20.

Example 9. tert-Butyl 3-(2-(2-(2-(tosyloxy)ethoxy)ethoxy)ethoxy)propanoate (35)

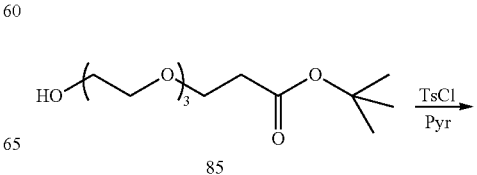

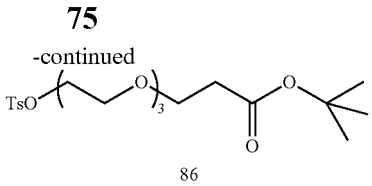

86

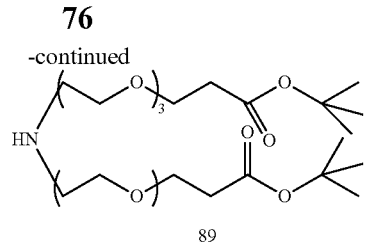

89

A solution of 85 (10.0 g, 35.95 mmol) in acetonitrile (50.0 mL) was treated with pyridine (20.0 mL). A solution of tosyl chloride (7.12 g, 37.3 mmol) in 50 mL acetonitrile was added dropwise via an addition funnel over 30 minutes. After 5 h TLC analysis revealed that the reaction was complete. The pyridine hydrochloride that had Ruined was filtered off and the solvent was removed. The residue was purified on silica gel by eluting from with 20% ethyl acetate in hexane to with neat ethyl acetate to give 11.2 g (76% yield) of compound 86. $^1$H NMR: 1.40 (s, 9H), 2.40 (s, 3H), 2.45 (t, 2H, J=6.4 Hz), 3.52-3.68 (m, 14H), 4.11 (t, 2H, J=4.8 Hz), 7.30 (d, 2H, J=8.0 Hz), 7.75 (d, 2H, J=8.0 Hz); ESI MS m/z+ $C_{20}H_{33}O_8S$ (M+H), cacld. 433.18, found 433.30.

Example 10. tert-Butyl 3-(2-(2-(2-azidoethoxy)ethoxy)ethoxy)propanoate (87)

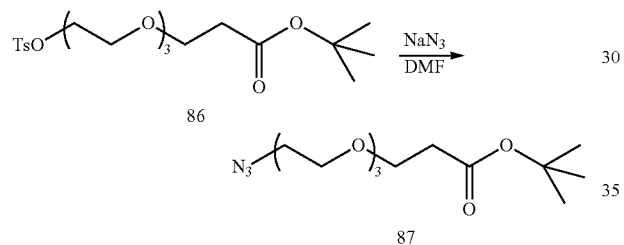

To 50 mL of DMF was added tert-butyl 3-(2-(2-(2-(tosyloxy)ethoxy)ethoxy)ethoxy)-propanoate 86 (4.0 g, 9.25 mmol) and sodium azide (0.737 g, 11.3 mmol) with stirring. The reaction was heated to 80° C. After 4 h TLC analysis revealed that the reaction was complete. The reaction was cooled to room temperature and quenched with water (25 mL). The aqueous layer was separated and extracted into ethyl acetate (3×35 mL). The combined organic layers were dried over anhydrous magnesium sulfate, filtered, and the solvent removed in vacuo. The crude azide 87 (about 90% pure by TLC) was used for next step without further purification. $^1$H NMR (CDCl$_3$): 1.40 (s, 9H), 2.45 (t, 2H, J=6.4 Hz), 3.33 (t, 2H, J=5.2 Hz), 3.53-3.66 (m, 12H). ESI MS m/z+ $C_{13}H_{26}N_3O_8$ (M+H), cacld. 304.18, found 304.20.

Example 11. 13-Amino-4,7,10-trioxadodecanoic acid tert-butyl ester, 88; 13-Amino-bis(4,7,10-trioxadodecanoic acid tert-Butyl Ester), 89

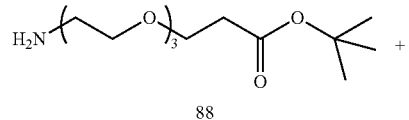

The crude azide material 87 (5.0 g, 14.84 mmol) was dissolved in ethanol (80 mL) and 300 mg of 10% Pd/C was added. The system was evacuated under vacuum and placed under 2 atm of hydrogen gas via hydrogenation reactor with vigorous stirring. The reaction was then stirred overnight at room temperature and TLC showed that the starting materials disappeared. The crude reaction was passed through a short pad of celite rinsing with ethanol. The solvent was removed and the amine purified on silica gel using a mixture of methanol (from 5% to 15%) and 1% triethylamine in methylene chloride as the eluant to give 13-amino-4,7,10-trioxadodecanoic acid tert-butyl ester 88 (1.83 g, 44% yield, ESI MS m/z+ $C_{13}H_{27}NO_5$ (M+H), cacld. 278.19, found 278.30) and 13-amino-bis(4,7,10-trioxadodecanoic acid tert-butyl ester), 89 (2.58 g, 32% yield, ESI MS m/z+ $C_{26}H_{52}NO_{10}$ (M+H), cacld. 538.35, found 538.40).

Example 12. 3-(2-(2-(2-Aminoethoxy)ethoxy)ethoxy)propanoic acid, HCl Salt, 90

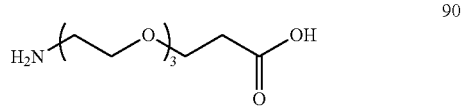

90

To 13-amino-4,7,10-trioxadodecanoic acid Tert-butyl Ester, 88 (0.80 g, 2.89 mmol) in 30 mL of dioxane was 10 ml of HCl (36%) with stirring. After 0.5 h TLC analysis revealed that the reaction was complete, the reaction mixture was evaporated, and co-evaporated with EtOH and EtOH/Toluene to form the title product in HCl salt (>90% pure, 0.640 g, 86% yield) without further purification. ESI MS m/z+ $C_9H_{20}NO_5$ (M+H), cacld. 222.12, found 222.20.

Example 13. 13-Amino-bis(4,7,10-trioxadodecanoic acid, HCl salt, 91

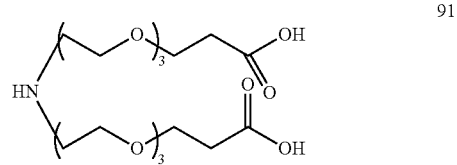

91

To 13-amino-bis(4,7,10-trioxadodecanoic acid tert-butyl ester), 89 (1.00 g, 1.85 mmol) in 30 mL of dioxane was 10 ml of HCl (36%) with stirring. After 0.5 h TLC analysis revealed that the reaction was complete, the reaction mixture was evaporated, and co-evaporated with EtOH and EtOH/Toluene to form the title product in HCl salt (>90% pure, 0.71 g, 91% yield) without further purification. ESI MS m/z+ $C_{18}H_{36}NO_{10}$ (M+H), cacld. 426.22, found 426.20.

Example 14. (S)-2-(Methylamino)propanoic Acid, Maytansinol Ester

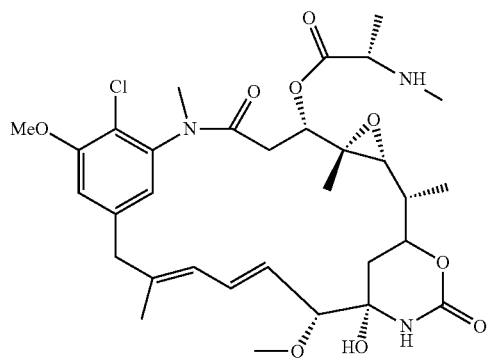 [SMILES: CN[C@@H](C)C(=O)O[C@H]1CC(=O)N(C)c2cc(cc(OC)c2Cl)C/C(C)=C/C=C/[C@@H](OC)[C@@]2(O)CC(OC(=O)N2)[C@@H](C)[C@H]2O[C@@]12C]

Maytansinol (200 mg, 0.354 mmol) was dissolved in DMF (5 ml) and THF (3 ml) on an ice/water bath was added DIPEA (0.3 ml), zinc triflate (380 mg, 1.05 mmol) and (S)-3,4-dimethyloxazolidine-2,5-dione (92 mg, 0.71 mmol). The reaction mixture was stirred under argon at room temperature for overnight, diluted with EtOAc (20 mL), washed with a solution of 1:1 brine/saturated sodium bicarbonate (8 mL). The white precipitate was filtered off, and the resulting aqueous solution was extracted with EtOAc (2×10 mL) and organic layer was washed with brine. The resulting organic layers were reduced under pressure and purified on C-18 preparative HPLC eluted with MeOH/water (10% to 65% of MeOH in 45 min, Φ50 mm×250 mm, v=80 ml/min) to obtain the title compound (156 mg, 68% yield). ESI MS m/z+ $C_{32}H_{45}ClN_3O_9$ (M+H), cacld. 650.28, found 650.20.

Example 15. (2S,2'S)-2,2'-((3,3'-(1,2-bis(3-(maleimido)propanoyl)hydrazine-1,2-diyl)bis(propanoyl))bis(methylazanediyl))dipropanoic acid, di-maytansinol esters, 108

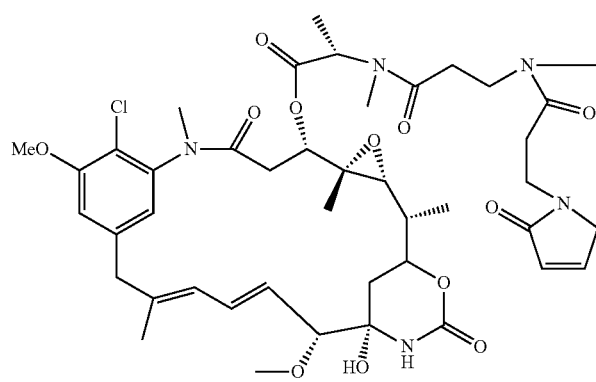 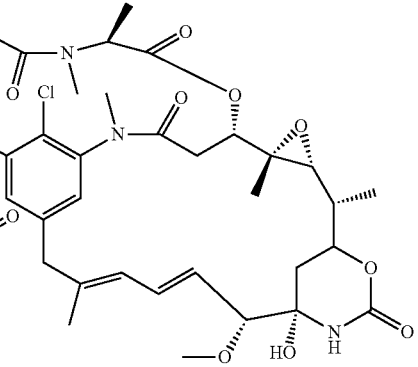

To a stirred solution of (S)-2-(Methylamino)propanoic acid, maytansinol ester (150 mg, 0.231 mmol) and 3,3'-(1,2-bis(maleido)propanoyl)-hydrazine-1,2-diyl)dipropanoic acid 14 (50 mg, 0.104 mmol) in DMA (10 ml) was added EDC (300 mg, 1.56 mmol). The mixture was stirred overnight, evaporated and purified on C-18 preparative HPLC eluted with MeOH/water (10% to 85% of MeOH in 45 min, (1320 mm×250 mm, v=20 ml/min) to afford the title compound 108 (115 mg, 63% yield). ESI MS m/z+ $C_{84}H_{107}Cl_2N_{10}O_{26}$ (M+H), cacld. 1741.67, found 1741.90.

Example 16. 3,3'-(1,2-bis(3-(maleimido)propanoyl)hydrazine-1,2-diyl)bis(N-MMAF propanamide)

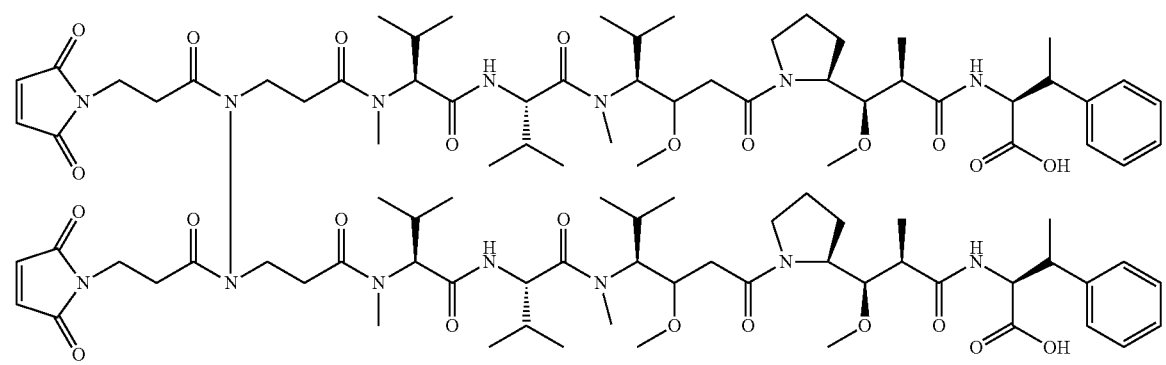

111

To a stirred solution of 3,3'-(1,2-bis(maleido)propanoyl)-hydrazine-1,2-diyl) dipropanoic acid 14 (50 mg, 0.104 mmol) in DCM (4 ml) was added oxalyl dichloride (0.4 ml, 2 M in DCM, 0.8 mmol) and DMF (10 μl). The mixture was stirred at room temperature for 2 h, evaporated, and co-evaporated with DCM/toluene to obtain crude 3,3'-(1,2-bis(maleido)propanoyl)-hydrazine-1,2-diyl)dipropanoic acid chloride 107. To a solution of MMAF 110 (160 mg, 0.219 mmol) in DCM (5 ml) was added the crude acid chloride 107. The mixture was stirred for overnight, evaporated, concentrated and purified on C-18 preparative HPLC eluted with MeOH/water (10% to 85% of MeOH in 45 min, 120 mm×250 mm, v=20 ml/min) to afford the title compound 111 (98 mg, 49% yield). ESI MS m/z+ $C_{98}H_{149}Cl_2N_{14}O_{24}$ (M+H), cacld. 1906.08, found 1906.50.

Example 17. 3,3'-(1,2-bis(3-(maleimido)propanoyl) hydrazine-1,2-diyl)bis(propanamide of N-tubulysin Analog), 119

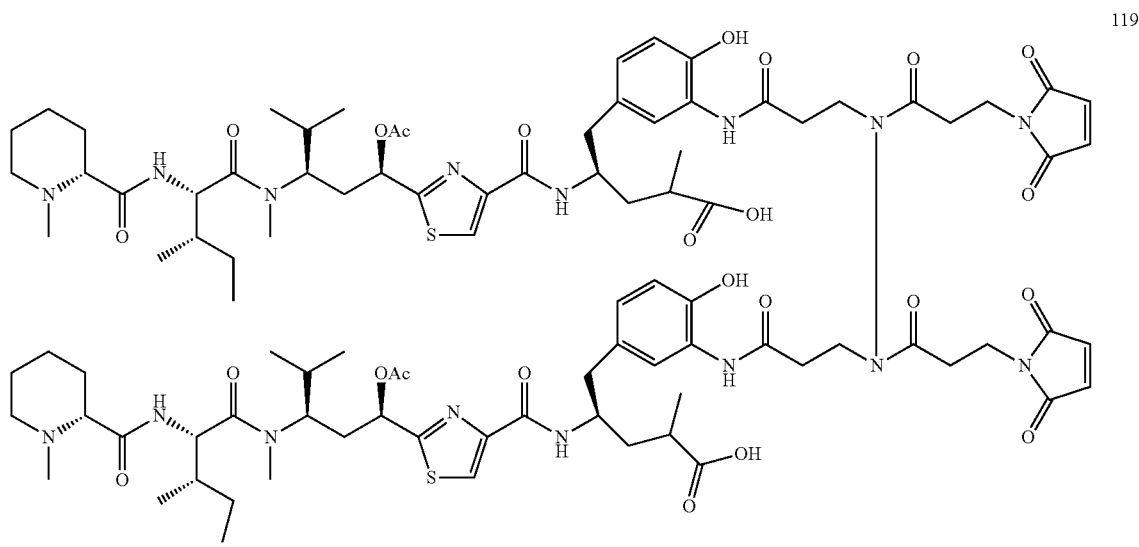 [SMILES: CC[C@H](C)[C@H](NC(=O)[C@H]1CCCCN1C)C(=O)N(C)[C@H](C[C@@H](OC(C)=O)c1nc(C(=O)N[C@@H](Cc2ccc(O)c(NC(=O)CCN(C(=O)CCN3C(=O)C=CC3=O)N(CCC(=O)Nc3cc(C[C@@H](CC(C)C(=O)O)NC(=O)c4csc([C@@H](C[C@H](C(C)C)N(C)C(=O)[C@@H](NC(=O)[C@H]5CCCCN5C)[C@@H](C)CC)OC(C)=O)n4)ccc3O)C(=O)CCN3C(=O)C=CC3=O)c2)CC(C)C(=O)O)cs1)C(C)C]

To a stirred solution of 3,3'-(1,2-bis(maleido)propanoyl)-hydrazine-1,2-diyl) dipropanoic acid 14 (50 mg, 0.104 mmol) in DCM (4 ml) was added oxalyl dichloride (0.4 ml, 2 M in DCM, 0.8 mmol) and DMF (10 μl). The mixture was stirred at room temperature for 2 h, evaporated, and co-evaporated with DCM/toluene to obtain crude 3,3'-1,2-bis(maleido)propanoyl)-hydrazine-1,2-diyl)dipropanoic acid chloride 107. To a solution of added (4R)-4-(2-((1R,3R)-1-acetoxy-3-((2S,3S)—N, 3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoic acid, 118 (Huang Y. et al, Med Chem. #44, 249$^{th}$ ACS National Meeting, Denver, Colo., Mar. 22~26, 2015; WO2014009774) (172 mg, 0.226 mmol) in DCM (5 ml) was added the crude acid chloride 107. The mixture was stirred for overnight, evaporated, concentrated and purified on C-18 preparative HPLC eluted with MeOH/water (10% to 80% of MeOH in 45 min, D20 mm×250 mm, v=20 ml/min) to afford the title compound 119 (106 mg, 52% yield). ESI MS m/z+ $C_{97}H_{139}Cl_2N_{16}O_{24}S_2$ (M+H), cacld. 1975.95, found 1976.50.

Example 18. Conjugated Compound 108, 111 or 119 to an Antibody for 109, 112 or 120 Independently

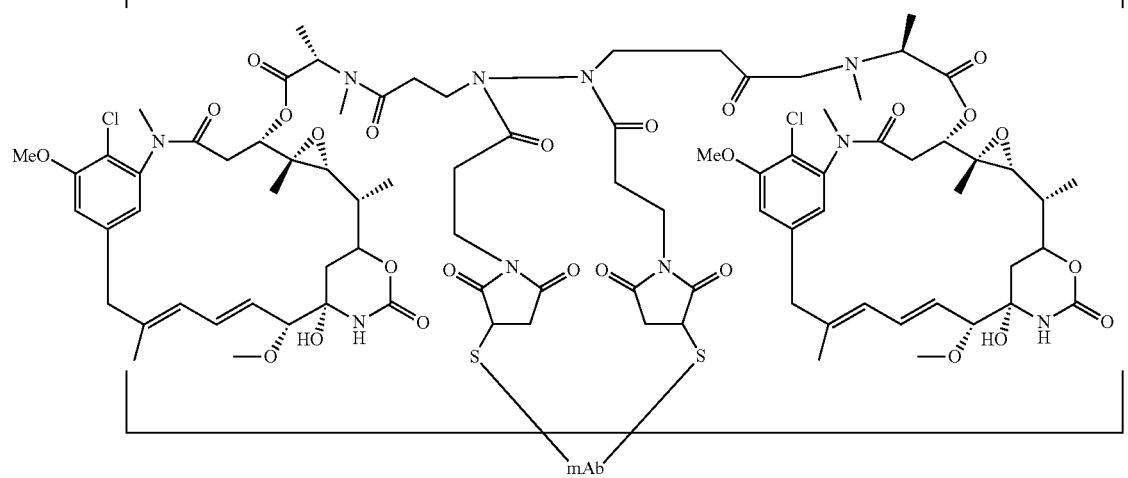

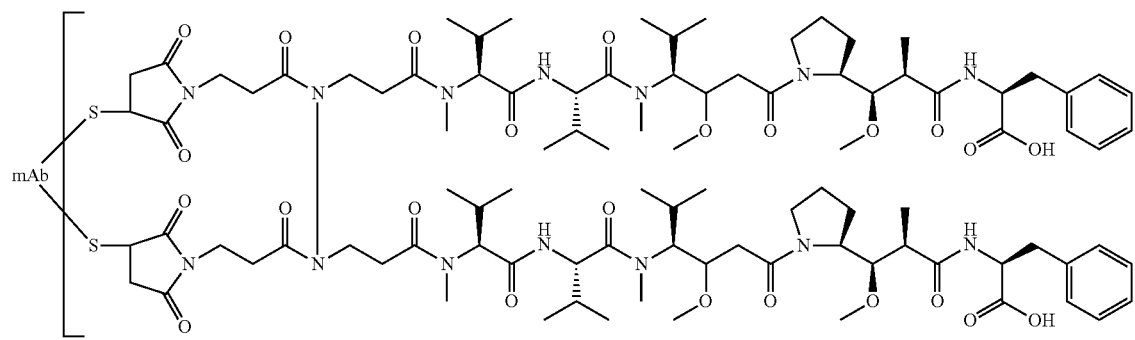

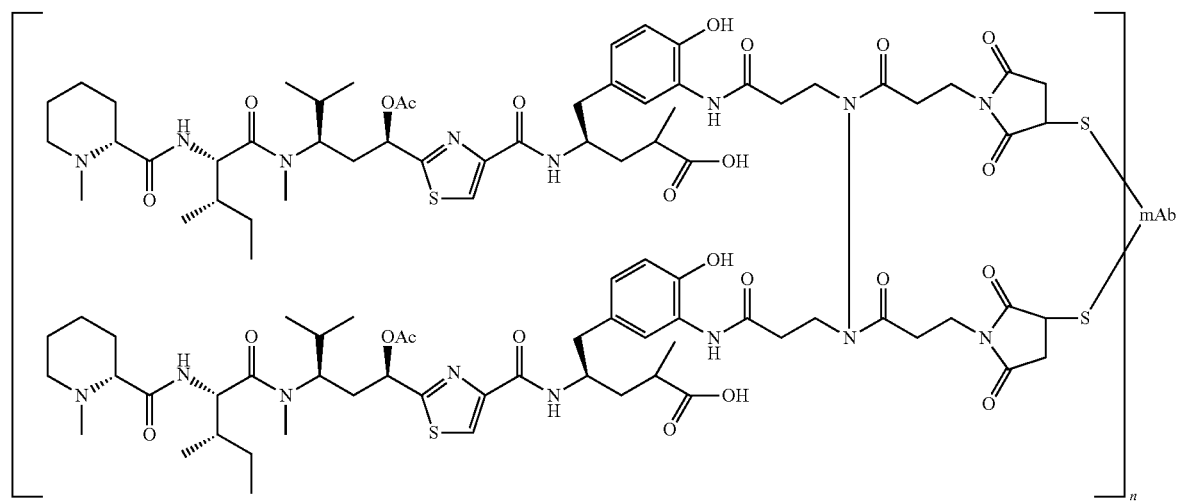

To a mixture of 2.0 mL of 10 mg/ml Herceptin in pH 6.0-8.0, were added of 0.70~2.0 mL PBS buffer of 100 mM NaH$_2$PO$_4$, pH 6.5~7.5 buffers, TCEP (28 μL, 20 mM in water) and the compound 108, 111 or 119 (14 μL, 20 mM in DMA) independently. The mixture was incubated at RT for 2~16 h, then DHAA (135 μL, 50 mM) was added in. After continuous incubation at RT overnight, the mixture was purified on G-25 column eluted with 100 mM NaH$_2$PO$_4$, 50 mM NaCl pH 6.0~7.5 buffer to afford the conjugate compound 109, 112 or 120 independently in 13.0-45.6 ml buffer. The drug/antibody ratio (DAR) was determined via UPLC-Qtof mass spectrum. They were 95~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Conjugate 109, 15.8 mg (79% yield), DAR=3.90, 95% monomer; Conjugate 112, 16.7 mg (83% yield), DAR=3.95, 96% monomer; Conjugate 120, 16.3 mg (81% yield), DAR=3.96, 97% monomer.

Example 19. In Vitro Cytotoxicity Evaluation of Conjugates 109, 112 and 120 in Comparison with T-DM1

The cell lines used in the cytotoxicity assays were HL-60, a human promyelocytic leukemia cell line; NCI-N87, a human gastric carcinoma cell line; and SKOV3, a human ovarian carcinoma cell line. For HL-60, and NCI-N87, the cells were grown in RPMI-1640 with 10% FBS. For SKOV3 cells, the cells were grown in McCoy's 5A Medium with 10% FBS. To run the assay, the cells (180 µl, 6000 cells) were added to each well in a 96-well plate and incubated for 24 hours at 37° C. with 5% $CO_2$. Next, the cells were treated with test compounds (20 µl) at various concentrations in appropriate cell culture medium (total volume, 0.2 mL). The control wells contain cells and the medium but lack the test compounds. The plates were incubated for 120 hours at 37° C. with 5% $CO_2$. MTT (5 mg/ml) was then added to the wells (20 µl) and the plates were incubated for 1.5 hr at 37° C. The medium was carefully removed and DMSO (180 µl) was added afterward. After it was shaken for 15 min, the absorbance was measured at 490 nm and 570 nm with a reference filter of 620 nm. The inhibition % was calculated according to the following equation: inhibition %=[1−(assay-blank)/(control-blank)]×100.

The Cytotoxicity Results:

| $IC_{50}$ (nM) | N87 cell (Ag+) | SK-OV-3 cell (Ag+) | HL60 cell (Ag−) |
|---|---|---|---|
| Conjugate 109 | 0.161 nM | 0.118 nM | >15 nM |
| Conjugate 112 | 0.101 nM | 0.088 nM | >10 nM |
| Conjugate 120 | 0.095 nM | 0.073 nM | >10 nM |
| T-DM1 | 0.266 nM | 0.177 nM | >15 nM |

All three conjugates were more potent than T-DM1. Specificity of conjugate 109 for N87 cell was over 93 and for SK-OV-3 cell was over 127; Specificity of conjugate 112 for N87 cell was over 99 and for SK-OV-3 cell was over 113; Specificity of conjugate 120 for N87 cell was over 105 and for SK-OV-3 cell was over 136; Specificity of conjugate T-DM1 for N87 cell was over 56 and for SK-OV-3 cell was over 84.

Example 20. Antitumor Activity In Vivo

The in vivo efficacy of conjugates 109, 112 and 120 along with T-DM1 were evaluated in a human gastric carcinoma N-87 cell line tumor xenograft models. Five-week-old female BALB/c Nude mice (30 animals) were inoculated subcutaneously in the area under the right shoulder with N-87 carcinoma cells ($5 \times 10^6$ cells/mouse) in 0.1 mL of serum-free medium. The tumors were grown for 8 days to an average size of 136 $mm^3$. The animals were then randomly divided into 5 groups (6 animals per group). The first group of mice served as the control group and was treated with the phosphate-buffered saline vehicle. The remaining four groups were treated with conjugates 109, 112, 120 and T-DM1 respectively at dose of 5 mg/Kg administered intravenously. Three dimensions of the tumor were measured every 4 days and the tumor volumes were calculated using the formula tumor volume=½(length×width×height). The weight of the animals was also measured at the same time. A mouse was sacrificed when any one of the following criteria was met: (1) loss of body weight of more than 20% from pretreatment weight, (2) tumor volume larger than 1500 $mm^3$, (3) too sick to reach food and water, or (4) skin necrosis. A mouse was considered to be tumor-free if no tumor was palpable.

Figure 12:
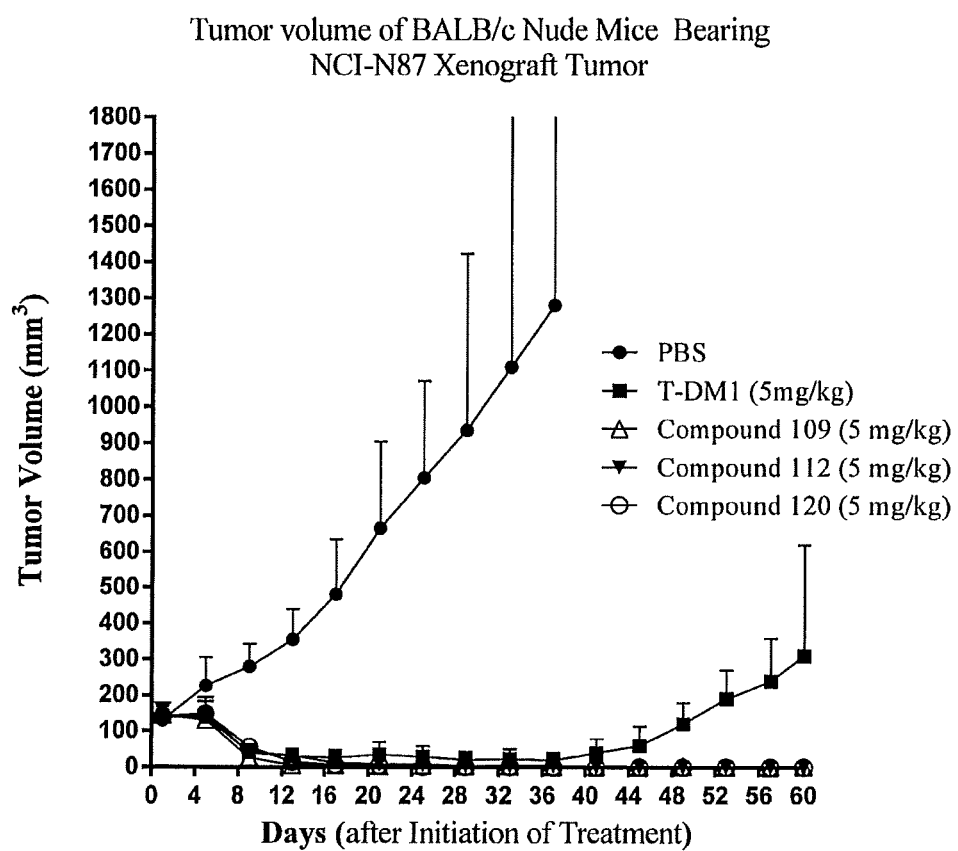
FIG. 12 shows the comparison of the anti-tumor effect of conjugate compounds 109 112 and 120 along with T-DM1 using human gastric tumor N87 cell model at dosing, 5 mg/kg, i.v., one injection. The compounds compounds 109 112 and 120 were better than T-DM1: All three compounds completely eradicated the tumor at day 13~21 till day 60 (the end of experiment). In contrast T-DM1 did not completely eliminate the tumor and only inhibited the tumor growth for about 44 days.

The results were plotted in FIG. 12. All the four conjugates compounds did not cause the animal body weight loss. And the animals at control group were sacrificed at day 37 due to the tumor volume larger than 1500 $mm^3$ and all control animals were too sick. All 6/6 animals at the groups of compounds 109, 112, 120 had completely no tumor measurable at day 13~21 till day 60 (the end of experiment). In contrast only 2/6 animals at the group of T-DM1 had no tumor measurable at days 13 and 21 until day 37 and 45.

The invention claimed is:
1. A compound of Formula (III):

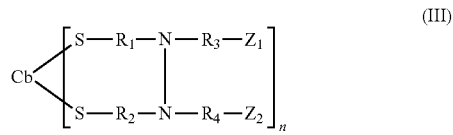

wherein:
Cb represents an antibody;
n is 1-20;
$Z_1$ and $Z_2$ are the same or different and represent a thiol; disulfide; amino; carboxy; aldehyde; ketone; maleimido; haloacetyl; hydrazine; alkoxyamino; hydroxy group; carboxy halide; N-hydroxysuccinimide ester; p-nitrophenyl ester; dinitrophenyl ester; pentafluorophenyl ester; ester formed with tetrafluorophenol, difluorophenol, monofluorophenol, pentachlorophenol, triflate, imidazole, dichlorophenol, tetrachlorophenol, 1-hydroxybenzotriazole, tosylate, mesylate, or 2-ethyl-5-phenylisoxazolium-3'-sulfonate; or anhydride;
$R_1$, $R_2$, $R_3$ and $R_4$ are the same or different, and are absent, a linear alkyl having from 1 to 8 carbon atoms, branched or cyclic alkyl having from 3 to 8 carbon atoms, linear, branched or cyclic alkenyl or alkynyl having from 2 to 8 carbon atoms, an ester, ether or amide having 2 to 8 carbon atoms, a polyethyleneoxy unit of formula $(OCH_2CH_2)_p$, wherein p is an integer from 1 to about 1000, 6-maleimidocaproyl, carbonyl, sulfonyl, thioether, azide, amine, imine, polyamine, hydrazine, hydrazone, urea, semicarbazide, carbazide, alkoxylamine, urethane, amino acid, peptide having 1 to 20 natural or unnatural amino acids, acyloxylamine, hydroxamic acid, or combination thereof, or a combination thereof with a disulfide, hydrozone, triazole, or alkoxime unit.

2. The compound of claim 1, wherein $R_1$, $R_2$, $R_3$ or $R_4$ is one or more selected from the group consisting of 6-maleimidocaproyl, maleimido propanoyl, valine-citrulline, alanine-phenylalanine, lysine-phenylalanine, p-aminobenzyloxycarbonyl, 4-thiopentanoate, 4-(N-maleimidomethyl) cyclo-hexane-1-carboxylate, 4-thio-butyrate, maleimidoethyl, 4-thio-2-hydroxysulfonyl-butyrate, pyridinyl-dithiol, alkoxy amino, ethyleneoxy, 4-methyl-4-dithiopentanoic, azido, alkynyl, dithio, and (4-acetyl)aminobenzoate.

3. The compound of claim 1, wherein $R_1$, $R_2$, $R_3$ or $R_4$ is a peptide of 1 to 20 units of natural or unnatural amino acids, or a p-aminobenzyl unit, or a 6-maleimidocaproyl unit, or a disulfide unit, or a thioether unit, or a hydrozone unit, or a triazole unit, or an alkoxime unit.

4. The compound of claim 1, wherein $Z_1$ and $Z_2$ are respectively a thiol, disulfide, amino, carboxy, aldehyde, ketone, maleimido, haloacetyl, hydrazine, alkoxyamino, or hydroxy group.

5. The compound of claim 1, wherein $Z_1$ and $Z_2$ are respectively a carboxy halide; N-hydroxysuccinimide ester; p-nitrophenyl ester; dinitrophenyl ester, pentafluorophenyl ester; ester formed with tetrafluorophenol, difluorophenol, monofluorophenol, pentachlorophenol, triflate, imidazole, dichlorophenol, tetrachlorophenol, 1-hydroxybenzotriazole, tosylate, mesylate, 2-ethyl-5-phenylisoxazolium-3'-sulfonate; or anhydride.

6. The compound of claim 5, wherein the carboxy halide is acyl halide, or the anhydride is acetyl anhydride or formyl anhydride.

7. A method for preparing the compound of claim 1, comprising reacting a compound of Formula (I) with a cell-binding molecule having a pair of free thiols:

$$Y_1—R_1—N—R_3—Z_1$$
$$Y_2—R_2—N—R_4—Z_2$$ (I)

wherein $Y_1$ and $Y_2$ are the same or different and represent a functional group that is capable of reacting with the free thiol of the cell-binding molecule.

8. A method for preparing a conjugate of a cell-binding molecule with a cytotoxic drug, comprising reacting the compound of claim 1 with the cytotoxic drug.

9. The compound of claim 1, wherein the antibody is a monoclonal antibody.

10. The compound of claim 1, wherein $Z_1$ and $Z_2$ are the same and represent a carboxy, aldehyde, ketone, ester, haloacetyl, or hydrazine.

11. The compound of claim 1, wherein $Z_1$ and $Z_2$ are respectively a maleimdo, a haloacetyl, an ethylsulfonyl, a pyridyldithio, a carboxyl, a carboxyl ester of imidazole, nitrophenol, N-hydroxysuccinimide, phenol, dinitrophenol, pentafluorophenol, tetrafluorophenol, difluorophenol, monofluorophenol, pentachlorophenol, triflate, imidazole, dichlorophenol, tetrachlorophenol, 1-hydroxybenzotriazole, tosylate; mesylate, or 2-ethyl-5-phenylisoxazolium-3'-sulfonate.

12. The compound of claim 1, wherein $Z_1$ and $Z_2$ are the same and represent —COO—C(CH$_3$)$_3$, —COCl, —COOH, —CONHNH$_2$,

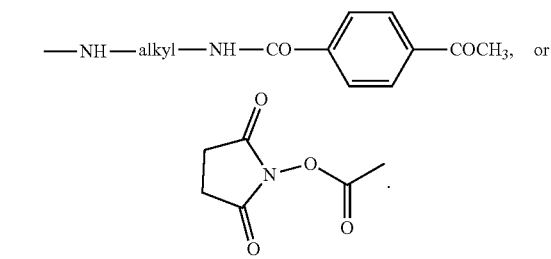

13. The compound of claim 1, wherein $R_1$, $R_2$, $R_3$ or $R_4$ is absent, or contains a linear alkyl having from 1 to 8 carbon atoms, branched or cyclic alkyl having from 3 to 8 carbon atoms, amide having 2 to 8 carbon atoms, (OCH$_2$CH$_2$)$_{1-100}$, 6-maleimidocaproyl, CO, SO$_2$, or S.

14. The compound of claim 1, wherein $R_1$ and $R_2$ are the same and represent —CO-alkyl-, —SO$_2$-alkyl-, —CO-alkyl-S—,

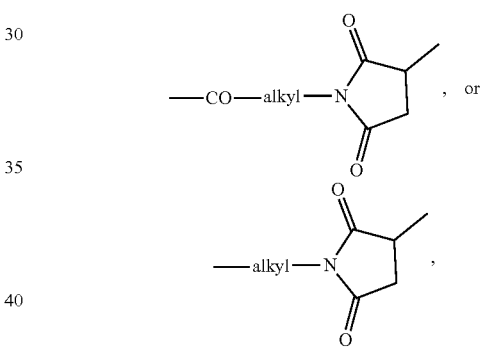

wherein alkyl is —(CH$_2$)$_{1-4}$—.

15. The compound of claim 1, wherein $R_3$ and $R_4$ are the same and represent -alkyl-, -alkyl-(CH$_2$OCH$_2$)$_m$-alkyl-, —CO-alkyl-, -alkyl-CONH—CH(-alkyl-Ph)-CONH—CH(-alkyl-NH$_2$)—, -alkyl-CONH-alkyl-(CH$_2$OCH$_2$)$_m$-alkyl-, -alkyl-CON[-alkyl-(CH$_2$OCH$_2$)$_m$-alkyl]$_2$, —CH(-alkyl-NH$_2$)—, or -alkyl-CO—, wherein m is 1 to 100, and alkyl is —(CH$_2$)$_{1-4}$—.

16. The compound of claim 1, wherein the compound is

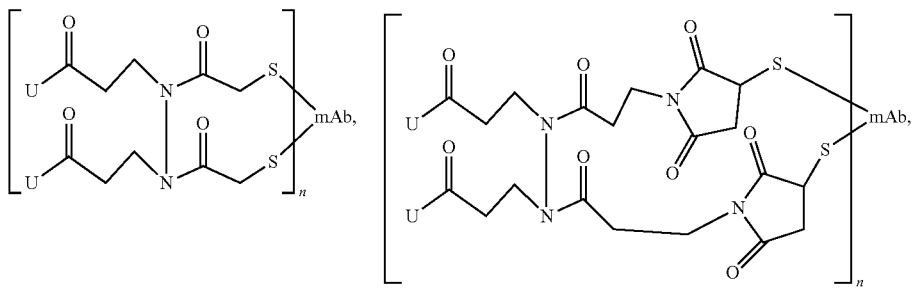

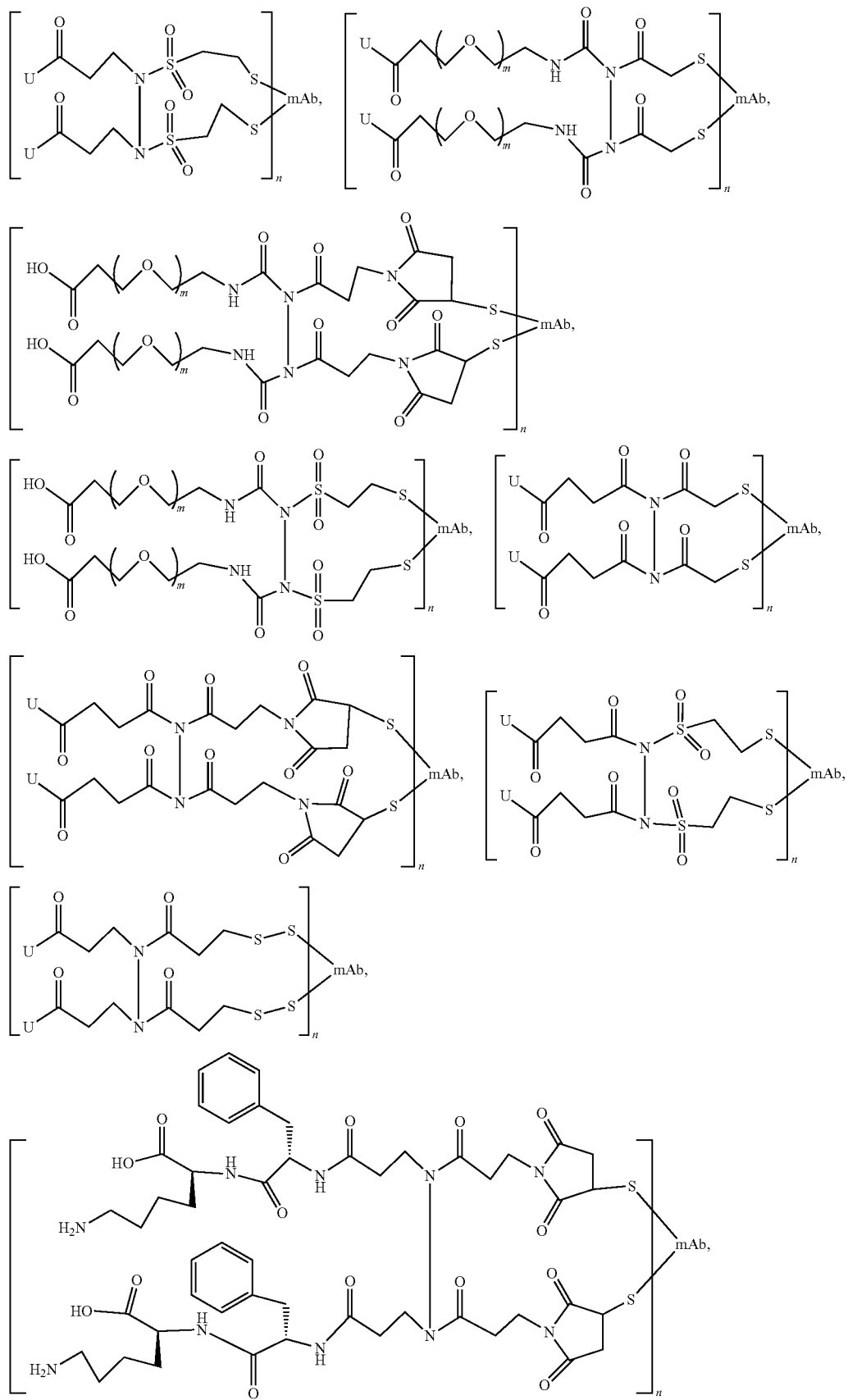

-continued
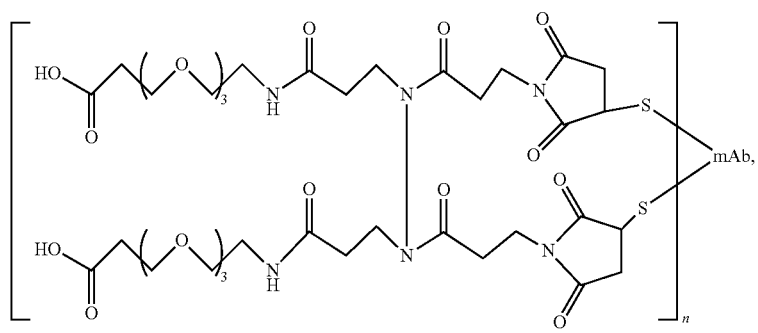
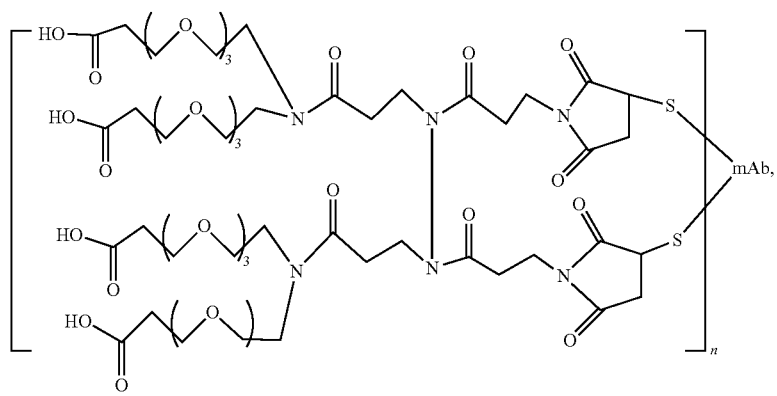
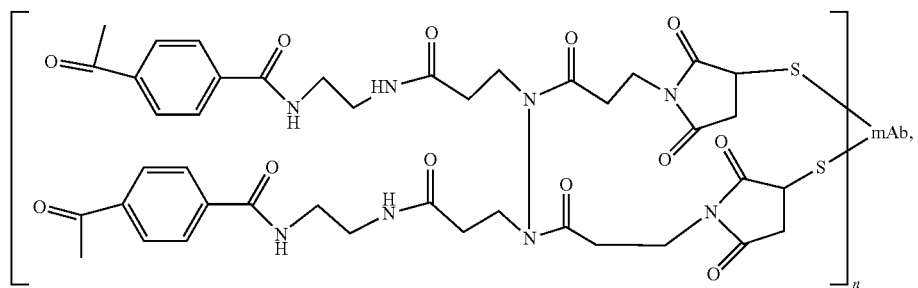
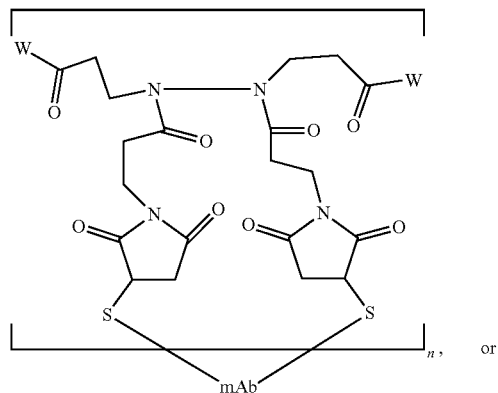, or

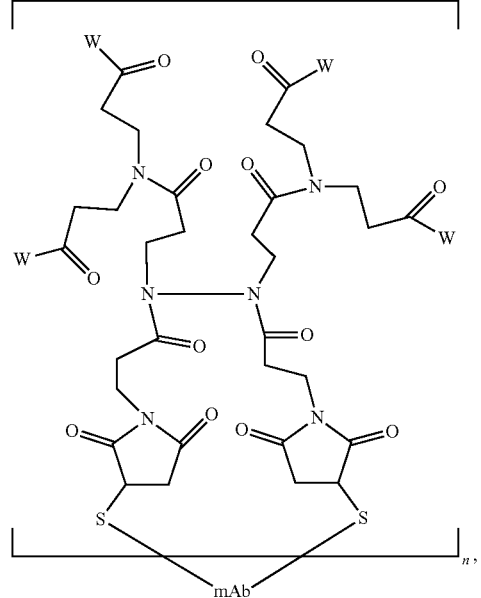
wherein U is OC(CH$_3$)$_3$ or OH, V is OH or
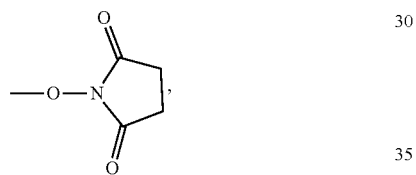
W is OH or Cl, m is 0 to 100, n is 1 to 20, and mAb is antibody.
* * * * *